US010323270B2

(12) United States Patent
Min et al.

(10) Patent No.: US 10,323,270 B2
(45) Date of Patent: Jun. 18, 2019

(54) KIT FOR DETECTING NUCLEIC ACID AND METHOD FOR DETECTING NUCLEIC ACID

(71) Applicant: SEOUL NATIONAL UNIVERSITY R&DB FOUNDATION, Seoul (KR)

(72) Inventors: Dal-Hee Min, Seoul (KR); Jieon Lee, Seoul (KR); Soo-Ryoon Ryoo, Seoul (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 686 days.

(21) Appl. No.: 14/928,330

(22) Filed: Oct. 30, 2015

(65) Prior Publication Data
US 2016/0138096 A1 May 19, 2016

Related U.S. Application Data

(63) Continuation-in-part of application No. 14/397,015, filed as application No. PCT/KR2013/003503 on Apr. 24, 2013.

(30) Foreign Application Priority Data

Apr. 24, 2012 (KR) .................. 10-2012-0042785

(51) Int. Cl.
*C12Q 1/6823* (2018.01)
*C12Q 1/6841* (2018.01)

(52) U.S. Cl.
CPC ......... *C12Q 1/6841* (2013.01); *C12Q 1/6823* (2013.01)

(58) Field of Classification Search
None
See application file for complete search history.

(56) References Cited

U.S. PATENT DOCUMENTS

2010/0248980 A1* 9/2010 Park et al. ........... C12Q 1/6837
506/9

FOREIGN PATENT DOCUMENTS

KR 10-2011-0120749 A 11/2011

OTHER PUBLICATIONS

He et al., "A Graphene Nanoprobe for Rapid, Sensitive, and Multicolor Fluorescent DNA Analysis," Adv. Funct. Mater. 2010, 20:453-459. (Year: 2010).*
Int'l. Search report of PCT/KR2013/003503 dated Jul. 4, 2013.
Guo-Jun Zhang et al., "Label-free direct detection of MiRNAs with silicon nanowire biosensors", Biosens. Bioelectron., vol. 24, No. 8, pp. 2504-2508 (Apr. 15, 2009).
Liang Cui et al., "Graphene oxide-protected DNA probes for multiplex microRNA analysis in complex biological samples based on a cyclic enzymatic amplification method", Chemical Communications, vol. 48, No. 2, pp. 194-196 (Jan. 7, 2012).
Ying Wang et al., "Aptamer/Graphene Oxide Nanocomplex for in Situ Molecular Probing in Living Cells", J. Am. Chem. Soc., vol. 132, No. 27, pp. 9274-9276 (Jul. 14, 2010).
(Continued)

*Primary Examiner* — Kaijiang Zhang
(74) *Attorney, Agent, or Firm* — The PL Law Group, PLLC

(57) ABSTRACT

The present invention relates a kit for detecting a nucleic acid and a method of detecting a nucleic acid for enabling a multiplexed-detection and real-time detection of a target nucleic acid by using properties of a graphene oxide.

6 Claims, 50 Drawing Sheets
(9 of 50 Drawing Sheet(s) Filed in Color)
Specification includes a Sequence Listing.

(56) References Cited

OTHER PUBLICATIONS

Zhang GJ, "Silicon nanowire biosensor for ultrasensitive and label-free direct detection of miRNAs", Methods in Molecular Biology, vol. 676, pp. 111-121 (2011).

Haifeng Dong et al., "Highly sensitive multiple microRNA detectioin based on fluorescence quenching of graphene oxide and isothermal stranddisplacement polymerase reaction", Analytical Chemistry, vol. 84, pp. 4587-4593 (Apr. 17, 2012).

Rong Hu et al., "Nucleic acid-functionalized nanomaterials for bioimaging applications", Journal of Materials Chemistry, vol. 48, No. 2, pp. 194-196 (2011).

Shiping Song et al., "Functional nanoprobes for ultrasensitive detection of biomolecules", Chemical Society Reviews, vol. 39, No. 11, pp. 4234-4243 (2010).

* cited by examiner

| | Carbon | Hydrogen | Oxygen |
|---|---|---|---|
| Composition (%) | 49.72 | 1.76 | 39.61 |

| Sample | Zeta Potential (mV) | Hydrodynamic diameter (nm) |
|---|---|---|
| Graphene Oxide | 0.308 | 223.9 |

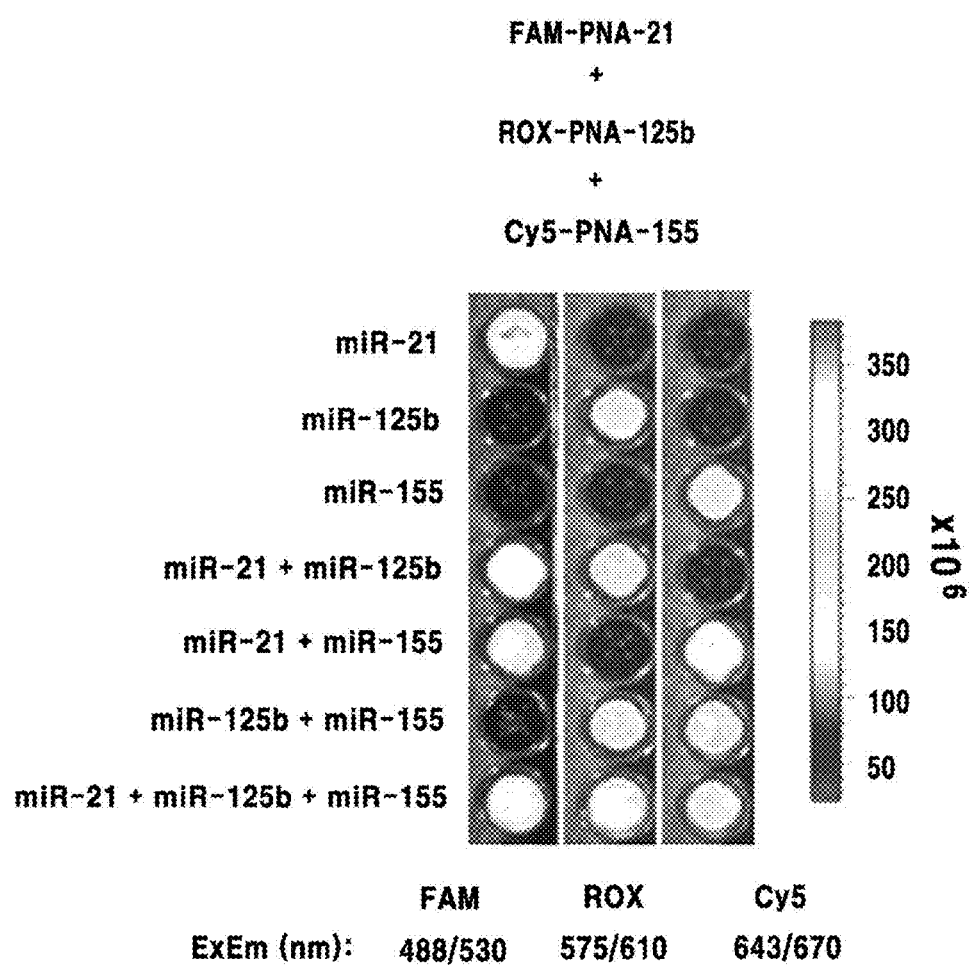

Scale bar: 100 μm

KIT FOR DETECTING NUCLEIC ACID AND METHOD FOR DETECTING NUCLEIC ACID

CROSS-REFERENCE TO RELATED APPLICATIONS

This application is a continuation-in-part of U.S. patent application Ser. No. 14/397,015 filed on Oct. 24, 2014 which is a continuation application of International Application No. PCT/KR2013/003503 filed Apr. 24, 2013, claiming priority based on Korean Patent Application No. 10-2012-0042785 filed on Apr. 24, 2012 in the Korean Intellectual Property Office, the entire disclosure of all of which are incorporated herein by reference for all purposes.

TECHNICAL FIELD

The embodiments described herein pertain generally to a kit for detecting a nucleic acid and a method of detecting a nucleic acid.

BACKGROUND

Graphene has a plane monolayer structure including a 2-dimensional lattice made of carbon atoms. Graphene is a basic structural element of various allotropes of graphite having different dimensional structures. That is, the graphene may be a basic structure of fullerene (0-dimensional structure), carbon nanotube (1-dimensional structure) or graphite stacked in a 3-dimensional structure. In many of recent researches, peculiar properties of graphene, such as a zero band gap, derived from its hexagonal crystalline structure, two interpenetrating triangular subordinate lattice structures and its one-atom-size thickness are attracting attention. Further, graphene also has a peculiar electron transmission property, and, thus, it exhibits very special phenomena which have not been conventionally observed. A half-integer quantum Hall effect and a bipolar super-current transistor effect are examples of such peculiar phenomena, and these effects are also deemed to be resulted from the unique structure of graphene. Graphene oxide (GO), which is an oxidized form of graphene, is capable of quenching a fluorescence signal of organic fluorescent dyes through FRET (Fluorescence Resonance Energy Transfer), which depends on a strong bond between the graphene oxide and hydrophobic molecules and a single-strand nucleic acid through π-π stacking and/or a hydrogen bond interaction and a fluorescence quenching capability of the graphene oxide.

A method of detecting a specific nucleic acid (DNA or RNA) or protein is basically an important technique in the field of scientific research. As it becomes possible to detect and investigate a specific nucleic acid or protein, researchers can specify which genetic and biological marker is an index indicating human health condition. By using such a method of detecting a nucleic acid and a protein, gene variation of pathogen present in a sample or a specific gene expression can be observed. Further, miRNA (microRNA), which is a microscopic RNA molecule composed of about twenty (20) nucleic acids and which does not encode protein is one of important biomolecules that exist within a human body, is known to be related to various biological processes such as cell proliferation or differentiation.

PNA (Peptide Nucleic Acid) is an artificially synthesized nucleic acid. Since a backbone of oligonucleic acid is composed of peptide bonds, not phosphodiester bonds, PNA is electrically neutral while having a very strong binding force and is very stable against nuclease and proteinase. Thus, when used as a probe, PNA exhibits very high stability.

Recently, a molecular biological method or biochemical method in biology is widely employed to conduct a research on miRNA. Microarray or real-time PCR as a non-array technique are examples of the most well-known existing research methods, and various other methods are also being developed. For example, there has been reported a relevant research entitled "Bio-imaging probe for detecting intracellular molecules and treating disorders" (Korean Patent Publication No. 2011-0120749). However, these methods have drawbacks in that multiplexed-detection is impossible, a real-time detection is difficult and cost of detection is high.

DISCLOSURE OF THE INVENTION

Problems to be Solved by the Invention

In view of the foregoing problems, example embodiments provide a kit for detecting a nucleic acid and a method of detecting a nucleic acid for enabling a multiplexed-detection and real-time detection of a target nucleic acid by using properties of a graphene oxide.

However, the problems sought to be solved by the present disclosure are not limited to the above description and other problems can be clearly understood by those skilled in the art from the following description.

Means for Solving the Problems

In one aspect of example embodiments, there is provided a kit for detecting a nucleic acid, including: a graphene oxide; and a PNA probe which includes a fluorescent material and is complementary to a target nucleic acid.

In another aspect of example embodiments, there is provided a method of detecting a nucleic acid, including: a step of mixing a PNA probe with a sample including a target nucleic acid, wherein the PNA probe is adsorbed on a graphene oxide and includes a fluorescent material; and a step of detecting a fluorescent light emitted from the fluorescent material, wherein the target nucleic acid is combined with the PNA probe upon the mixing step so that the PNA probe is separated from the graphene oxide and the fluorescent light is emitted from the fluorescent material.

In yet another aspect of example embodiments, there is provided a method of detecting a nucleic acid, including: a step of mixing a PNA probe with a sample including a target nucleic acid, wherein the PNA probe includes a fluorescent material and is complementary to the target nucleic acid; a step of adding a graphene oxide into the mixture; and a step of detecting quenching of a fluorescent light from the fluorescent material, wherein the rest of the PNA probe which is not hybridized with the target nucleic acid and the rest of the nucleic acid are adsorbed on the graphene oxide and thereby the fluorescent light from the fluorescent material is quenched.

Effect of the Invention

By using the kit for detecting a nucleic acid and the method for detecting a nucleic acid using the kit in accordance with the example embodiments, presence or absence of a target nucleic acid in a sample or cell and an expression pattern of the target nucleic acid can be observed in a real time as well as a multiplexed-detection of plural target nucleic acids is enabled. Further, candidates of medicinal substances and low-molecular substances capable of adjusting expression of a specific miRNA positively or negatively can be derived by performing high-throughput screening (HTS). Further, a mechanism of action of the substances derived through this process and an influence of such substances upon the control of the miRNA expression can be investigated in a cell level. Additionally, since an expression pattern of a target nucleic acid within a living cell can be observed, it is possible to derive highly reliable candidates for the low-molecular substances and medicinal substances.

The kit for detecting a nucleic acid and the method of detecting a nucleic acid using the kit in accordance with the example embodiments is cost-effective because they employs graphene oxide, which is a low-price material that can be secured in large quantity and stored stably at a room temperature. Further, since a nucleic acid used as a probe is a PNA, which is stable against nuclease, a detection reaction may occur stably. In addition, since the detection is performed based on fluorescence, it is possible to read signals quantitatively, and an existing fluorescence leader or a fluorescence microscope can be utilized.

Further, it is possible to accurately detect a target nucleic acid by excluding a mismatched double strand and further a double strand mismatched with a single mismatched nucleic acid through heat treatment.

Furthermore, the method of detecting a nucleic acid in accordance with the example embodiments has the advantage of enabling a quantitative and direct analysis of a target nucleic acid without denaturation of the nucleic acid.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 6A shows a single-target or multi-target miRNA detection analysis result using a composition for detecting a nucleic acid in an example of the present disclosure.

MODE FOR CARRYING OUT THE INVENTION

Figure 1A:
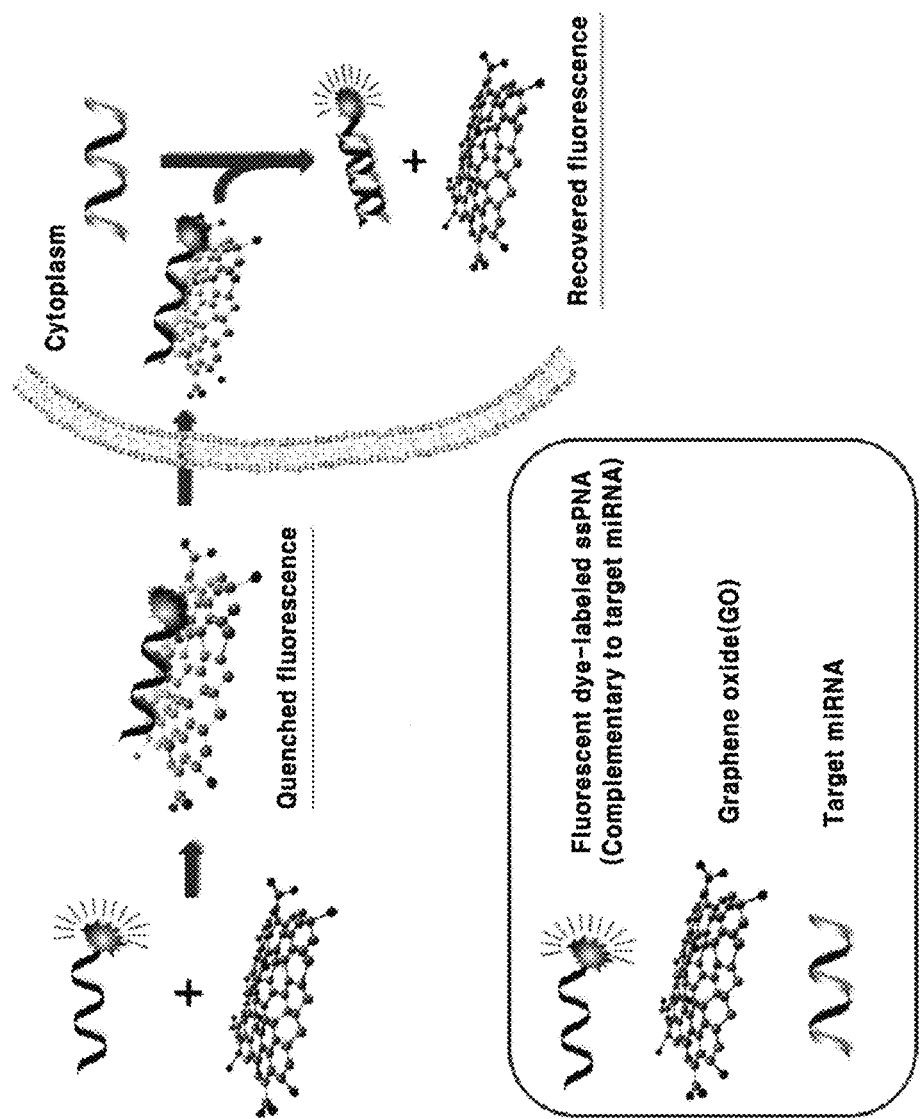
FIG. 1A is a schematic diagram illustrating a method of detecting a nucleic acid in accordance with an embodiment of the present disclosure.

Hereinafter, example embodiments will be described in detail so that inventive concept may be readily implemented by those skilled in the art. However, it is to be noted that the present disclosure is not limited to the example embodiments and examples but can be realized in various other ways. In drawings, parts not directly relevant to the description are omitted to enhance the clarity of the drawings, and like reference numerals denote like parts through the whole document.

Through the whole document, the term "comprises or includes" and/or "comprising or including" used in the document means that one or more other components, steps, operation and/or existence or addition of elements are not excluded in addition to the described components, steps, operation and/or elements unless context dictates otherwise.

The term "about or approximately" or "substantially" are intended to have meanings close to numerical values or ranges specified with an allowable error and intended to prevent accurate or absolute numerical values disclosed for understanding of the present disclosure from being illegally or unfairly used by any unconscionable third party. Through the whole document, the term "step of" does not mean "step for".

Through the whole document, the term "on" that is used to designate a position of one element with respect to another element includes both a case that the one element is adjacent to the another element and a case that any other element exists between these two elements.

Through the whole document, the term "combinations of" included in Markush type description means mixture or combination of one or more components, steps, operations and/or elements selected from the group consisting of components, steps, operation and/or elements described in Markush type and thereby means that the disclosure includes one or more components, steps, operations and/or elements selected from the Markush group.

Through the whole document, the expression "A and/or B" means "A or B, or A and B."

The term "PNA (peptide nucleic acid)" used herein refers to a DNA homologue including polyamide instead of a phosphate backbone.

Hereinafter, various example embodiments and examples will be described in detail with reference to the accompanying drawings.

In accordance with a first aspect of the present disclosure, there is provided a kit for detecting a nucleic acid, including: a graphene oxide; and a PNA probe which includes a fluorescent material and is complementary to a target nucleic acid.

Since a nanosized graphene oxide (nGO) is not harmful to cells, it has biocompatibility and can be introduced into cells through chemical functionalization. Further, the nGO is suitable for signal detection. Various aromatic molecules and bio-materials can be adsorbed to a hydrophobic portion on the surface of the graphene oxide, but not limited thereto. Especially, in case of oligonucleic acid, when oligonucleic acid exists in the form of a single strand, an exposed hydrophobic base of the oligonucleic acid can be adsorbed to the surface of the graphene oxide through $\pi$-$\pi$ interaction. When oligonucleic acid exists in the form of double strands, however, the hydrophobic base would not be exposed to the outside due to hydrogen bonds between the two strands of oligonucleic acid and, thus, would not be adsorbed to the surface of the graphene oxide. By way of example, if a cell is treated with a single-strand nucleic acid probe, which has a complementary sequence to that of a DNA, a RNA or a miRNA having a specific sequence among biomolecular matters and which is adsorbed on graphene oxide, the nucleic acid probes may be combined with a target material, i.e., a DNA, a RNA or a miRNA within the cell in the form of double strands. Accordingly, the nucleic acid may not maintain adsorption to the surface of the graphene oxide and may be separated therefrom.

In accordance with an example embodiment, PNA (Peptide Nucleic Acid) may be used as the oligonucleic acid to be adsorbed to the graphene oxide, but not limited thereto. By way of example, the PNA may be a single-strand PNA and can be easily adsorbed to the surface of the graphene oxide, but not limited thereto. As for the PNA, since a backbone of oligonucleic acid is composed of peptide bonds, PNA is electrically neutral. Accordingly, the PNA has higher adsorbability to hydrophobic graphene oxide than a DNA or RNA which is electrically negative. Further, a PNA-RNA bond is stronger than a DNA-RNA bond or a RNA-RNA bond, and a Tm value of the PNA-RNA bond is higher about 1° C. per a base. Accordingly, a PNA probe has a higher binding force to nucleic acid as a target material than a DNA probe or a RNA probe. Further, since the PNA is very stable against nuclease and protease that exist within a human body, the probability of degradation of the PNA probe is much lower than that of a DNA probe, a RNA probe and a protein probe, when introduced into a cell. Additionally, since the PNA is composed of structurally strong covalent bond, the stability of the PNA can be maintained in a wide pH range under various temperature conditions. Thus, as oligonucleic acid to be used as a probe, the PNA has advantages as compared to other kinds of oligonucleic acids.

In an embodiment, the PNA probe may include a single-stranded PNA complementary to the target nucleic acid, but may not be limited thereto. The PNA refers to a DNA homologue including polyamide instead of a phosphate backbone. The PNA has a high sequence-specificity, and, thus, can be hybridized with a complementary DNA or RNA in a short time. A duplex of a natural nucleic acid and the PNA has high stability in various buffering conditions and at a high temperature, which is mainly caused by an uncharged neutral backbone of the PNA. Generally, a DNA/PNA duplex shows a melting point higher by at least 1° C. per base pair than a DNA duplex. The PNA can interact with a graphene oxide having a stronger negative charge than a nucleic acid and constitute a stable PNA/GO complex which shows a lower background signal caused by less non-specific detachment of a probe nucleic acid from the graphene oxide.

In an embodiment, the graphene oxide and the PNA probe may be included in separated containers respectively, or in a same container together, but may not be limited thereto.

In an embodiment, the kit for detecting the nucleic acid in which the graphene oxide and the PNA probe are included in separated containers respectively may be used by adding the PNA to a sample including the target nucleic acid and then mixing the mixture with the graphene oxide, but may not be limited thereto. Herein, the PNA may be hybridized with the target nucleic acid, and the rest of the PNA which is not hybridized with the target nucleic acid and the rest of nucleic acid strands may be adsorbed on the graphene oxide, and thereby a fluorescent light from a fluorescent material included in the PNA probe adsorbed on the graphene oxide may be quenched, but may not be limited thereto. A free PNA which is not hybridized with the nucleic acid is priorly bonded to the graphene oxide through a $\pi$-$\pi$ stacking interaction and a hydrogen bond formation, and then, a fluorescent light of a dye conjugated to the PNA probe is quenched by energy transfer to the graphene oxide. Accordingly, only a PNA that forms a duplex together with a target DNA generates a fluorescence signal, and, thus, an initial concentration of a double-stranded target DNA can be quantitatively analyzed.

In an embodiment, if the graphene oxide and the PNA are in the same container together, the PNA may be adsorbed on the graphene oxide, and, thus, a fluorescent light from a fluorescent material included in the PNA may be quenched. Then, the target nucleic acid may be added and mixed therewith and thus since the PNA probe may be bonded to the target nucleic acid, the PNA probe may be separated from the graphene oxide and the fluorescent material may emit a fluorescent light, but may not be limited thereto.

A FRET (Fluorescence Resonance Energy Transfer) phenomenon occurs between graphene oxide and organic fluorescent dyes used in accordance with an example embodiment. That is, the graphene oxide, which is an oxidized form of graphene, is capable of quenching a fluorescence signal of adjacent organic fluorescent dyes through FRET. Accordingly, if a PNA probe containing a fluorescent material is adsorbed to the graphene oxide, the fluorescent light of the fluorescent material is quenched. If, however, the PNA probe is hybridized with a DNA, a RNA or a miRNA as a target material and forms double strands, the PNA probe may not be adsorbed to the graphene oxide and separated therefrom. As a result, the fluorescent material contained in the PNA probe would not be subjected to FRET but emit fluorescent light. By measuring the fluorescent light of the sample in this process, the target material in the sample can be detected in real time and can be quantified.

For example, a bond between the nucleic acid as the target material and the PNA probe may be hybridized because the base sequence of the nucleic acid and the base sequence of the PNA probe are complementary, but not limited thereto. By way of example, the base sequence of the PNA probe may have a sequence complementary to a part or the whole of the base sequence of the nucleic acid, but not limited thereto. For example, the PNA probe may have the same length as that of the nucleic acid as the target material and may have a sequence complementary to a part or the whole of the base sequence of the nucleic acid, but not limited thereto. In accordance with an example embodiment, the PNA probe may have a length shorter than that of the nucleic acid as the target material and may have a sequence complementary to a part or the whole of the base sequence of the nucleic acid, but not limited thereto. In accordance with another example embodiment, the PNA probe may have a length longer than that of the nucleic acid as the target material and may have a sequence complementary to a part or the whole of the base sequence of the nucleic acid, but not limited thereto. For example, the complementarity between the base sequence of the PNA probe and the base sequence of the nucleic acid as the target material may be about 70%, about 80%, about 90%, about 95% or about 100%, but not limited thereto. For instance, in case that the nucleic acid as the target material is miRNA, a PNA probe having a complementary sequence to that of the miRNA may include about twenty two (22) bases, but not limited thereto. By way of example, the PNA probe may include one prepared to have a fixed sequence for commercial sales, one prepared to have a sequence designed by a purchaser, or one prepared for noncommercial purposes, but not limited thereto. By way of example, the PNA probe may include one purchased from PANAGENE Inc., but not limited thereto. For example, the PNA probe may include one combined with mature miRNA, but not limited thereto. For instance, the PNA probe may include one combined with miRNA and induces RNA interference to thereby suppress expression or functioning of the miRNA, but not limited thereto.

By way of example, the fluorescent material contained in the PNA probe may be coupled to one end of the PNA probe, or coupled to an inside within the sequence of the PNA probe, but not limited thereto. For example, the fluorescent material contained in the PNA probe may be coupled to a 5'-end or a 3'-end of the PNA probe through covalent bond, and the covalent bond may be forged between the fluorescent material and a linker connected to the 5'-end or 3'end of the PNA probe, but not limited thereto. By way of example, the covalent bond may be forged between an amino group of the linker and the fluorescent material, and the linker may be an ethylene glycol linker, but not limited thereto. By way of more specific example, the linker may be an AEEA linker or an O-linker of PANAGENE Inc., but not limited thereto. For example, the AEEA linker may have a length of about 1.3 nm and include about nine (9) atoms, but not limited thereto.

For example, the fluorescent material contained in the PNA probe may be a fluorescent material that can be applied to a living cell and can measure fluorescent light, but not limited thereto. By way of example, the fluorescent material may be selected from the group consisting of rhodamine and its derivatives, fluorescein and its derivatives, coumarin and its derivatives, acridine and its derivatives, pyrene and its derivatives, erythrosine and its derivatives, eosin and its derivatives, 4-acetamido-4'-isothiocyanatostilbene-2,2'-disulfonic acid, Cy5, Cy3, and combinations thereof, but not limited thereto.

In accordance with an example embodiment, the nucleic acid may include a DNA or RNA, but not limited thereto. By way of example, if the PNA probe containing the fluorescent material is adsorbed on the graphene oxide and introduced into a sample in which a DNA or RNA as a target material exists in the sample, the RNA probe having a complementary sequence to that of the DNA or RNA may be hybridized with the DNA or RNA and turn into a double-stranded nucleic acid. As a result, the PNA probe would be separated from the graphene oxide and the fluorescent material contained in the PNA probe emits fluorescent light without being subjected to FRET (Fluorescence Resonance Energy Transfer). Thus, by measuring the fluorescent light, the DNA or RNA existing in the sample can be detected but not limited thereto. For example, the DNA may include a DNA that encodes protein or a DNA that does not encode protein, but not limited thereto. By way of example, the RNA may include miRNA (messenger RNA), a tRNA (transfer RNA), a rRNA (ribosomal RNA), a s RNA (small RNA), a snRNA (small nuclear RNA), a scRNA (small cytoplasmic RNA), a siRNA (small interfering RNA) or a miRNA (microRNA), but not limited thereto. By way of example, the RNA may include a RNA that is translated into protein, a RNA that is not translated into protein, a 5'-untranslated region, a 3'-untranslated region, or a regulatory RNA, but not limited thereto.

In accordance with an example embodiment, the RNA may include a miRNA, but not limited thereto. By way of example, the miRNA may involve in a biological function in a living body and may be used as a biomarker which is important in diagnosing and curing various diseases such as breast cancer, lung cancer, liver cancer, pancreatic cancer, stomach cancer, colorectal cancer, bone cancer, skin cancer, blood cancer, diabetes and Alzheimer's, or important in predicting prognosis of these diseases, but not limited thereto. By way of example, the miRNA may involve in a lineage specific differentiation in stem cell, but not limited thereto.

In accordance with an example embodiment, the miRNA may include a miRNA-21, a mi-RNA-29a, a miRNA-125b, a miRAN-155 or a miRNA-159, but not limited thereto. The miRNA-21, the miRNA-29a, the mi-RNA-125b or the miRNA-155 may be a miRNA expressed in a human cell, whereas the miRNA-159 may be a miRNA expressed in a plant cell, but not limited thereto. The miRNA-21, the miRNA-29a and the miRNA-125b may be miRNAs expressed in a breast cancer cell, but not limited thereto. For example, the miRNA-21, the miRNA-29a, the miRNA-125b or the miRNA-155 may be a miRNA expressed in a breast cancer cell line MDA-MB-231, MDA-MB-435 or MCF-7 as a model disease cell line, or from various other cancer cells, but not limited thereto.

In accordance with an example embodiment, the PNA probe may have a length of thirty (30) bases or less, but not limited thereto. By way of example, the PNA probe may have a length of about 30 bases or less, from about 5 to about 30 bases, from about 10 to about 30 bases, from about 15 to about 30 bases, from about 20 to about 30 bases, from about 25 to about 30 bases, from about 5 to about 25 bases, from about 5 to about 20 bases, from about 5 to about 15 bases, from about 5 to about 10 bases, or from about 20 to about 25 bases, but not limited thereto. For example, in case that the nucleic acid as a target material is a miRNA, the PNA probe may include about twenty two (22) bases, but not limited thereto.

In accordance with an example embodiment, the graphene oxide may be in the form of a monolayer sheet, but not limited thereto. By way of example, the graphene oxide in the form of the monolayer sheet has a larger surface area than that of graphene oxide which has the same mass but which is not in the form of a monolayer sheet. Thus, even a small quantity of graphene oxide in the form of the monolayer sheet can adsorb a large quantity of nucleic acid probe, but not limited thereto.

In accordance with an example embodiment, the graphene oxide may have a particulate form with a particle size ranging from about 10 nm to about 1 μm, but not limited thereto. By way of example, the graphene oxide may have a particle size in the range from about 10 nm to about 1 μm, from about 10 nm to about 700 nm, from about 10 nm to about 500 nm, from about 10 nm to about 400 nm, from about 10 nm to about 300 nm, from about 10 nm to about 200 nm, from about 10 nm to about 100 nm, from about 10 nm to about 50 nm, from about 50 nm to about 1 μm, from about 100 nm to about 1 μm, from about 200 nm to about 1 μm, from about 300 nm to about 1 μm, from about 400 nm to about 1 μm, from about 500 nm to about 1 μm, from about 700 nm to about 1 μm, from about 200 nm to about 300 nm, or about 400 nm or less, but not limited thereto. For example, due to its microscopic size, the graphene oxide can reach the inside of a cell along with the PNA probe adsorbed on the surface thereof while penetrating a cell membrane easily.

In accordance with an example embodiment, the nucleic acid as the target material may be present in a cell, but not limited thereto. For example, the cell may include a cell being incubated while fixed on a substrate, a cell being incubated while floating in a medium, a cell within a living body, a cell extracted from a living body, or a cell treated for analysis, but not limited thereto. For example, the cell may include a living cell or a dead cell, or may include a cell fixed by a fixing agent, but not limited thereto.

In an embodiment, as the sample including the target nucleic acid, any bio-sample may be used without limitation as long as it can be collected from humans or mammals, and may include, for example, blood, serum, urine, saliva, plasma, or body fluid, but may not be limited thereto.

In accordance with an example embodiment, the nucleic acid as a target material may be detected in real time by measuring the fluorescence of the fluorescent material, but not limited thereto. By way of example, the fluorescence of the fluorescent material may be measured by various methods such as flow cytometry (fluorescence activated cell sorter (FACS)), fluorescence image analysis, and real-time PCR, but not limited thereto. For example, the detection may be performed for a fixed cell, a unfixed cell, a living cell, a dead cell, or a cell processed for detection, but not limited thereto.

In accordance with an example embodiment, the PNA probe may include one or more types of PNA probes containing different kinds of fluorescent materials, respectively, and the nucleic acid as the target material include one or more types of nucleic acids to be combined with the one or more types of PNA probes, respectively. Thus, multiplexed-detection of the different types of nucleic acid can be performed, but not limited thereto. By way of example, the different kinds of fluorescent materials may be fluorescent materials having different colors, but not limited thereto. By way of example, in case that the PNA probe is one or more types of probes containing different kinds of fluorescent materials and the nucleic acid as the target material is one or more types of nucleic acids having complementary sequences to those of the RNA probes, respectively, only a PNA probe having a complementary sequence to that of a nucleic acid existing in a sample would form a double strand and be separated from the graphene oxide, so that fluorescent light would emitted. Accordingly, only a fluorescent material contained in the PNA probe complementary to the nucleic acid existing in the sample would emit fluorescent light. Thus, it can be detected which one of the one or more types of nucleic acids exists in the sample by observing the color of the emitted fluorescent light.

In accordance with a second aspect of the present disclosure, there is provided a method of detecting a nucleic acid, including: a step of mixing a PNA probe with a sample including a target nucleic acid, wherein the PNA probe is adsorbed on a graphene oxide and includes a fluorescent material; and a step of detecting a fluorescent light emitted from the fluorescent material, wherein the target nucleic acid is combined with the PNA probe upon the mixing step so that the PNA probe is separated from the graphene oxide and the fluorescent light is emitted from the fluorescent material.

FIG. 1A is a schematic diagram for describing a method of detecting a nucleic acid in accordance with an example embodiment.

Referring to FIG. 1A, a single-stranded PNA probe contains a fluorescent material and thus can be labeled. The single-stranded PNA probe may be adsorbed on the graphene oxide through a π-π boding between exposed bases of the PNA probe and a hydrophobic surface of the graphene oxide.

At this time, the graphene oxide may incur FREF (Fluorescence Resonance Energy Transfer) and is capable of quenching fluorescent light of the fluorescent material contained in the PNA probe. Accordingly, the PNA probe adsorbed on the graphene oxide does not emit fluorescent light. If the graphene oxide with the PNA probe adsorbed thereon is applied to the sample, the nucleic acid as the target material present in the sample and the single-stranded PNA probe may be hybridized.

Especially, in case that the sample is a cell, due to the microscopic size of the graphene oxide and the presence of the hydrophobic portion on the surface of the graphene oxide, the graphene oxide on which the PNA probe is adsorbed can reach the inside of a cytoplasm through a cell membrane of the cell and can access a nucleic acid as the target material. As a result, the PNA probe adsorbed on the surface of the graphene oxide can be hybridized with the nucleic acid as the target material. If the PNA probe is hybridized with the nucleic acid so as to form double strands, the PNA probe would be separated from the graphene oxide. Accordingly, the fluorescent material contained in the PNA probe would be free from the FRET (Fluorescence Resonance Energy Transfer) phenomenon and may emit fluorescent light. By measuring the fluorescent light, the nucleic acid as the target material present in the sample can be detected and quantified in real time. For example, the fluorescence of the fluorescent material included in the PNA probe may be detected by, but not limited to, a flow cytometer (fluorescence activated cell sorter (FACS)), a fluorescence reader, a qRT-PCR (quantitative real-time PCR), a fluorescence microscope, an in vivo imaging device, or the like. By way of example, the fluorescence reader may be a microplate reader capable of detecting fluorescent light in the range from about 230 nm to about 999 nm, but not limited thereto. For example, the fluorescence reader may be a device configured to select about three types of organic fluorescent dyes to minimize a cross-talk phenomenon between fluorescence signals and observe the fluorescence signals, but not limited thereto. As one example, the flow cytometer may be a device capable of observing a fluorescence signal during flowing a single cell into a tube, but not limited thereto. For instance, the fluorescence microscope may include one capable of observing fluorescence inside or outside a cell or fluorescence of a sample, but not limited thereto. For example, the in vivo imaging device may be Xenogen IVIS 100 produced by Caliper Life Science Inc., but not limited thereto. For more examples, the in vivo imaging device may be a device capable of acquiring an image suitable for each fluorescence wavelength by using a CCD (Charge Coupled Device) camera, but not limited thereto.

In an embodiment, the method of detecting the nucleic acid may further include a step of heat-treating the mixture after the step of mixing the PNA probe adsorbed on the graphene oxide with the sample including the target nucleic acid, but may not be limited thereto. The heat treatment may be performed in a temperature range of from about 50° C. to about 80° C., for example, from about 65° C. to about 70° C., but may not be limited thereto. By way of example, when the heat treatment is performed, the target nucleic acid without a mismatch and the PNA complementary thereto maintain a double strand at a high temperature and are not adsorbed on the graphene oxide, and, thus, a fluorescence signal is maintained. However, a double strand mismatched with a nucleic acid which is mismatched with the PNA, particularly a nucleic acid having only a single mismatch becomes unstable at a high temperature and untangled into single strands. Thus, the single strands are adsorbed on the graphene oxide and then, a fluorescent light is quenched. Therefore, it is possible to provide the method of detecting the nucleic acid capable of distinguishing a single mismatch.

In an embodiment, the PNA probe may include a single-stranded PNA complementary to the target nucleic acid, but may not be limited thereto. The PNA refers to a DNA homologue including polyamide instead of a phosphate backbone. The PNA has a high sequence-specificity, and, thus, can be hybridized with a complementary DNA or RNA in a short time. A duplex of a natural nucleic acid and the PNA has high stability in various buffering conditions and at a high temperature, which is mainly caused by an uncharged neutral backbone of the PNA. Generally, a DNA/PNA duplex shows a melting point higher by at least 1° C. per base pair than a DNA duplex. The PNA can interact with a graphene oxide having a stronger negative charge than a nucleic acid and constitute a stable PNA/GO complex which shows a lower background signal caused by less non-specific detachment of a probe nucleic acid from the graphene oxide.

In accordance with an example embodiment, the nucleic acid may include a DNA or RNA, but not limited thereto. By way of example, if the PNA probe containing the fluorescent material is adsorbed on the graphene oxide and introduced into a sample in which a DNA or RNA as a target material exists in the sample, the RNA probe having a complementary sequence to that of the DNA or RNA may be hybridized with the DNA or RNA and turn into a double-stranded nucleic acid. As a result, the PNA probe would be separated from the graphene oxide and the fluorescent material contained in the PNA probe emits fluorescent light without being subjected to FRET (Fluorescence Resonance Energy Transfer). Thus, by measuring the fluorescent light, the DNA or RNA existing in the sample can be detected but not limited thereto. For example, the DNA may include a DNA that encodes protein or a DNA that does not encode protein, but not limited thereto. By way of example, the RNA may include miRNA (messenger RNA), a tRNA (transfer RNA), a rRNA (ribosomal RNA), a s RNA (small RNA), a snRNA (small nuclear RNA), a scRNA (small cytoplasmic RNA), a siRNA (small interfering RNA) or a miRNA (microRNA), but not limited thereto. By way of example, the RNA may include a RNA that is translated into protein, a RNA that is not translated into protein, a 5'-untranslated region, a 3'-untranslated region, or a regulatory RNA, but not limited thereto.

In accordance with an example embodiment, the RNA may include a miRNA, but not limited thereto. By way of example, the miRNA may involve in a biological function in a living body and may be used as a biomarker which is important in diagnosing and curing various diseases such as breast cancer, lung cancer, liver cancer, pancreatic cancer, stomach cancer, colorectal cancer, bone cancer, skin cancer, blood cancer, diabetes and Alzheimer's, or important in predicting prognosis of these diseases, but not limited thereto. By way of example, the miRNA may involve in a lineage specific differentiation in stem cell, but not limited thereto.

In accordance with an example embodiment, the miRNA may include a miRNA-21, a mi-RNA-29a, a miRNA-125b, a miRAN-155 or a miRNA-159, but not limited thereto. The miRNA-21, the miRNA-29a, the mi-RNA-125b or the miRNA-155 may be a miRNA expressed in a human cell, whereas the miRNA-159 may be a miRNA expressed in a plant cell, but not limited thereto. The miRNA-21, the miRNA-29a and the miRNA-125b may be miRNAs expressed in a breast cancer cell, but not limited thereto. For example, the miRNA-21, the miRNA-29a, the miRNA-125b or the miRNA-155 may be a miRNA expressed in a breast cancer cell line MDA-MB-231, MDA-MB-435 or MCF-7 as a model disease cell line, or from various other cancer cells, but not limited thereto.

In accordance with an example embodiment, the PNA probe may have a length of thirty (30) bases or less, but not limited thereto. By way of example, the PNA probe may have a length of about 30 bases or less, from about 5 to about 30 bases, from about 10 to about 30 bases, from about 15 to about 30 bases, from about 20 to about 30 bases, from about 25 to about 30 bases, from about 5 to about 25 bases, from about 5 to about 20 bases, from about 5 to about 15 bases, from about 5 to about 10 bases, or from about 20 to about 25 bases, but not limited thereto. For example, in case that the nucleic acid as a target material is a miRNA, the PNA probe may include about twenty two (22) bases, but not limited thereto.

In accordance with an example embodiment, the graphene oxide may be in the form of a monolayer sheet, but not limited thereto. By way of example, the graphene oxide in the form of the monolayer sheet has a larger surface area than that of graphene oxide which has the same mass but which is not in the form of a monolayer sheet. Thus, even a small quantity of graphene oxide in the form of the monolayer sheet can adsorb a large quantity of nucleic acid probe, but not limited thereto.

In accordance with an example embodiment, the graphene oxide may have a particulate form with a particle size ranging from about 10 nm to about 1 μm, but not limited thereto. By way of example, the graphene oxide may have a particle size in the range from about 10 nm to about 1 μm, from about 10 nm to about 700 nm, from about 10 nm to about 500 nm, from about 10 nm to about 400 nm, from about 10 nm to about 300 nm, from about 10 nm to about 200 nm, from about 10 nm to about 100 nm, from about 10 nm to about 50 nm, from about 50 nm to about 1 μm, from about 100 nm to about 1 μm, from about 200 nm to about 1 μm, from about 300 nm to about 1 μm, from about 400 nm to about 1 μm, from about 500 nm to about 1 μm, from about 700 nm to about 1 μm, from about 200 nm to about 300 nm, or about 400 nm or less, but not limited thereto. For example, due to its microscopic size, the graphene oxide can reach the inside of a cell along with the PNA probe adsorbed on the surface thereof while penetrating a cell membrane easily.

In accordance with an example embodiment, the sample may include a cell, but not limited thereto. For example, the cell may include a cell being incubated while fixed on a substrate, a cell being incubated while floating in a medium, a cell within a living body, a cell extracted from a living body, or a cell treated for analysis, but not limited thereto. For example, the cell may include a living cell or a dead cell, or may include a cell fixed by a fixing agent, but not limited thereto.

In an embodiment, as the sample including the target nucleic acid, any bio-sample may be used without limitation as long as it can be collected from humans or mammals, and may include, for example, blood, serum, urine, saliva, plasma, or body fluid, but may not be limited thereto.

In accordance with an example embodiment, the nucleic acid as a target material in the sample may be detected in real time by measuring the fluorescence of the fluorescent material in real time. By way of example, the fluorescence of the fluorescent material may be measured by various methods such as flow cytometry [fluorescence activated cell sorter (FACS)], fluorescence image analysis, and real-time PCR, but not limited thereto. For example, the detection may be performed for a fixed cell, a unfixed cell, a living cell, a dead cell, or a cell processed for detection, but not limited thereto.

In accordance with an example embodiment, the PNA probe may include one or more types of PNA probes containing different kinds of fluorescent materials, respectively, and the nucleic acid as the target material include one or more types of nucleic acids to be combined with the one or more types of PNA probes, respectively. Thus, multiplexed-detection of the different types of nucleic acid can be performed, but not limited thereto. By way of example, the different kinds of fluorescent materials may be fluorescent materials having different colors, but not limited thereto. By way of example, in case that the PNA probe is one or more types of probes containing different kinds of fluorescent materials and the nucleic acid as the target material is one or more types of nucleic acids having complementary sequences to those of the RNA probes, respectively, only a PNA probe having a complementary sequence to that of a nucleic acid existing in a sample would form a double strand and be separated from the graphene oxide, so that fluorescent light would emitted. Accordingly, only a fluorescent material contained in the PNA probe complementary to the nucleic acid existing in the sample would emit fluorescent light. Thus, it can be detected which one of the one or more types of nucleic acids exists in the sample by observing the color of the emitted fluorescent light.

In accordance with a third aspect of the present disclosure, there is provided a method of detecting a nucleic acid, including: a step of mixing a PNA probe with a sample including a target nucleic acid, wherein the PNA probe includes a fluorescent material and is complementary to the target nucleic acid; a step of adding a graphene oxide into the mixture; and a step of detecting quenching of the fluorescent light from the fluorescent material, wherein the rest of the PNA probe which is not hybridized with the target nucleic acid and the rest of the nucleic acid are adsorbed on the graphene oxide and thereby the fluorescent light from the fluorescent material is quenched.

Figure 12:
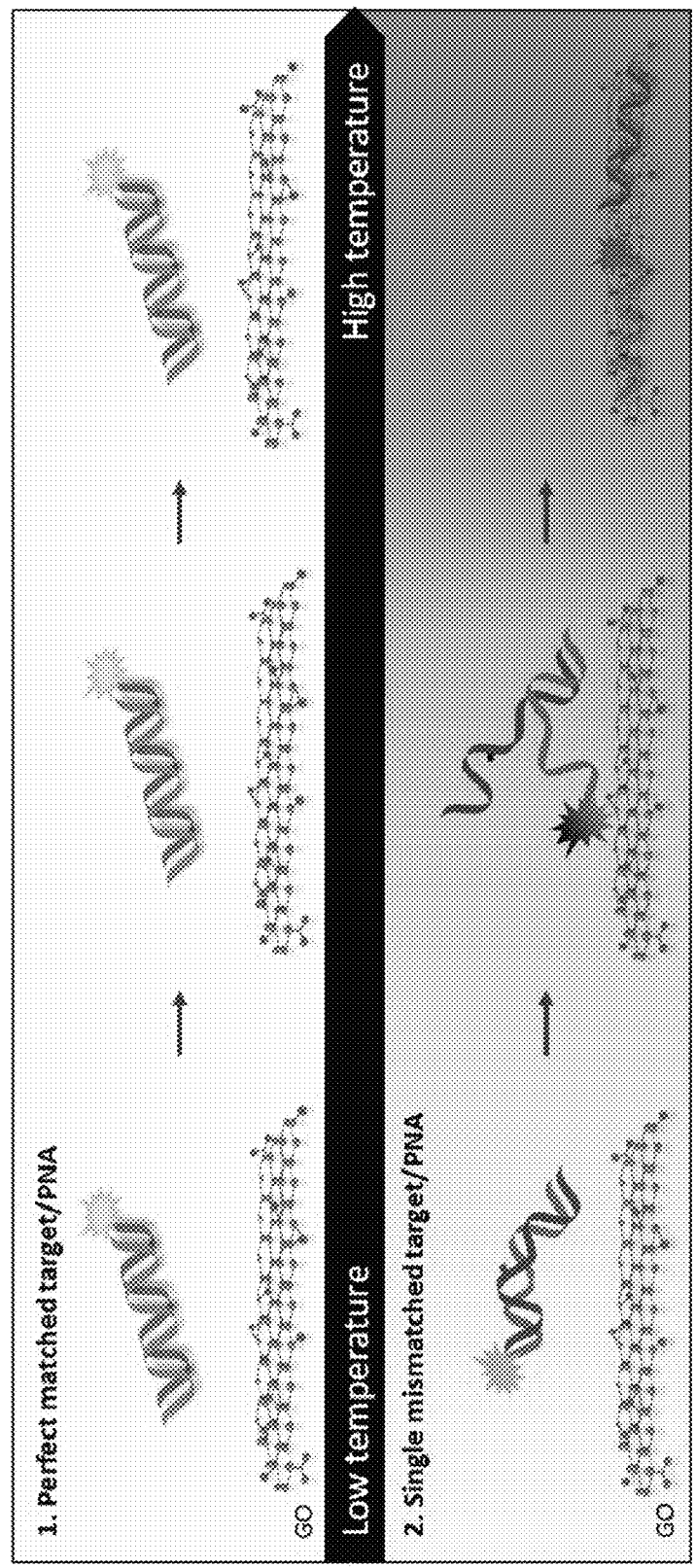
FIG. 12 is a diagram schematically illustrating a mechanism of a method of detecting a target nucleic acid in accordance with an embodiment of the present disclosure.

In an embodiment, the method of detecting the nucleic acid may further include a step of heat-treating the mixture after the step of adding the graphene oxide into the mixture, but may not be limited thereto. The heat treatment may be performed in a temperature range of from about 50° C. to about 80° C., for example, from about 65° C. to about 70° C., but may not be limited thereto. By way of example, when the heat treatment is performed at about 70° C., the target nucleic acid without a mismatch and the PNA complementary thereto maintain a double strand at a high temperature and are not adsorbed on the graphene oxide, and, thus, a fluorescence signal is maintained ((a) of FIG. 12). However, a double strand mismatched with a nucleic acid which is mismatched with the PNA, particularly a nucleic acid having only a single mismatch becomes unstable at a high temperature and untangled into single strands. Thus, the single strands are adsorbed on the graphene oxide and then, a fluorescent light is quenched ((b) of FIG. 12). Therefore, it is possible to provide the method of detecting the nucleic acid capable of distinguishing a single mismatch.

Figure 1B:
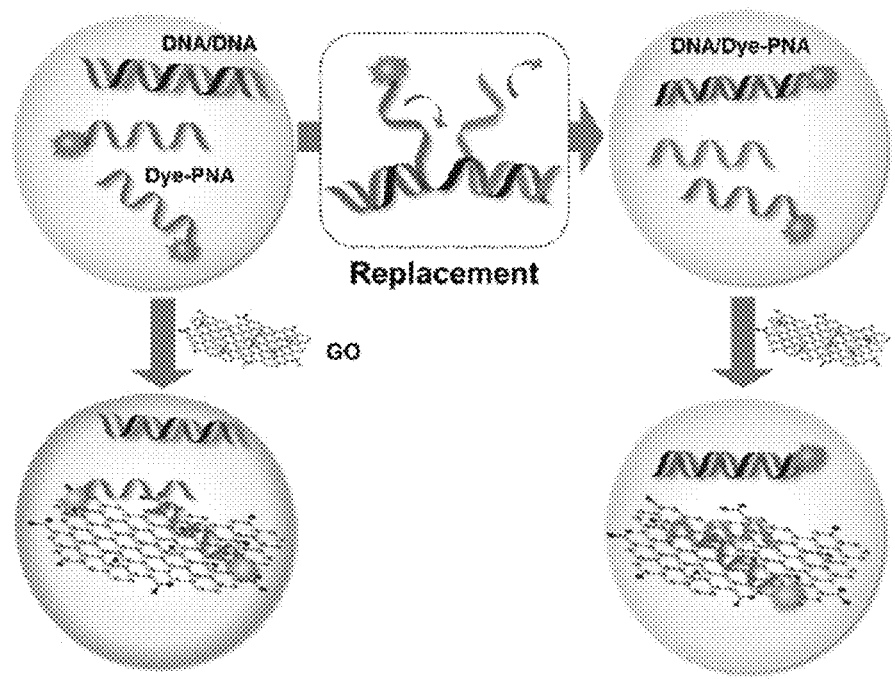
FIG. 1B is a schematic diagram illustrating a mechanism of a method of detecting a nucleic acid in accordance with an embodiment of the present disclosure.

FIG. 1B is a schematic diagram illustrating a mechanism of a method of detecting a nucleic acid in accordance with the present disclosure.

Referring to FIG. 1B, firstly, a PNA probe conjugated to a fluorescent dye (Dye-probe) and a double-stranded target DNA including an upper strand as an actual target DNA for recognizing the PNA probe and a lower strand complementary to the target DNA are prepared. If the PNA probe and the double-stranded DNA are incubated together, a base pair at termini of a DNA duplex has a weaker hydrogen bond than a base pair within the DNA duplex. Thus, the PNA can be bonded to termini of the upper strand. Then, branch migration for strand displacement occurs gradationally due to high binding affinity of the PNA with respect to its complementary DNA. Finally, the lower strand is separated from the original DNA duplex, so that a PNA/DNA duplex may be formed. When a graphene oxide (GO) is added to the mixture, a free PNA probe instead of the PNA/DNA duplex may be priory bonded to the graphene oxide through a π-π stacking interaction and a hydrogen bond formation, and then, a fluorescent light of the dye conjugated to the PNA probe may be quenched by energy transfer to the graphene oxide. Accordingly, only a PNA that forms a duplex together with a target DNA generates a fluorescence signal, and, thus, an initial concentration of the double-stranded target DNA can be quantitatively analyzed (see FIG. 1B).

Hereinafter, the redundant descriptions with respect to the third aspect of the present disclosure will be omitted. All the above descriptions regarding the first aspect and the second aspect of the present disclosure can also be applied to the third aspect.

Below, examples of the embodiments will be described. However, the following examples are intended to facilitate understanding of the present disclosure and therefore are not intended to limit its scope.

EXAMPLES

Preparation Example 1

Preparation and Characterization of Graphene Oxide

In an example, a graphene oxide sheet was prepared according to the modified Hummer's method which is commonly known in the pertinent art. First, 0.5 g of $NaNO_3$ (produced by Junsei Co., (Japan)) and 23 mL of $H_2SO_4$ (produced by Samchun Chemical Co., (Seoul, Korea) were mixed while being intensely agitated within a water tub filled with ice. Then, 3 g of $KMnO_4$ (produced by Sigma-Aldrich Co., (Missouri, USA) was slowly added to the mixture. After the $KMnO_4$ is added, the solution was moved into an ice bath at a temperature of 35° C. and agitated therein for 1 hour. Then, 40 mL of distilled water was added, and the temperature of the water tub was raised to 90° C. for 30 minutes. Then, 100 mL of distilled water was added again. Thereafter, by adding 3 mL of 30% $H_2O_2$ (produced by Junsei Co., (Japan)) in drops, the color of the solution was changed from dark brown to yellow. Then, the synthesized graphene oxide solution was filtered through a Buchner funnel and washed with distilled water at least four times. Filtered sediments were dried in desiccators and re-dispersed into the distilled water. Thereafter, the solution in which the graphene oxide was dispersed was ultrasonicated for four hours, so that nano-size graphene oxide was obtained. The size of the graphene oxide obtained at this time was in the range from about 0.05 nm to about 300 nm, and this graphene oxide was stored and used in a concentration of 1 mg/mL.

Figure 2A:
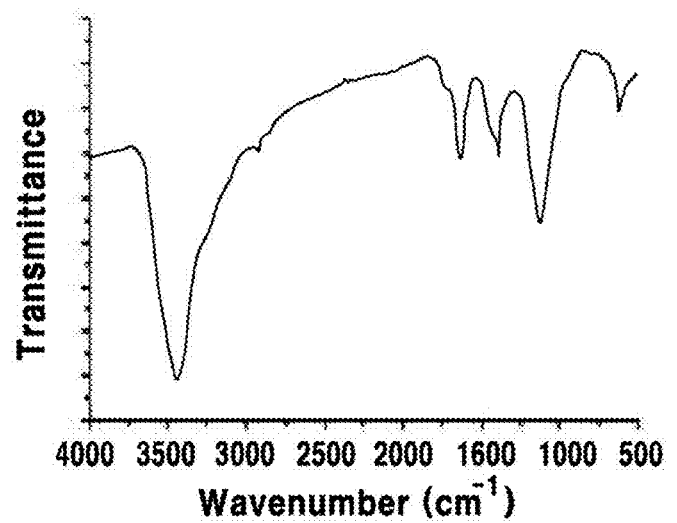
FIG. 2A provides an analysis result of ultraviolet-visible (UV-vis) spectrum of graphene oxide in an example of the present disclosure.
Figure 2A:
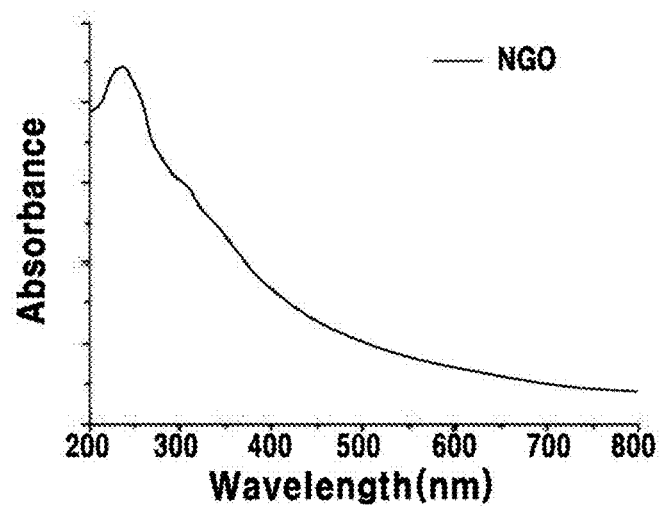
Figure 2A:
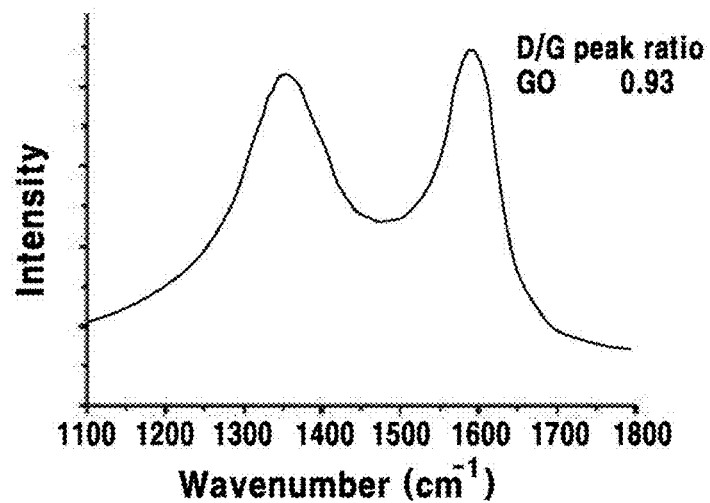
Figure 2B:
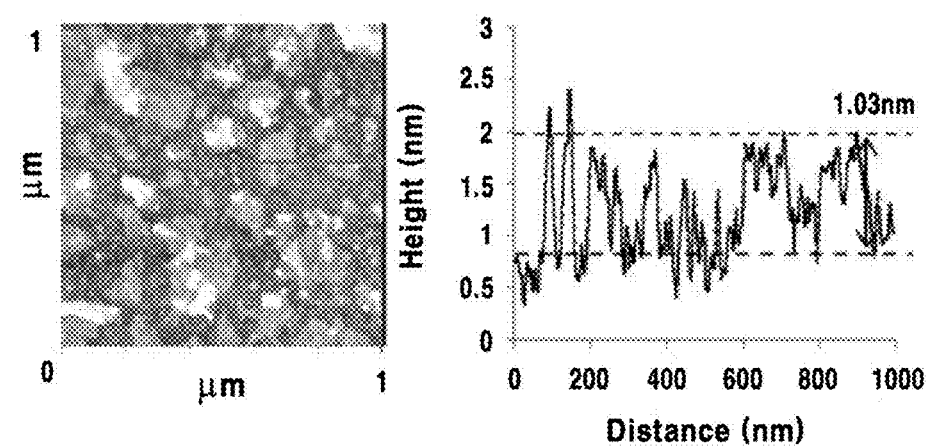
FIG. 2B provides an analysis result of a chemical structure of the graphene oxide in an example of the present disclosure.

The graphene oxide prepared according to the above method was analyzed by using atomic force microscopy (AFM) and it was confirmed that this graphene oxide is in the form of a monolayer sheet. As for a size and a thickness of the sheet, the sheet has a width of from 0.05 nm to 300 nm and a height of 1.03 nm. Further, ultraviolet-visible (UV-vis) spectrum of the graphene oxide was investigated, and an absorbance peak was observed, as well-known in the art, at 230 nm, as depicted in FIG. 2A. A chemical structure of the graphene oxide was investigated by using infrared ray and Raman spectrum, and the result is shown in FIG. 2B. Functional groups combined with the graphene oxide were found to be alcohol (3,415 $cm^{-1}$, 1,040 $cm^{-1}$), epoxy (1,079 $cm^{-1}$), carboxyl (1,716 $cm^{-1}$), oxidized sp2 carbon (1,627 $cm^{-1}$), and so forth. In view of a decrease of a relative intensity of the carboxyl group in the nano-graphene oxide preparation process, it was deemed that a reduction reaction had occurred slightly. Further, as a result of zeta-potential measurement in which surface charges were measured, a negative value of −17.9 mV was observed. As proved from these data, the graphene oxide mono-layer sheet was prepared successfully.

Preparation Example 2

Adsorption of a Single-Stranded PNA Probe to Graphene Oxide and Observation of Resultant Fluorescence Quenching Sequences of miRNAs and complementary sequences of PNA probes used in the present preparation example and all of the following examples are specified in Table 1 as bellows.

TABLE 1

| Target miRNA | Base Sequence of miRNA | Base Sequence of Fluorescence-labeled Probe | Organism |
|---|---|---|---|
| miRNA-21 | SEQ ID NO. 24:<br>UAGCUUAUCAGACUGAUGUUGA | SEQ ID NO. 25:<br>FAM-OO-<br>TCAACATCAGTCTGATAAGCTA | Human |
| miRNA-125b | SEQ ID NO. 26:<br>UCCCUGAGACCCUAACUUGUGA | SEQ ID NO. 27:<br>ROX-OO-<br>TCACAAGTTAGGGTCTCAGGGA | Human |
| miRNA-155 | SEQ ID NO. 28:<br>UUAAUGCUAAUCGUGAUAGGGGU | SEQ ID NO. 29:<br>Cy5-OO-<br>CTATCACGATTAGCATTA | Human |
| miRNA-159 | SEQ ID NO. 30:<br>UUUGGAUUGAAGGGAGCUCUA | SEQ ID NO. 31:<br>FAM-OO-<br>TAGAGCTCCCTTCAATCCAAA | Plant |
| miRNA-29a | SEQ ID NO. 32:<br>UAGCACCAUCUGAAAUCGGUUA | SEQ ID NO. 33:<br>FAM-OO-<br>TAACCGATTTCAGATGGTGCTA | Human |

In the above table, the left sequences of nucleic acids are base sequences of miRNAs, whereas the right sequences of nucleic acids are base sequences of PNA probes that are complementary to the respective base sequences of the miRNAs. The miRNA-159 was used as a negative control group. The miRNA used in this example include a miRNA-21, a miRNA-29a, a miRNA-125b and a miRNA-155 that are known to be expressed in several cancer cells including breast cancer.

In this preparation example, three kinds of single-stranded PNA probes labeled with organic fluorescent dyes FAM, ROX and Cy5, respectively, were dissolved in nuclease-free water of which the concentration of single-stranded PNA is 100 µM. Selected as the three kinds of PNA probes, a miRNA-21, a miRNA-125b and a miRNA-155 were showing different expression patterns on breast cancer cell lines (MDA-MB-231, MDA-MB-435, and MCF-7) as model disease cell lines. At this time, in consideration of an in vivo experiment as well as an in vitro experiment, the PNA probes were dissolved in the nuclease-free water. Further, since the solubility of the PNA probes would be different depending on their base sequences, lengths, and the like, the PNA probes were dissolved after being heated at a temperature of from about 60° C. to 70° C. for about 10 minutes. Then, the PNA solutions were divided into each amount of usage and stored in a cold storage while wrapped in foil. Whenever each PNA solution is used, it was heated at the temperature of from about 60° C. to 70° C. for about 10 minutes, as mentioned above. Then, the fluorescence-labeled PNA probes were mixed with the nano-size graphene oxide, respectively (such that the graphene oxide which was prepared to have a concentration of from 0.5 mg/mL to 1 mg/mL reached a concentration of from 0.05 mg/mL to 0.1 mg/mL). When mixing each fluorescence-labeled PNA probe and the graphene oxide, a buffer (250 mM Tris, pH 7.4 (Fisher Co.,)) enriched to five times was added to the PNA probe and the graphene oxide in proportion to the total volume of each solution, and the rest volume was filled with the nuclease-free water.

As a result of mixing the fluorescence-labeled PNA probes and the graphene oxide, it was observed that from about 190 pmol to about 200 pmol of FAM-PNA-21 (PNA probe containing a FAM fluorescent material and complementary to the miRNA-21) could be adsorbed to each 1 µg of nano-size graphene oxide (nGO); about 135 pmol of ROX-PNA-125b (PNA probe containing a ROX fluorescent material and complementary to the miRNA-125b) could be adsorbed to each 1 µg of nano-size graphene oxide (nGO); and about 180 pmol of Cy5-PNA-155 (PNA probe containing a Cy5 fluorescent material and complementary to the miRNA-155) could be adsorbed to each 1 µg of nano-size graphene oxide (nGO).

Figure 3:
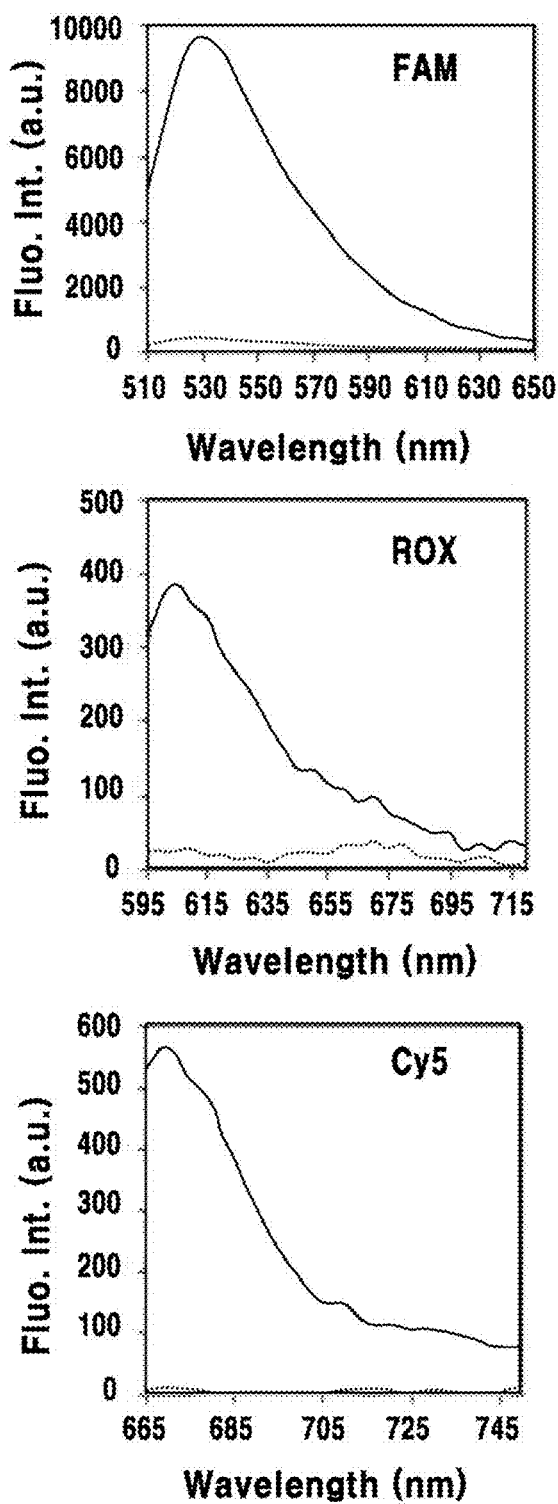
FIG. 3 is a graph showing adsorption of a PNA probe to graphene oxide and occurrence or non-occurrence of fluorescence quenching in an example of the present disclosure.

Then, fluorescence in each case was analyzed by using a fluorescence reader (Biotek Synergy MX). As depicted in FIG. 3, a fluorescence signal of FAM, a fluorescence signal of ROX and a fluorescence signal of Cy5 exhibited the highest fluorescence peak at ex/em=488/530 nm, ex/em=575/610 nm and ex/em=643/670 nm; respectively. In the present example, the fluorescence was observed with the spectrum in this range. Here, if the fluorescence signal of each probe when the probe is not mixed with the graphene oxide is set as 100%, it is deemed to be optimal when the fluorescence signal quenched and decreased to about 4% of the original signal. When the graphene oxide and the FAM-PNA-21, the ROX-PNA-12.5b or the Cy5-PNA-155 were mixed, it was confirmed through fluorescence observation that the fluorescence signal of the PNA probe quenched effectively at a room temperature in about 10 minutes.

Example 1

Evaluation of Oligonucleic Acid Containing a Fluorescent Material, for Detecting miRNA as a Target Material Numerous biomolecules exist in a cell. Therefore, in case of graphene oxide having high adsorbability for nonspecific biomolecules, non-specific desorption of a probe may be occur even under the absence of a nucleic acid as a target material, thus emitting a fluorescence signal. In view of this, in the present example, miRNA detection efficiencies of a PNA probe or DNA probe having a base sequence complementary to that of a target miRNA were compared to investigate whether the PNA probe is more suitable than the DNA probe.

Cells of MDA-MB-231 expressing the miRNA-21 as one of breast cancer cell lines selected as a model disease cell line were collected, and a cytolysate was acquired by repeating freezing an defrosting of the cells. A DNA or PNA probe complementary to the miRNA-21 was used while labeling the DNA or PNA probe with an organic fluorescent dye FAM.

Figure 4:
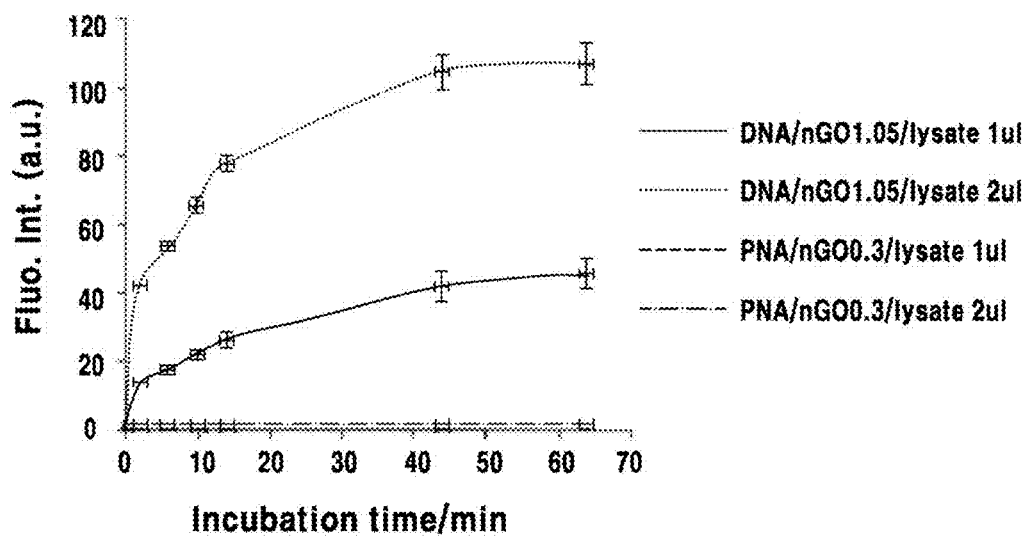
FIG. 4 is a graph for the comparison of a quenching phenomenon of a PNA probe and a quenching phenomenon of a DNA probe in an example of the present disclosure.
Figure 4:
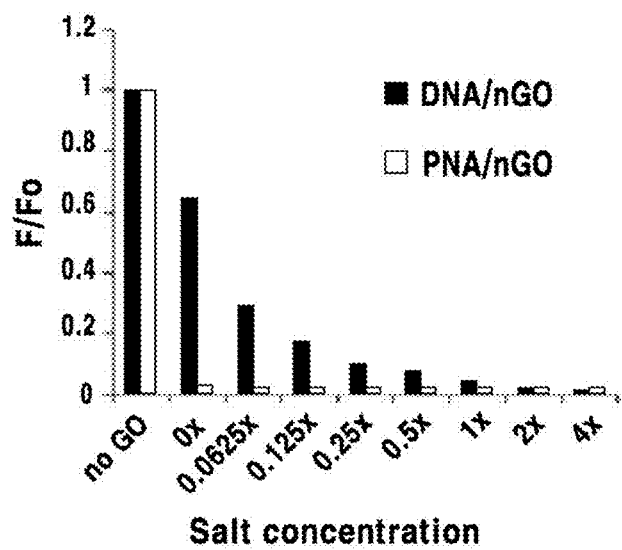

A buffered hypotonic solution (20 mM of HEPES (pH 8.0), 2 mM of $MgCl_2$, 0.2 mM of EGTA, 10% of glycerol and 1 mM of dethiothreitol, and 1 mM of DTT was added immediately before used) for cell lysis was prepared, and a hundred thousand (100,000) cells were in 100 L of the buffered solution. Then, by repeating freezing and defrosting of the cell-containing solution about three times by subjecting the cell-containing solution to liquid nitrogen (temperature of about −196° C.) and a temperature of 37° C. alternately, the cells were broken down and cell lysate was obtained. Then, 15 µL of 3M NaCl was added to 100 µL of the obtained lysate, and a final NaCl concentration was set to 4 M. Thereafter, the mixture was centrifugated at a 12,000 rpm by a centrifuge of 4° C. for about 20 minutes. A supernatant was moved into a new storage tube and used in an experiment. Each of a DNA probe and a PNA probe (FAM-PNA-21) complementary to the miRNA-21 was adsorbed on graphene oxide, and the DNA and PNA probes adsorbed on the graphene oxide were subjected to experiment while mixed with the cell lysate. In the present example, the degree of fluorescence quenching of the fluorescent light labeled in the probe, which depends on a variation in the concentration of a salt was tested. As shown in FIG. 4, the DNA probe showed a variation in the degree of fluorescence quenching depending on a variation in the concentration of the salt. Unlike the DNA probe, however, the PNA probe showed a constant degree of quenching regardless of the salt concentration. Further, in the process of cell lysis by repeating the freezing and defrosting of the cells, it was confirmed that after mixed with the cell lysate in which most RNAs were decomposed and no more existed, the DNA probe was easily separated from the graphene oxide and fluorescence dequenched, whereas the PNA probe was stably adsorbed on the graphene oxide and maintain the fluorescence quenching state. That is, it is deemed that the DNA probe adsorbed on the graphene oxide would be easily separated from the graphene oxide even under the absence of a miRNA as a target, unlike the PNA probe. Thus, it was proved that the PNA probe can be adsorbed on the graphene oxide more stable than the DNA probe.

Example 2

Figure 5A:
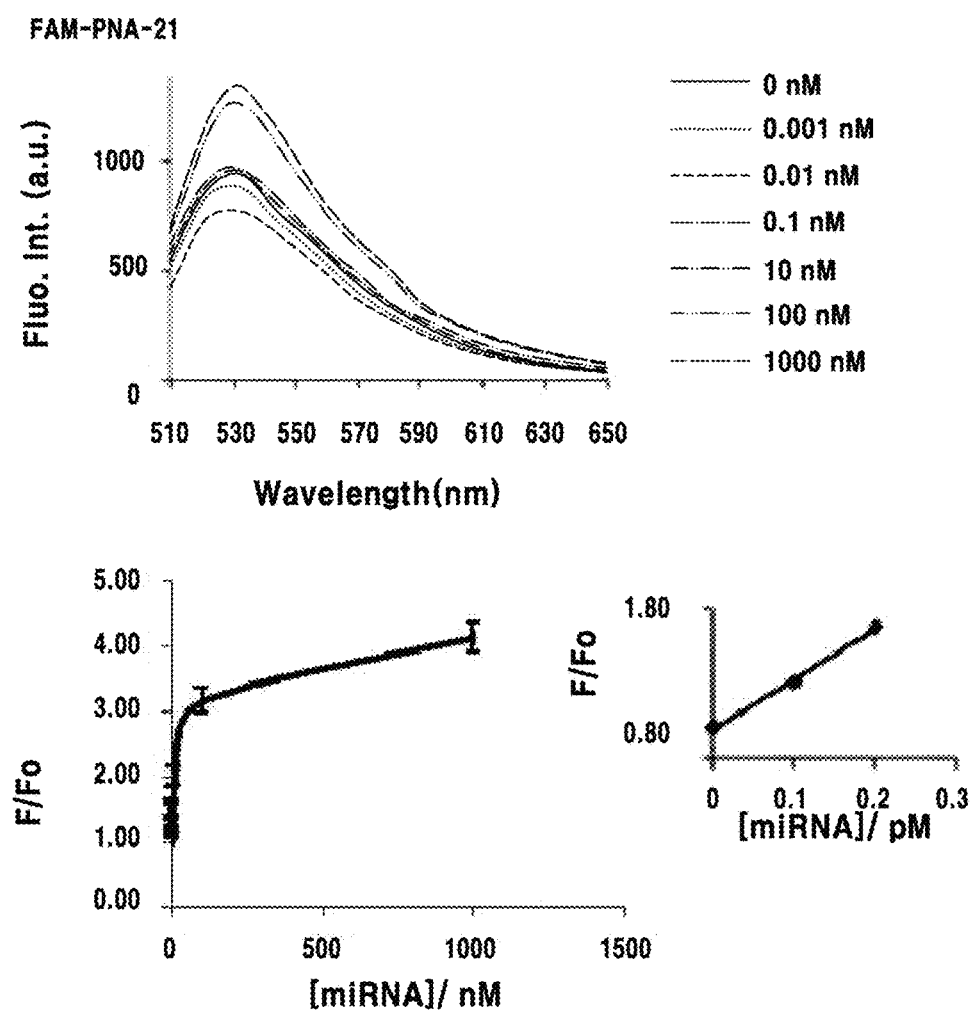
FIG. 5A is a graph showing a measurement of sensitivity of a PNA probe to a miRNA in an example of the present disclosure.
Figure 5B:
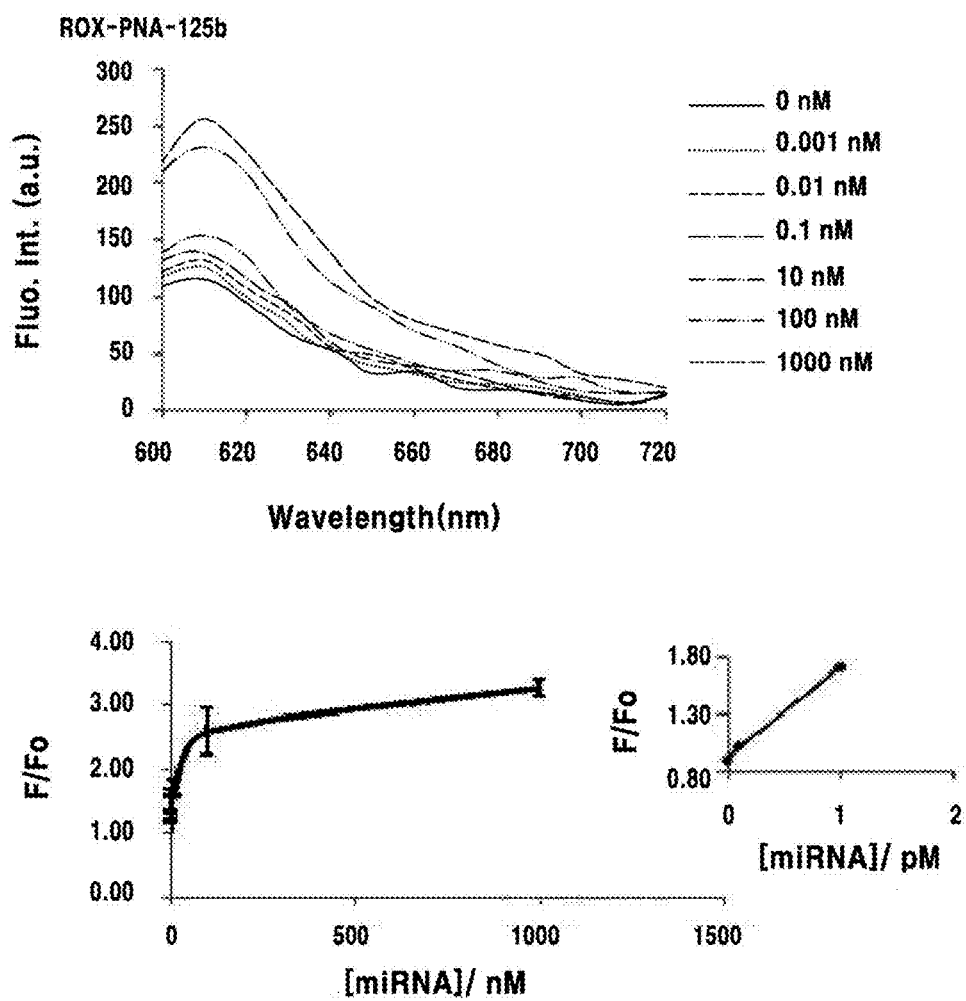
FIG. 5B is a graph showing a measurement of sensitivity of a PNA probe to a miRNA in an example of the present disclosure.
Figure 5C:
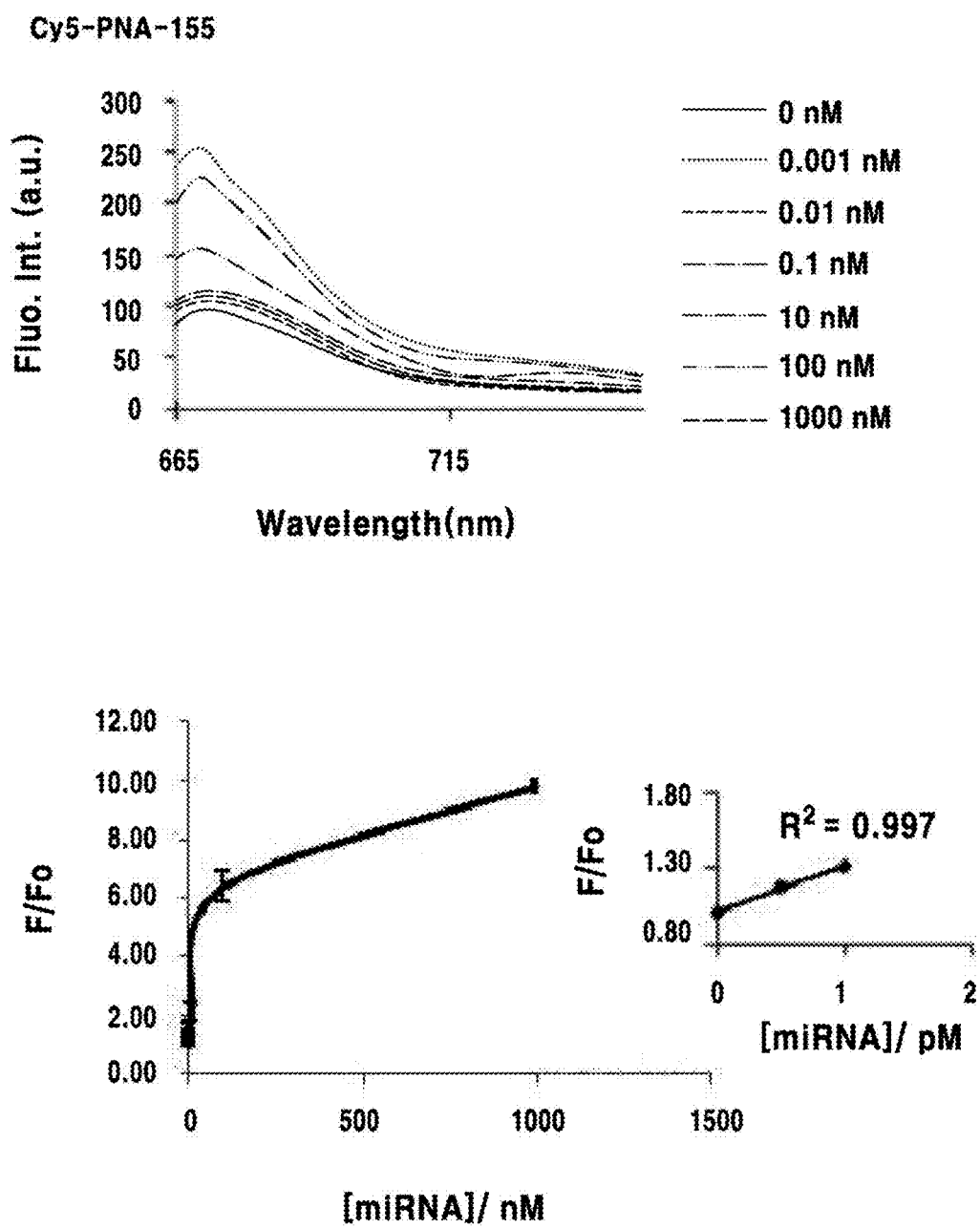
FIG. 5C is a graph showing a measurement of sensitivity of a PNA probe to a miRNA in an example of the present disclosure.

Evaluation of Detection Sensitivity of PNA Probes for a miRNA as a Target Material A total quantity of RNAs present in a single cell may be about 15 pg, and miRNAs exist therein in a much smaller quantity. Thus, detection sensitivity for a miRNA as a target material was evaluated in this example. The detection sensitivity of a PNA probe for a miRNA-21, a miRNA-125b or a miRNA-155 was evaluated as follows. A solution prepare by adsorbing a fluorescence-labeled PNA probe to 1 µg of nano-size graphene oxide was synthesized with a miRNA (produced by Pioneer Co.,) as a target material. Specifically, the miRNA was added in an amount of 0 mN, 0.001 nM, 0.01 nm, 0.1 nM, 1 nM, 10 nM, 100 nM or 1,000 nM and left at a room temperature for about 10 minutes. Then, fluorescence of a fluorescent material expressed at each probe was measured. As a result of measuring a variation in the fluorescence before and after adding the miRNA as the target material, a miRNA having a concentration in the range from about 0.1 pM to about 1 pM was detected in experiments using the three kinds of PNA probes, as depicted in FIG. 5A to FIG. 5C, though the amounts of the PNA probes adsorbed on the nano-size graphene oxide having a unitary quantity of 1 μg were different.

Example 3

Detection of a Single-Target miRNA or Multi-Target miRNAs Present in a Sample

Figure 6B:
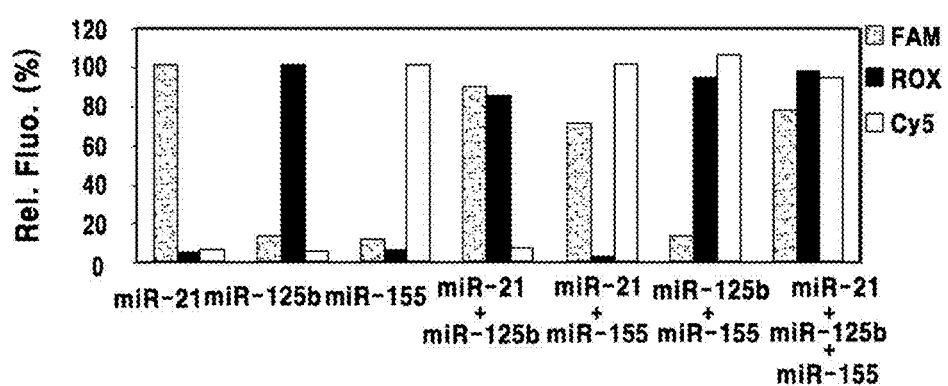
FIG. 6B shows a single-target or multi-target miRNA detection analysis result using a composition for detecting a nucleic acid in an example of the present disclosure.
Figure 6C:
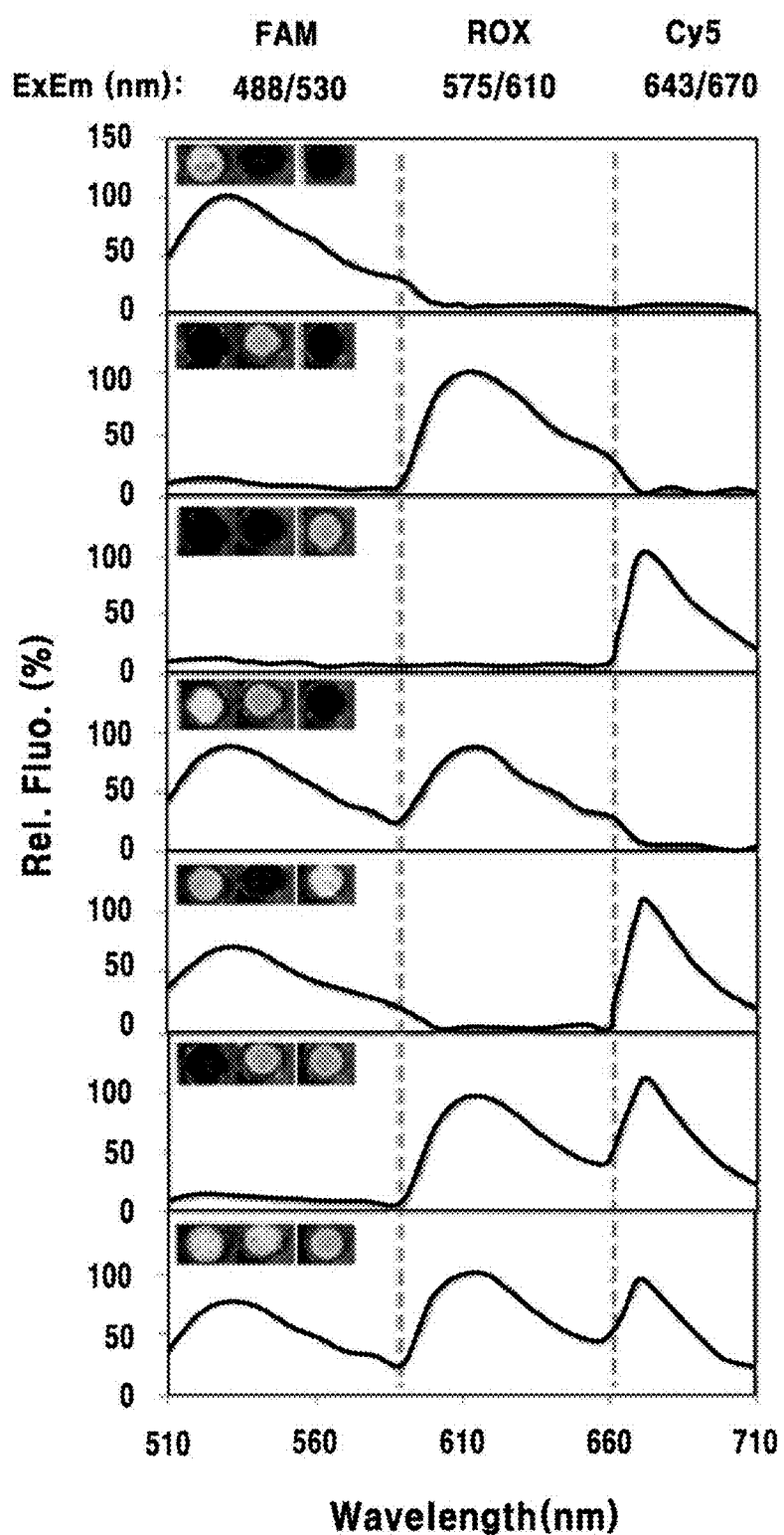
FIG. 6C shows a single-target or multi-target miRNA detection analysis result using a composition for detecting nucleic acid in an example of the present disclosure.
Figure 7A:
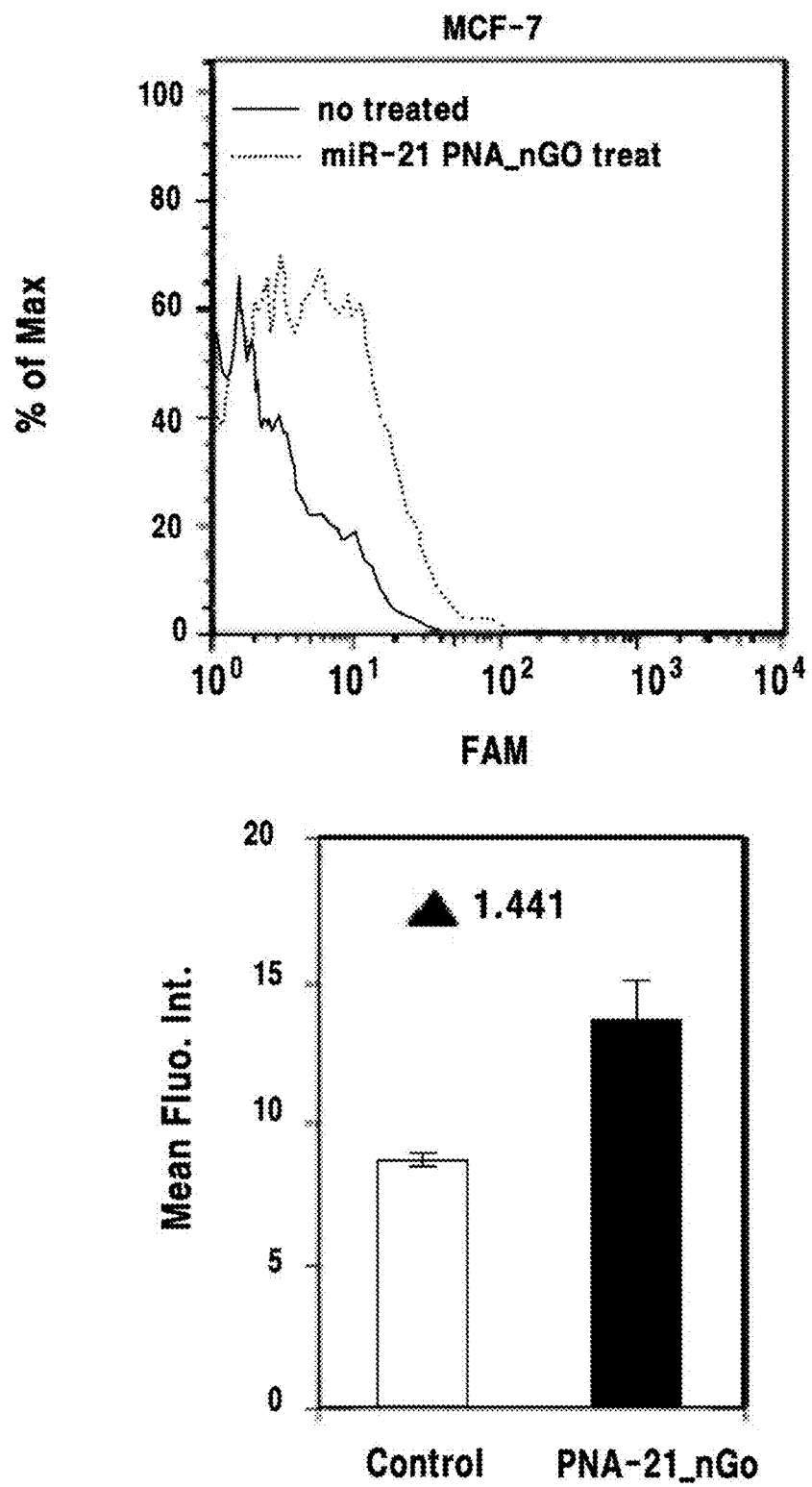
FIG. 7A shows an intracellular single-target miRNA detection analysis result using a composition for detecting a nucleic acid in an example of the present disclosure.
Figure 7B:
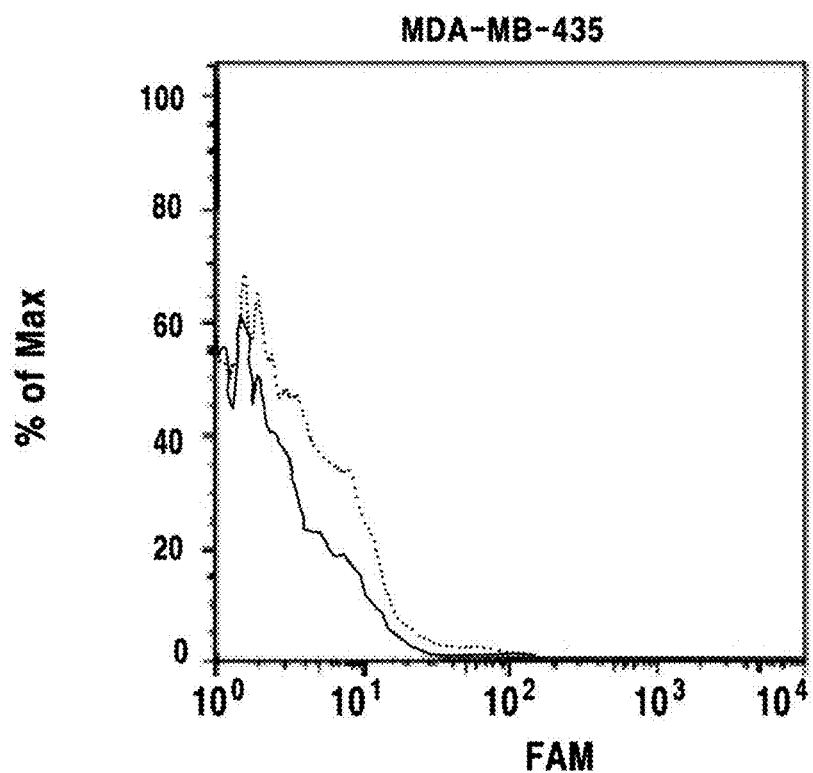
FIG. 7B shows an intracellular single-target miRNA detection analysis result using a composition for detecting a nucleic acid in an example of the present disclosure.
Figure 7B:
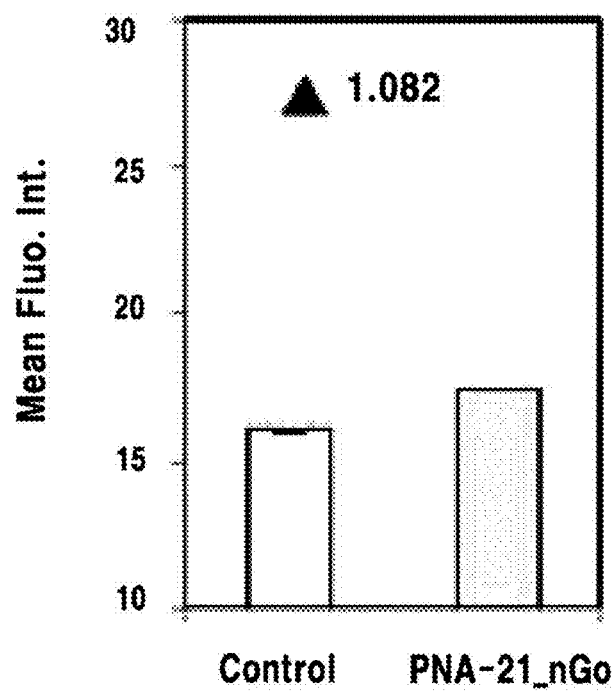
Figure 7C:
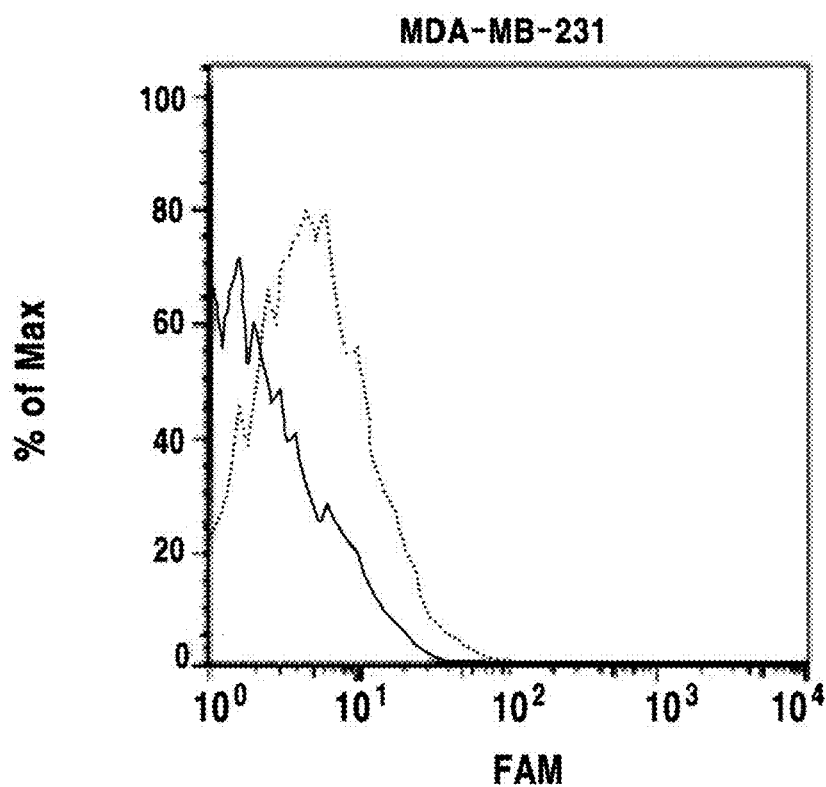
FIG. 7C shows an intracellular single-target miRNA detection analysis result using a composition for detecting a nucleic acid in an example of the present disclosure.
Figure 7C:
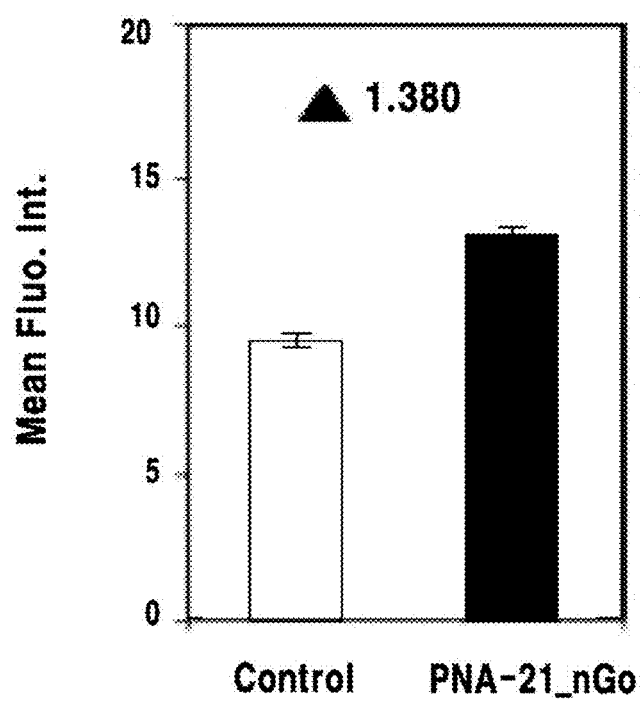
Figure 7D:
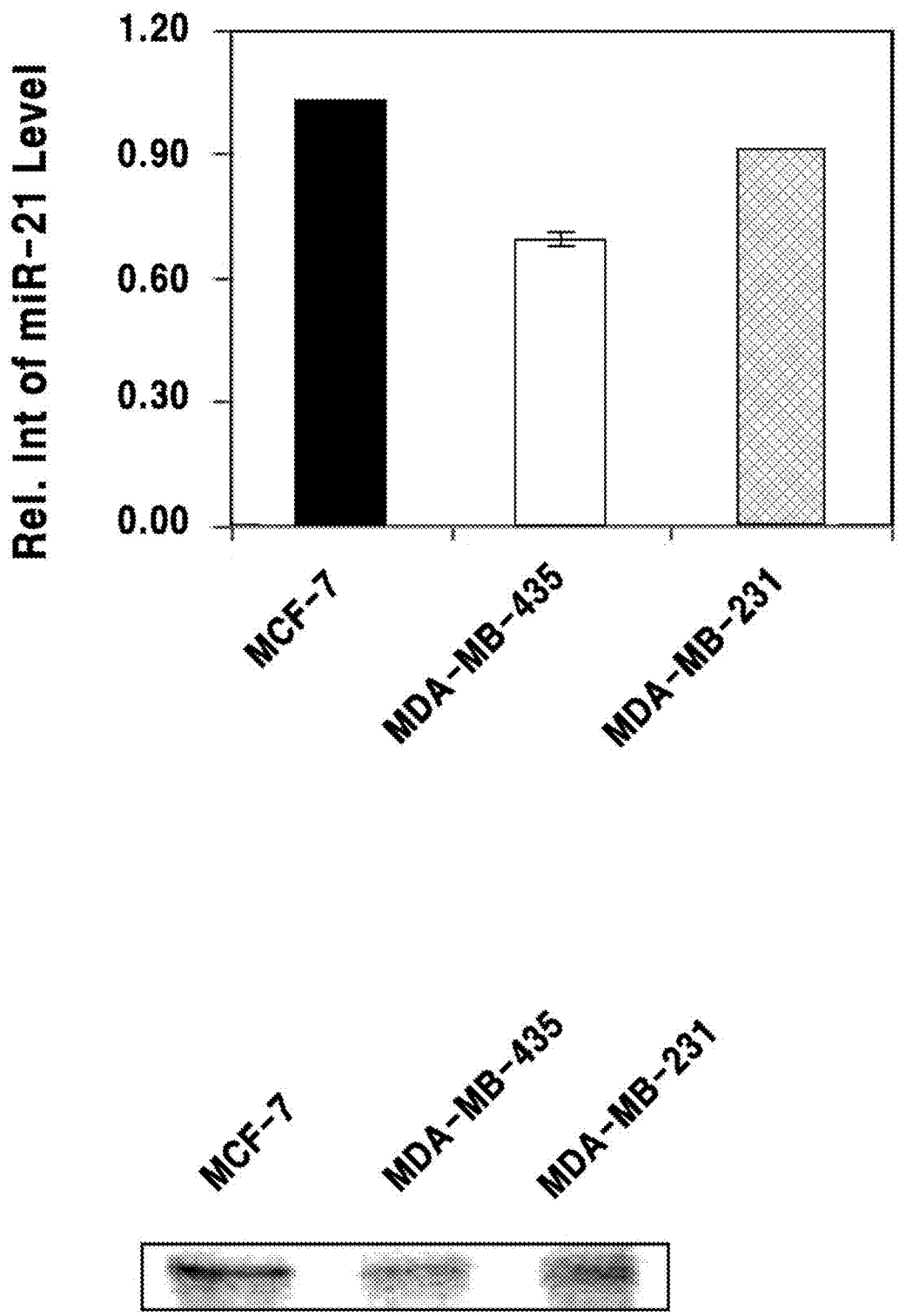
FIG. 7D shows an intracellular single-target miRNA detection analysis result using a composition for detecting a nucleic acid in an example of the present disclosure.
Figure 7E:
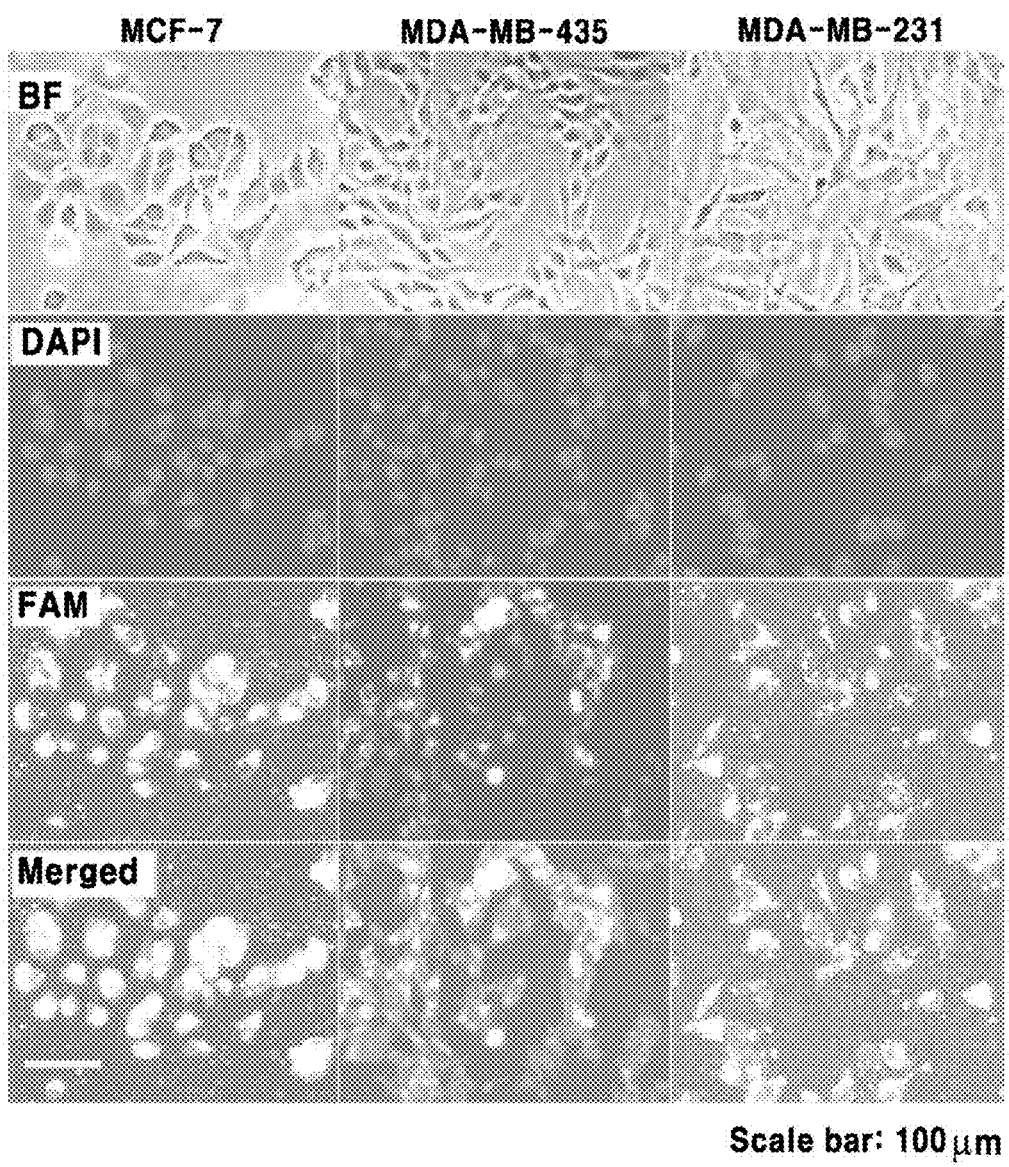
FIG. 7E shows an intracellular single-target miRNA detection analysis result using a composition for detecting a nucleic acid in an example of the present disclosure.
Figure 8A:
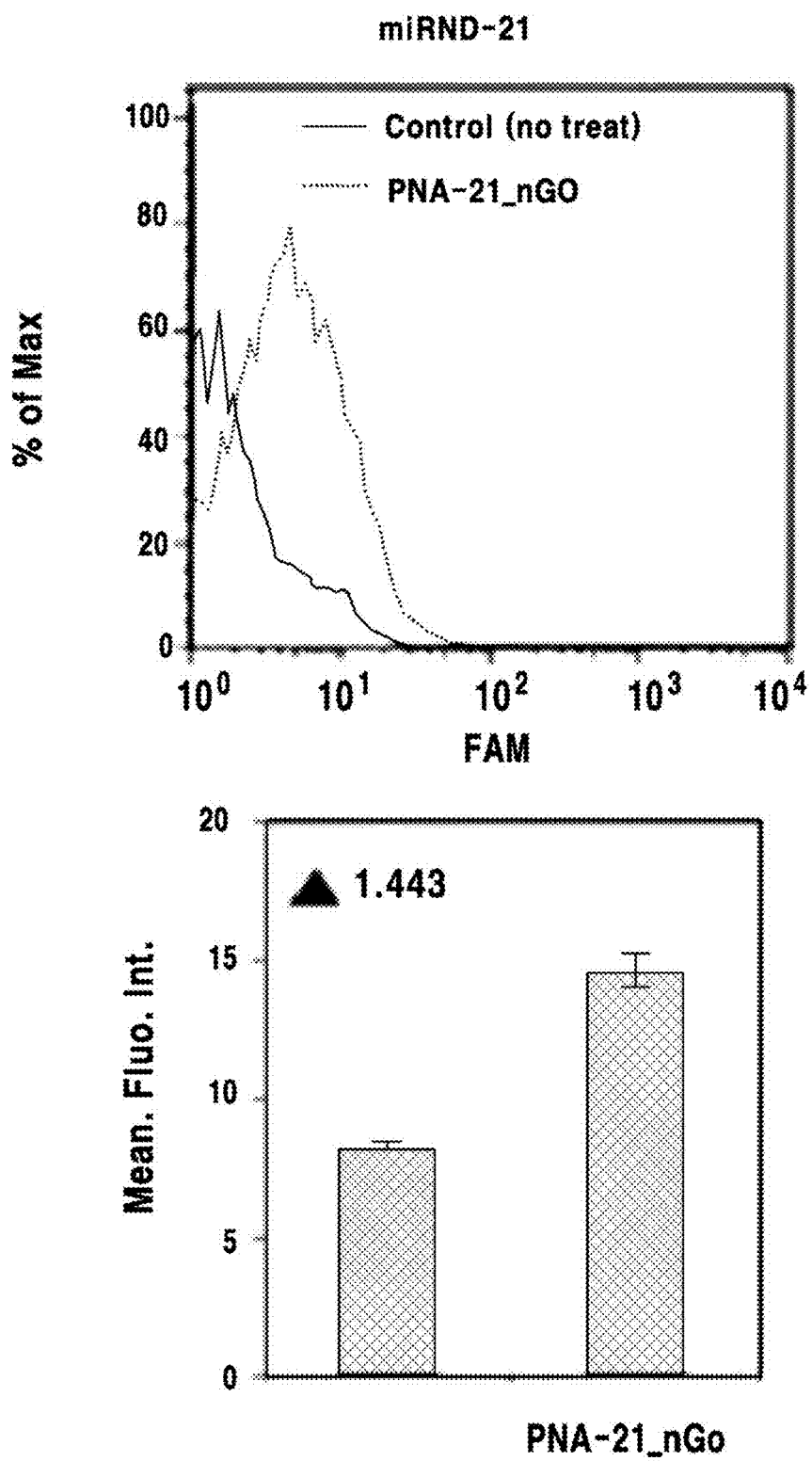
FIG. 8A shows an intracellular multi-target miRNA detection analysis result using a composition for detecting a nucleic acid in an example of the present disclosure.
Figure 8B:
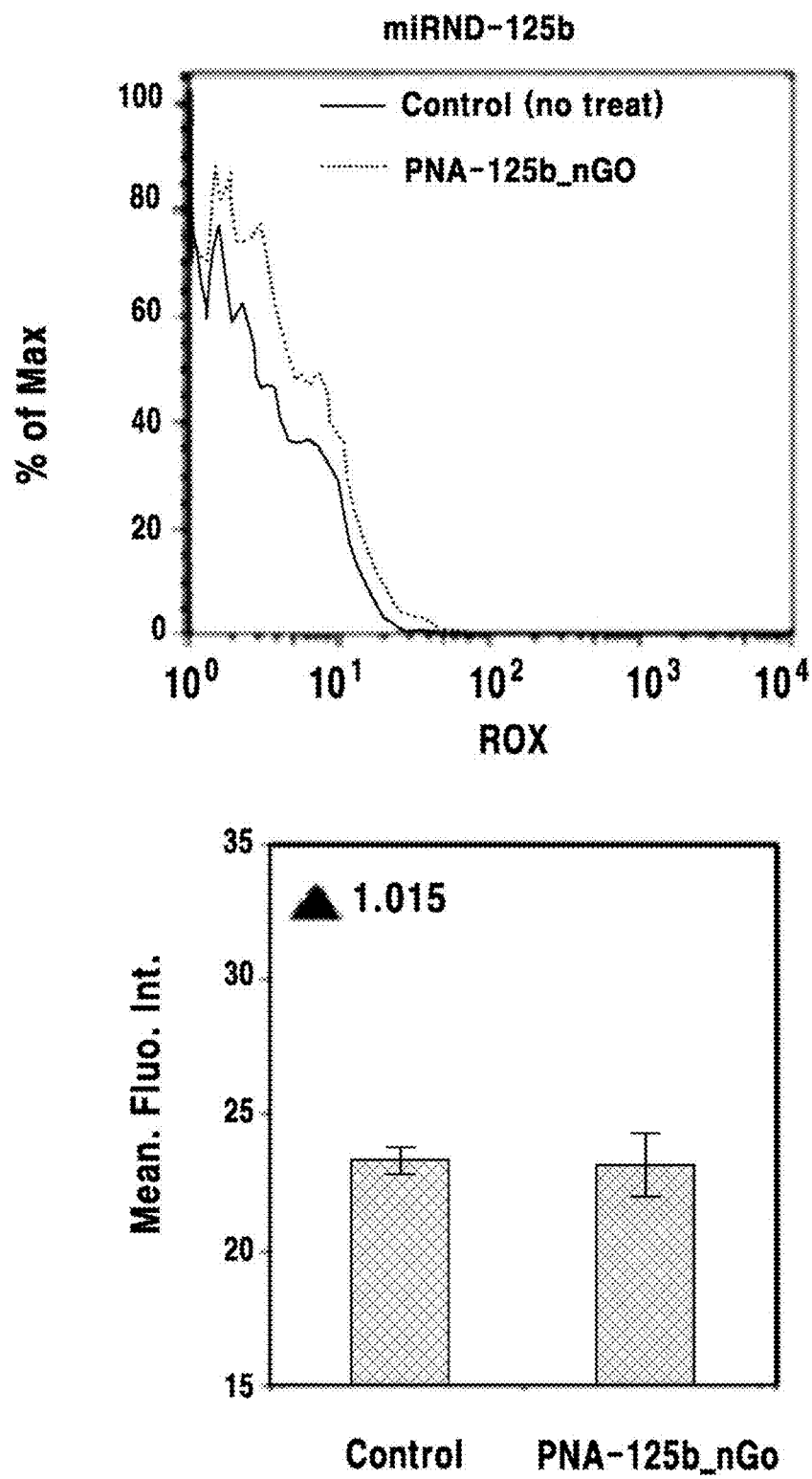
FIG. 8B shows an intracellular multi-target miRNA detection analysis result using a composition detecting a nucleic acid in an example of the present disclosure.
Figure 8C:
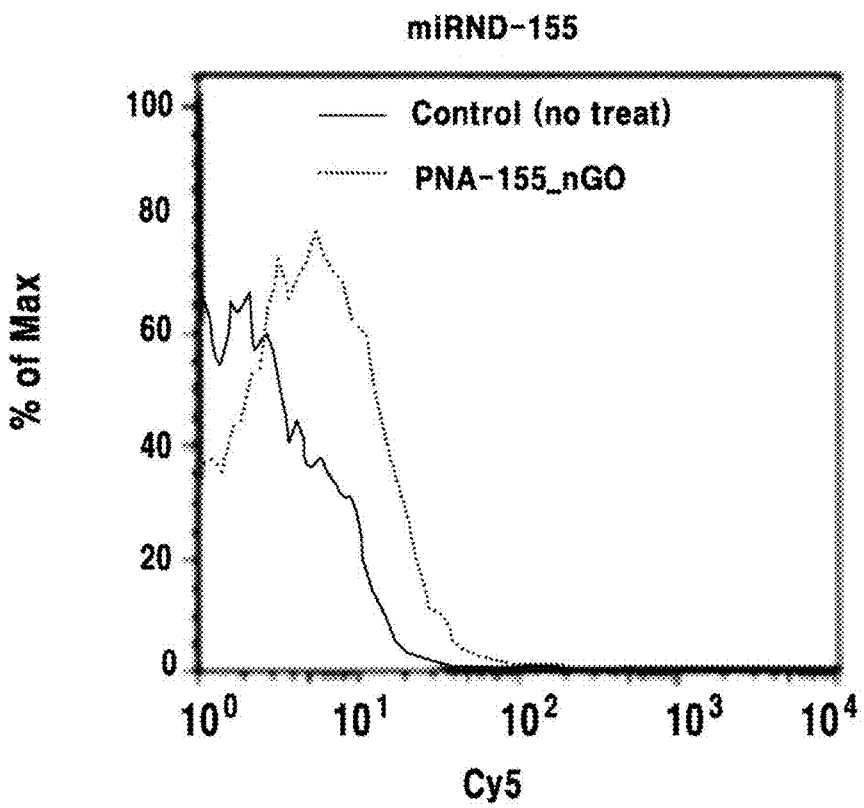
FIG. 8C shows an intracellular multi-target miRNA detection analysis result using a composition detecting a nucleic acid in an example of the present disclosure.
Figure 8C:
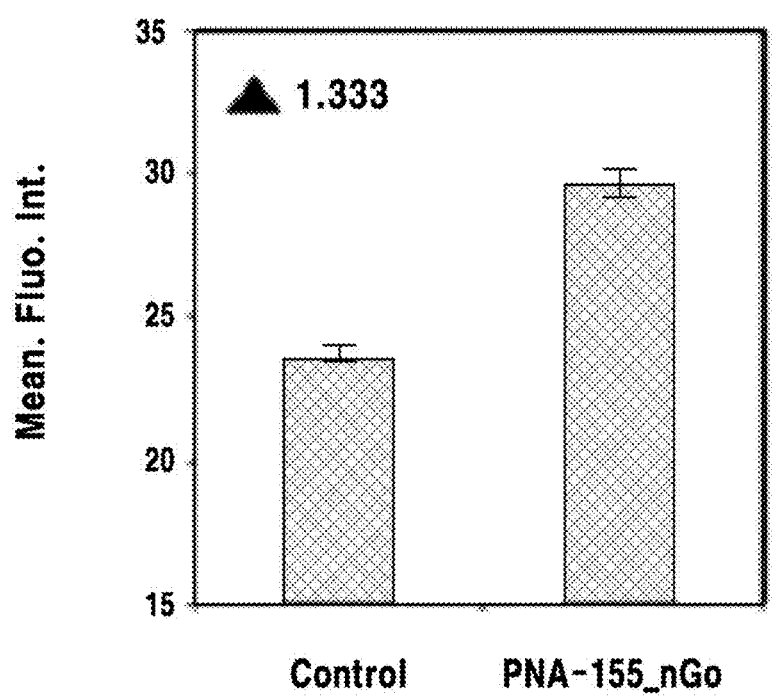
Figure 8D:
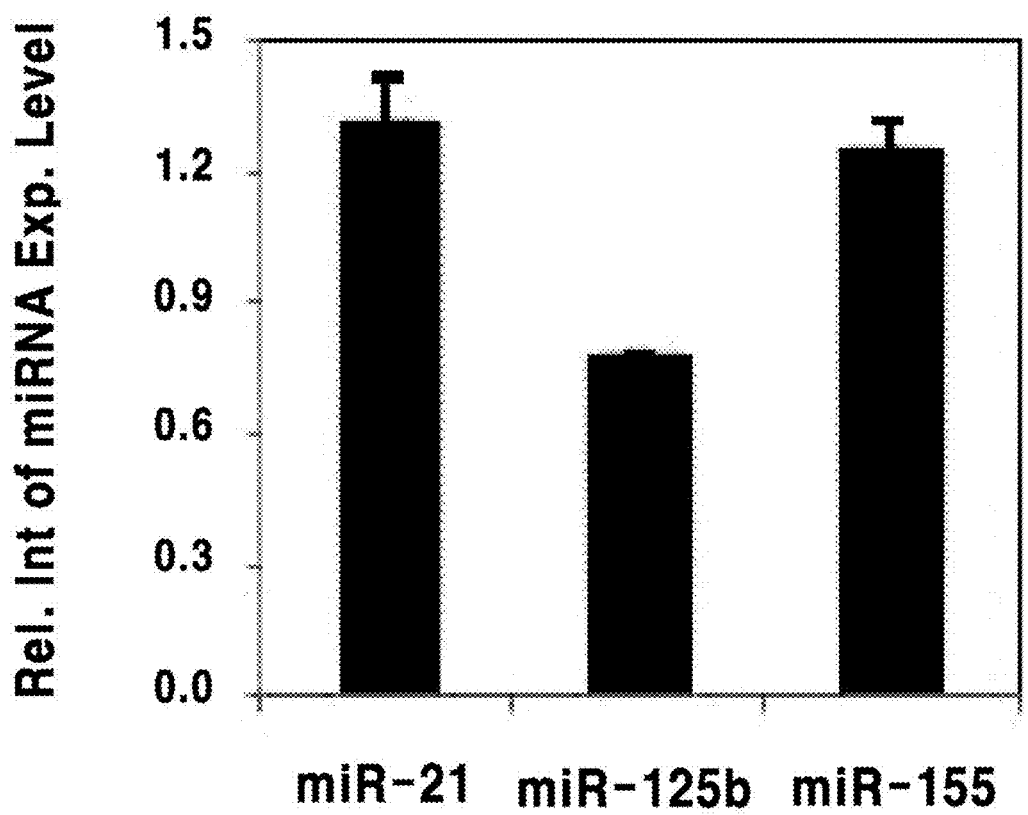
FIG. 8D shows an intracellular multi-target miRNA detection analysis result using a composition detecting a nucleic acid in an example of the present disclosure.
Figure 8D:
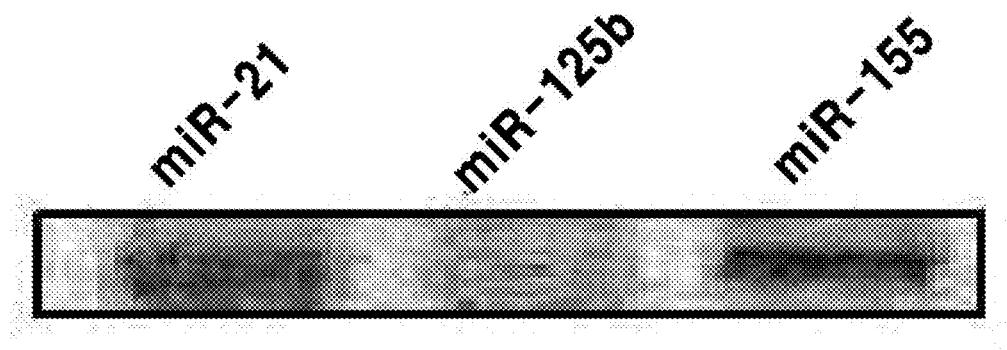
Figure 8E:
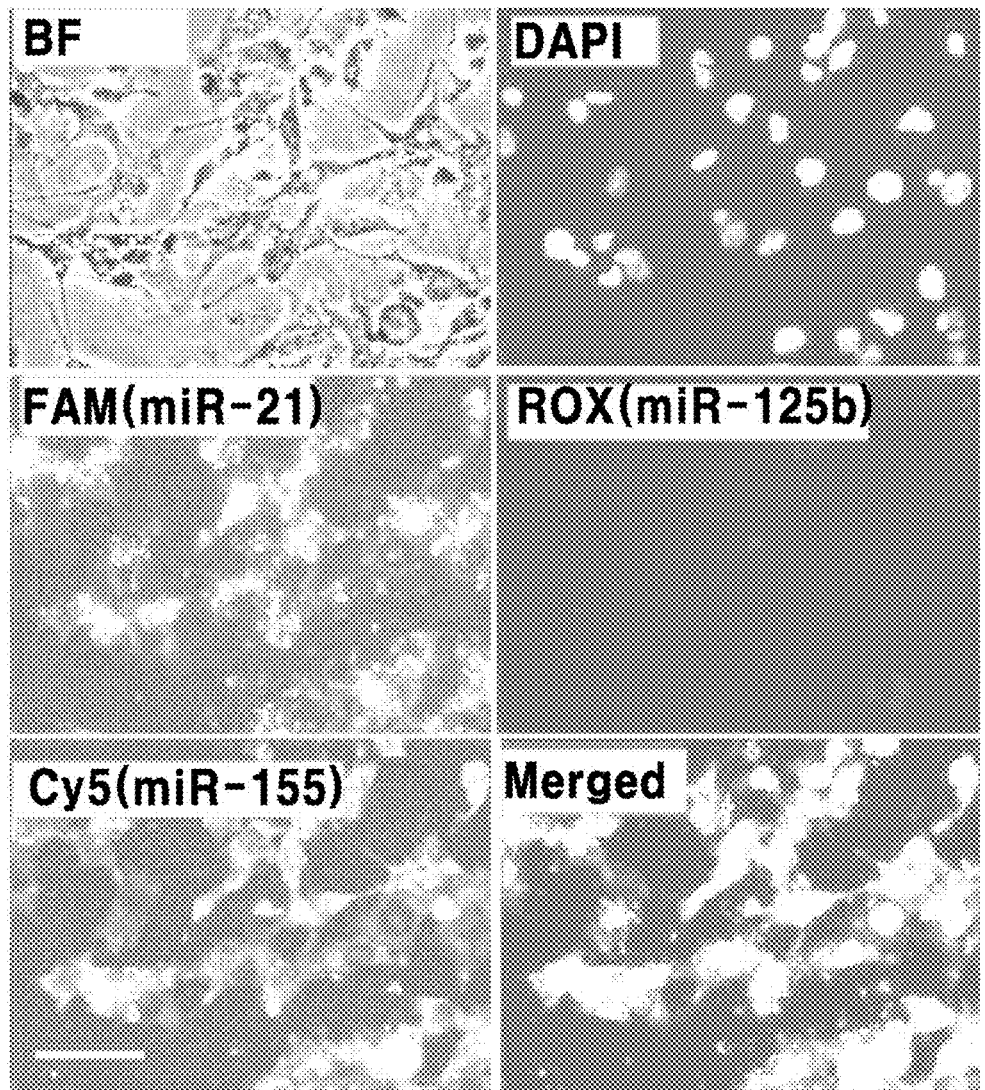
FIG. 8E shows an intracellular multi-target miRNA detection analysis result using a composition detecting a nucleic acid in an example of the present disclosure.
Figure 9A:
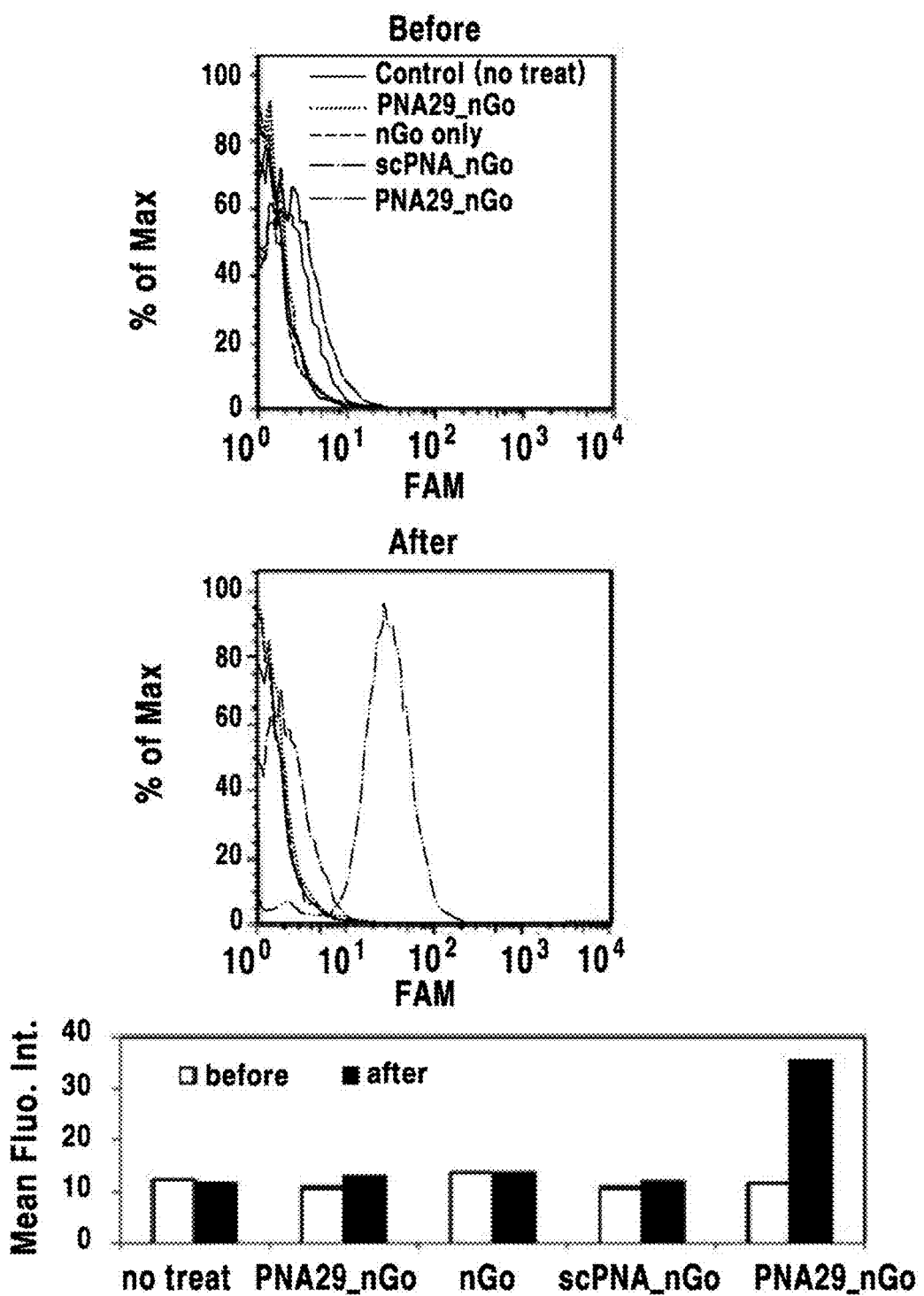
FIG. 9A shows a detection analysis result of a miRNA expression induced by doxycycline using a composition for detecting a nucleic acid in an example of the present disclosure.
Figure 9B:
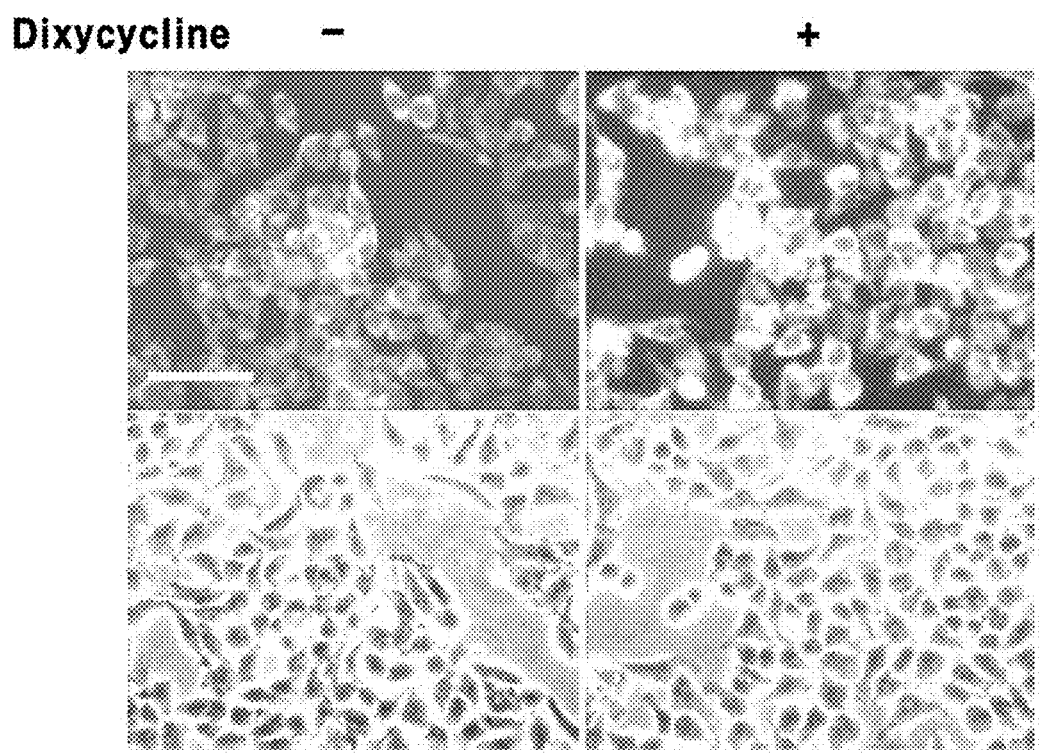
FIG. 9B shows a detection analysis result of a miRNA expression induced by doxycycline using a composition for detecting a nucleic acid in an example of the present disclosure.
Figure 9C:
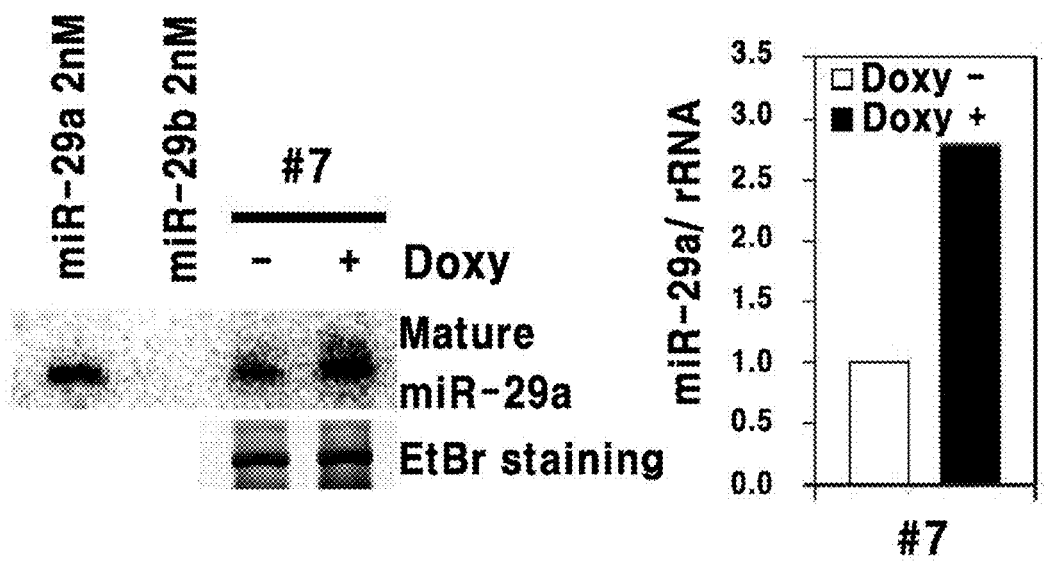
FIG. 9C shows a detection analysis result of a miRNA expression induced by doxycycline using a composition for detecting a nucleic acid in an example of the present disclosure.
Figure 9D:
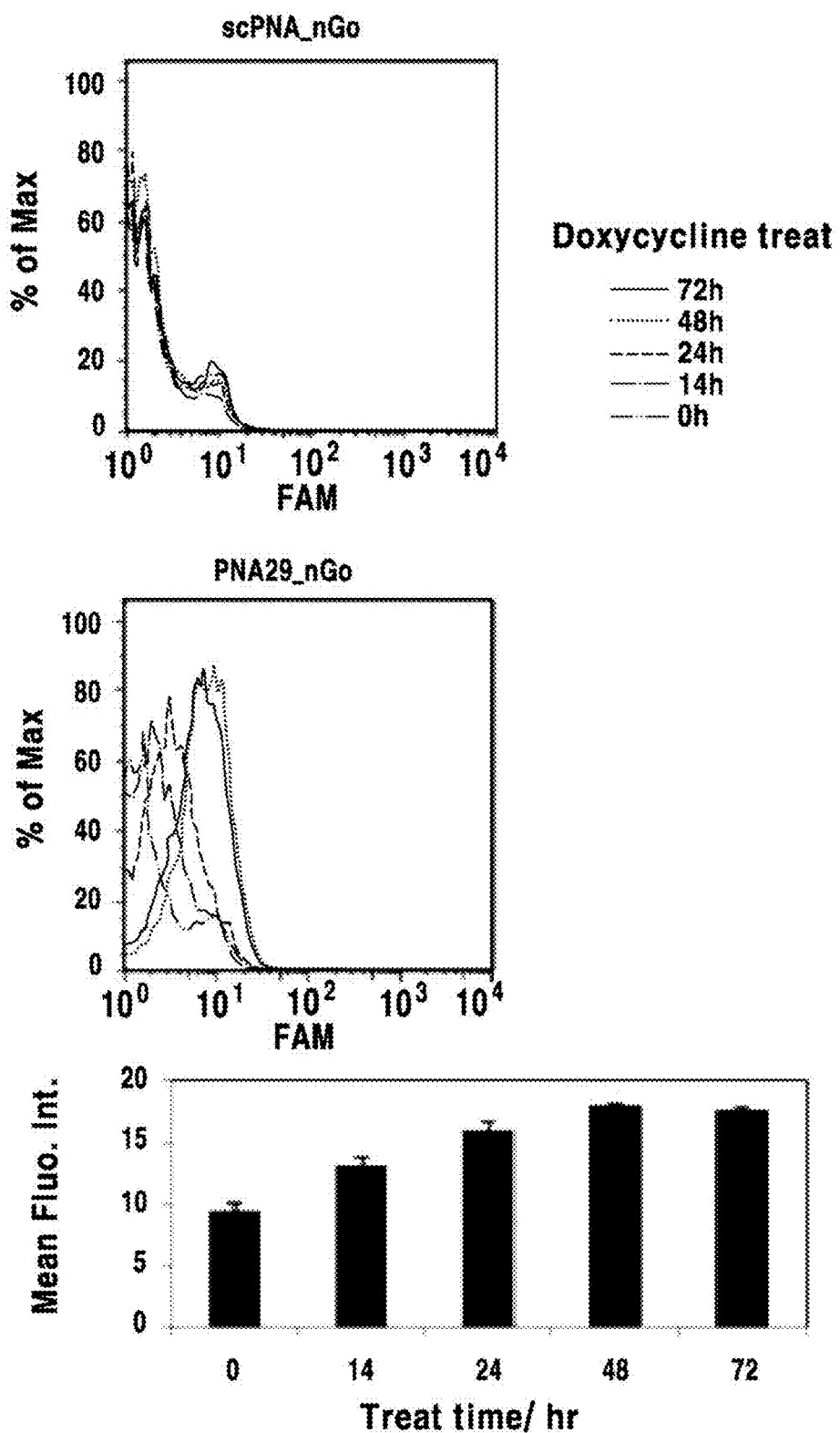
FIG. 9D provides a comparison of detection analysis results of a miRNA expression induced by doxycycline using a composition for detecting a nucleic acid in an example of the present disclosure, for respective doxycycline processing times.
Figure 9E:
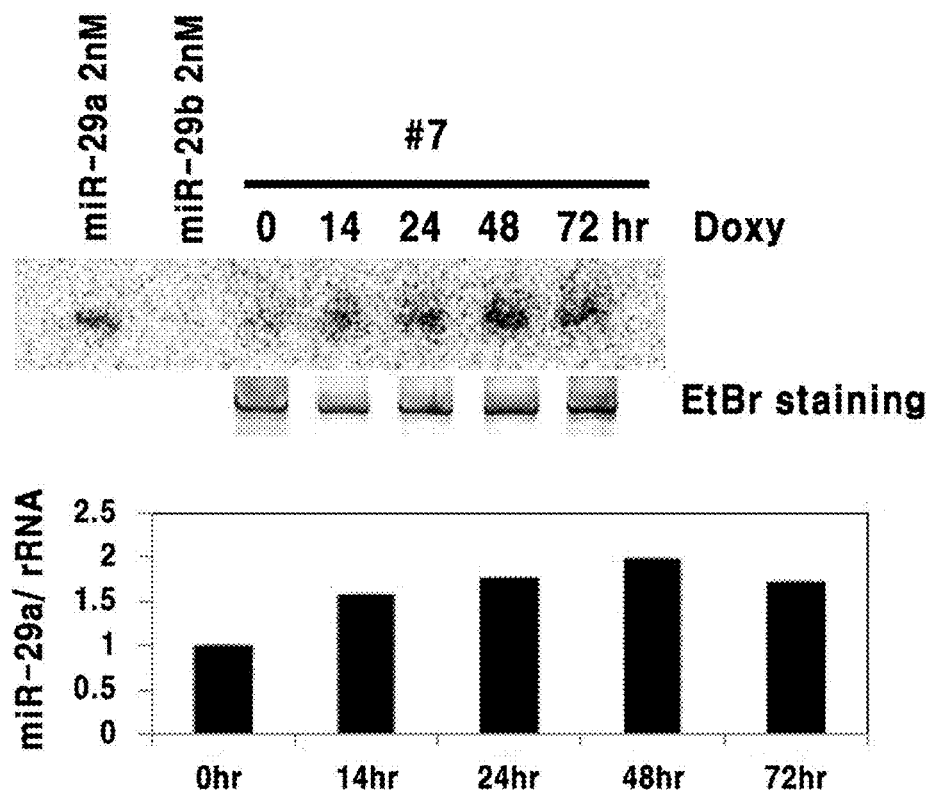
FIG. 9E provides a comparison of detection analysis results of miRNA expression induced by doxycycline using a composition for detecting a nucleic acid in an example of the present disclosure, for respective doxycycline processing times.

In this example, in order to prove that a PNA probe is combined with a miRNA as a target material in a base sequence specific manner, one to three kinds of miRNAs within a sample were accurately detected by three kinds of PNA probes and appearance of fluorescence signals was observed. First, one or more of a miRNA-21, a miRNA-125b and a miRNA-155 were included in samples in various combinations, such as one-type, two-types or three types. Then, three kinds of probes FAM-PNA-21, ROX-PNA-125b and Cy5-PNA-155 were added to the samples having various miRNA combinations and observed by using a fluorescence image analysis system. As a result, as shown in FIG. 6A to FIG. 6C, each PNA probe was found to react with only a miRNA having a complementary base sequence to that of the PNA probe and emit fluorescent light.

Example 4

Detection of a Single-target miRNA within a Living Cell

In this example, an intracellular miRNA was detected from a living cell, and an expression amount thereof was quantified. FAM-PNA-21 was mixed with nano-size graphene oxide having a unitary quantity of 1 μg and left at a room temperature for about 10 minutes. After completing the adsorption of the FAM-PNA-21 to the graphene oxide in this way, DMEM was added to this solution so that the total volume of the solution becomes 250 Eighty thousand cells per a well were prepared in a 24-well cell culture plate by using a breast cancer cell lines MCF-7, MDA-MB-435 and MDA-MD-231 as a model disease cell line. Each of the prepared cell samples was treated with the above-prepared 250 μL of FAM-PNA-21 and then left for about 14 hours. Thereafter, these cells were observed by using a flow cytometer (fluorescence activated cell sorter (FACS), e.g., FACS Aria I produced by BD Co.,) and a fluorescence microscope (IX71 of Olympus Co.,) and analyzed by a semi qRT-PCR. As a result, as can be seen from FIG. 7A to FIG. 7E, a miRNA-21 present after expressed in the cell line was detected by the FAM-PNA-21 and fluorescent light was emitted. Fluorescence intensities were found to follow the sequence of expression intensity of the miRNA-21 (in the order of MCF-7, MDA-MB-231 and MDA-MB-435), as already known in the art. Further, in accordance with the present example, it was also proved that real-time detection and quantification of a target miRNA can also be performed by flow cytometry without fixing a cell.

Example 5

Detection of Multi-target miRNs within a Living Cell

The presence of an intracellular miRNA was investigated and an expression amount thereof was quantified according to the same method as described in Example 4 excepting that only a MNA-MB-231 was used as a cell line and all of FAM-PNA-21, ROX-PNA-125b and Cy5-PNA-155 were used as PNA probes. As a result, as shown in FIG. 8A to FIG. 8D, a miRNA-21, a miRNA-125b and a miRNA-155 present after expressed in the cell line were detected by the PNA probes and fluorescent light was emitted. As for fluorescence intensities, the miRNA-21 and the miRNA-155 exhibited strong intensities, whereas the miRNA-125b showed weak intensity, the same as the expression intensities thereof as already known to those skilled in the art.

Example 6

Detection of miRNA Expressed by being Induced by Doxycycline

In this example, it was investigated, by means of flow cytometry, fluorescence microscope observation or semi qRT-PCR method, whether detection of a miRNA, which depended on presence or absence of doxycycline in a HeLa cell line genetically modified such that a miRNA-29a was expressed only under the presence of doxycycline, was accomplished. A PNA probe used in this example was PNA probe labeled with FAM. Specifically, FAM-PNA-29a having a sequence complementary to that of a miRNA-29a was used.

Expression of the miRNA-29a was observed by using the FAM-PNA-29a probe adsorbed on graphene oxide. As depicted in FIG. 9A to FIG. 9E, the miRNA-29a was detected after its expression from the HeLa cell line was induced by doxycycline, and the degree of expression changed with the time. However, in case that the probe was not used, a probe without labeled with FAM was used, only the graphene oxide was used, or a scrambled PNA (scPNA) with a scrambled sequence which was not complementary to a sequence of the miRNA-29a was used, no fluorescence was detected. That is, it was proved that a complex of a nucleic acid probe and graphene oxide emits different levels of fluorescence depending on the presence or absence of a nucleic acid as a target material when treated on a sample or a cell in which the nucleic acid as the target material having a sequence complementary to that of the probe is present.

Example 7

Figure 10:
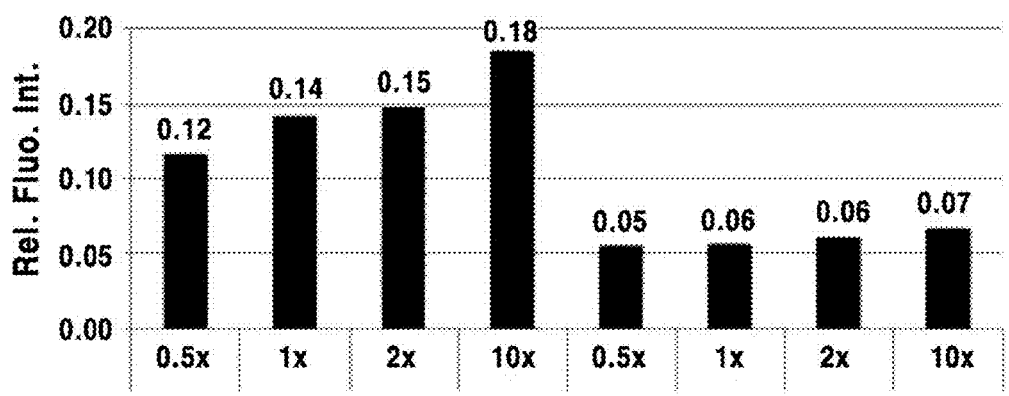
FIG. 10 is a diagram for describing a base-sequence-specific binding and a target-nucleic-acid-concentration-dependent binding of a PNA probe in an example of the present disclosure.
Figure 10:
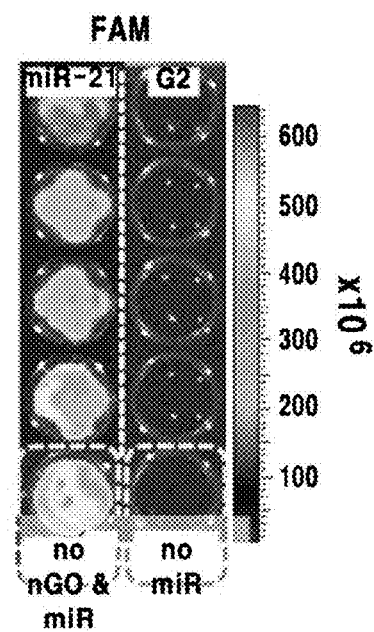

Base-sequence-specific PNA Probe Combination and Investigation of Fluorescence Depending on a Concentration of a Nucleic Acid as a Target Material In this example, a variation in fluorescence of a PNA probe according to a variation in a concentration of a target miRNA was observed. In this example, FAM-PNA-21 adsorbed on graphene oxide was applied to a miRNA-21 or G2 (a single-stranded RNA having a sequence of 5'-UGCG-CUCCUGGACGUAGCCU U-3' irrelevant to and different from the miRNA-21) having various concentrations. As shown in FIG. 10, the FAM-PNA-21 as the PNA probe was only combined with the miRNA-21 which was a target nucleic acid, and was separated from the graphene oxide and emitted fluorescence. The intensity of the fluorescence was found to increase in proportion to the concentration of the miRNA-21. Thus, it was proved that since the amount of the PNA probe separated from the graphene oxide increased with the rise of the concentration of the target nucleic acid, the target nucleic acid present in a sample could be detected quantitatively.

Example 8

Figure 11A:
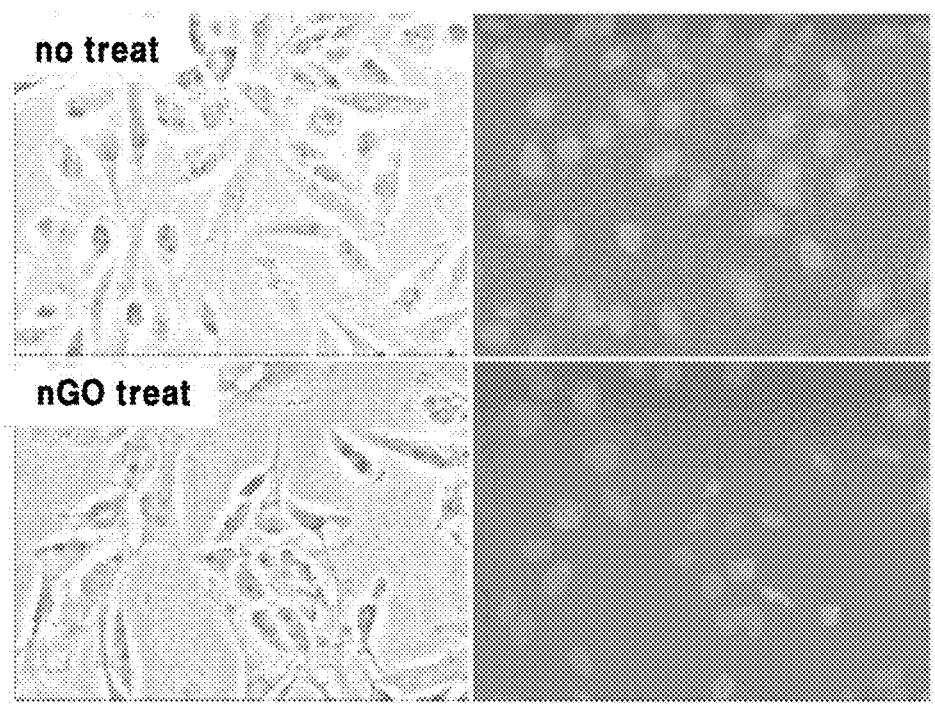
FIG. 11A shows an experimental result regarding introduction of a PNA probe into a cell which specifically reacts with the PNA probe adsorbed on graphene oxide in an example of the present disclosure.
Figure 11B:
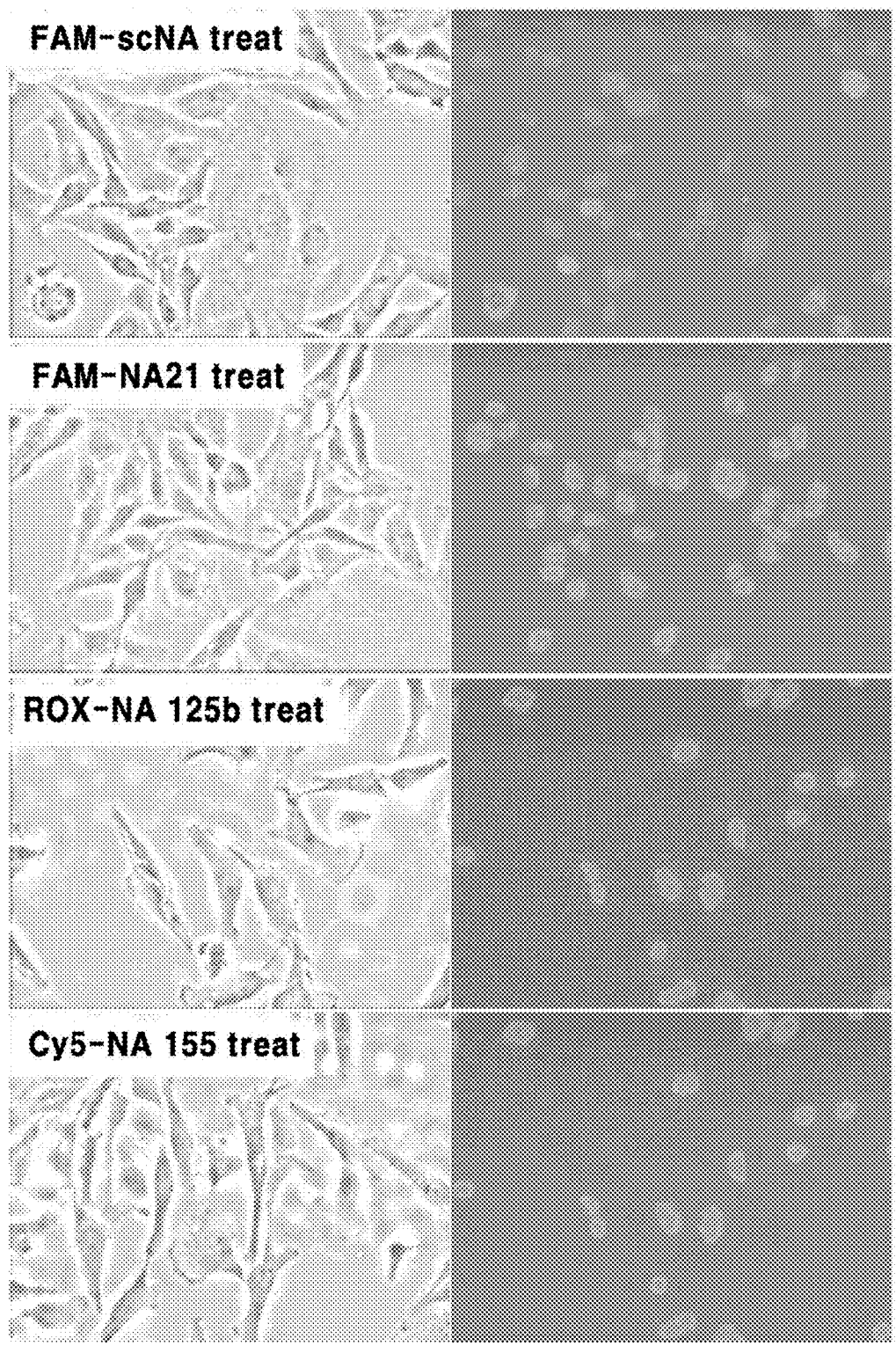
FIG. 11B shows an experimental result regarding introduction of a PNA probe into a cell which specially reacts with a PNA probe adsorbed on graphene oxide in an example of the present disclosure.

Investigation of Introduction into a Cell which Specifically Reacts to a PNA Probe Adsorbed on Graphene Oxide In this example, a cell was treated only with graphene oxide, or treated only with FAM-scPNA (a PNA probe having a scrambled sequence) as a PNA probe containing a fluorescent material which is not adsorbed on graphene oxide, FAM-PNA-21, ROX-PNA-125b or Cy5-PNA-155. Then, it was investigated whether fluorescence had occurred. As depicted in FIG. 11A and FIG. 11B, fluorescence was not observed in a non-treated cell or in a cell treated only with the graphene oxide. Further, since the PNA probe containing the fluorescence material could not be introduced to the inside of the cell in a state that the PNA probe was not adsorbed on the graphene oxide, fluorescence was also not detected even in case that only the probe was treated on the cell.

Preparation Example 3

Preparation of Graphene Oxide (GO)

An aqueous suspension of a graphene oxide was prepared by a modified Hummers' method.

The graphene oxide (GO) was synthesized using graphite nanofiber (Catalytic Materials LLC, USA) as a starting material by a Hummers' method including a pre-oxidation treatment. Firstly, concentrated $H_2SO_4$ (5 mL) (Samchun chemical, Seoul, Korea) was heated to 80° C. within a round-bottom flask, and $K_2S_2O_8$ (0.15 g) and $P_2O_5$ (0.15 g) (Sigma-Aldrich, MO, USA) were added to the round-bottom flask while maintaining the temperature at 80° C. for 4.5 hours. After the mixture was cooled, the reaction mixture was diluted with deionized water. This solution was filtered and washed with deionized water (100 mL) to remove the remaining reactants. The thus obtained pre-oxidized graphite nanofiber was dried in the air. Then, the dried solid was transferred to a 50 mL round-bottom flask, and concentrated $H_2SO_4$ (25 mL) was added thereto. Then, the mixture was cooled to 0° C. using an ice bath. $KMnO_4$ (1 g) (Sigma-Aldrich, MO, USA) was slowly added to the mixture with stirring while maintaining the temperature at 10° C. or less. After mixing, the flask was placed in a water tank of 35° C. for 12 hours. The mixture was transferred to an Erlenmeyer flask (500 mL) within the ice bath. Deionized water (100 mL) was slowly added to the flask with stirring. During this process, the temperature was maintained at less than 55° C. Then, 5 mL of a 30% $H_2O_2$ solution (Junsei, Japan) was added to the mixture, so that the mixture turned to light yellow. This mixture was collected and then centrifuged, and then washed with a 3.4% HCl solution and acetone to remove the remaining salt and acid. The thus obtained solid graphene oxide was dried in a vacuum before use. In order to obtain a graphene oxide solution, the graphene oxide was dissolved in water. Then, the solution was centrifuged at 3000 rpm for 30 minutes to remove large chunks.

Figure 13A:
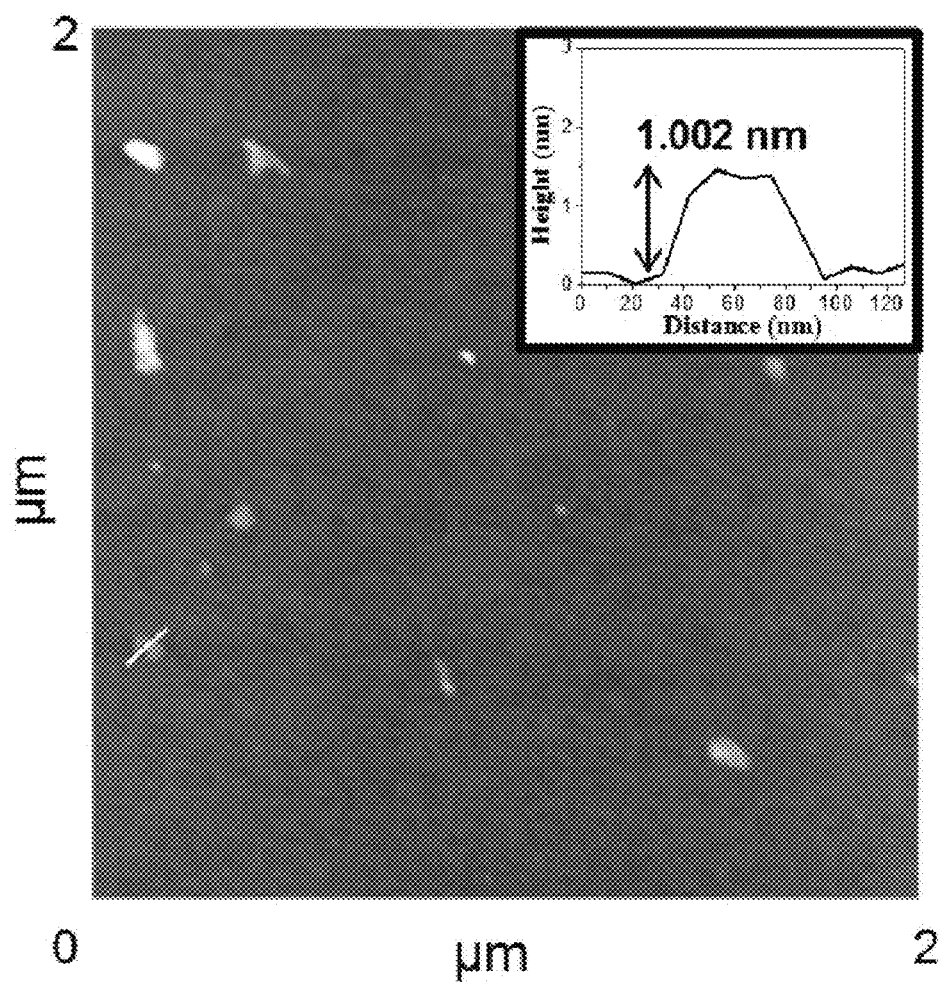
FIG. 13A to FIG. 13D show properties of a graphene oxide in accordance with an example of the present disclosure: (A) an atomic force microscopic (AFM) image showing an area of a graphene oxide prepared to be about 100 nm wide and about 1.0 nm high and a height profile (inserted image) of the graphene oxide; (B) a Raman spectrum and (C) a UV-Vis absorption spectrum of the graphene oxide suggesting a structural disorder of a sp2 carbon domain; and (D) a FT-IR spectrum of the graphene oxide confirming characteristic peaks of oxygen-containing functional groups present in the graphene oxide.
Figure 13B:
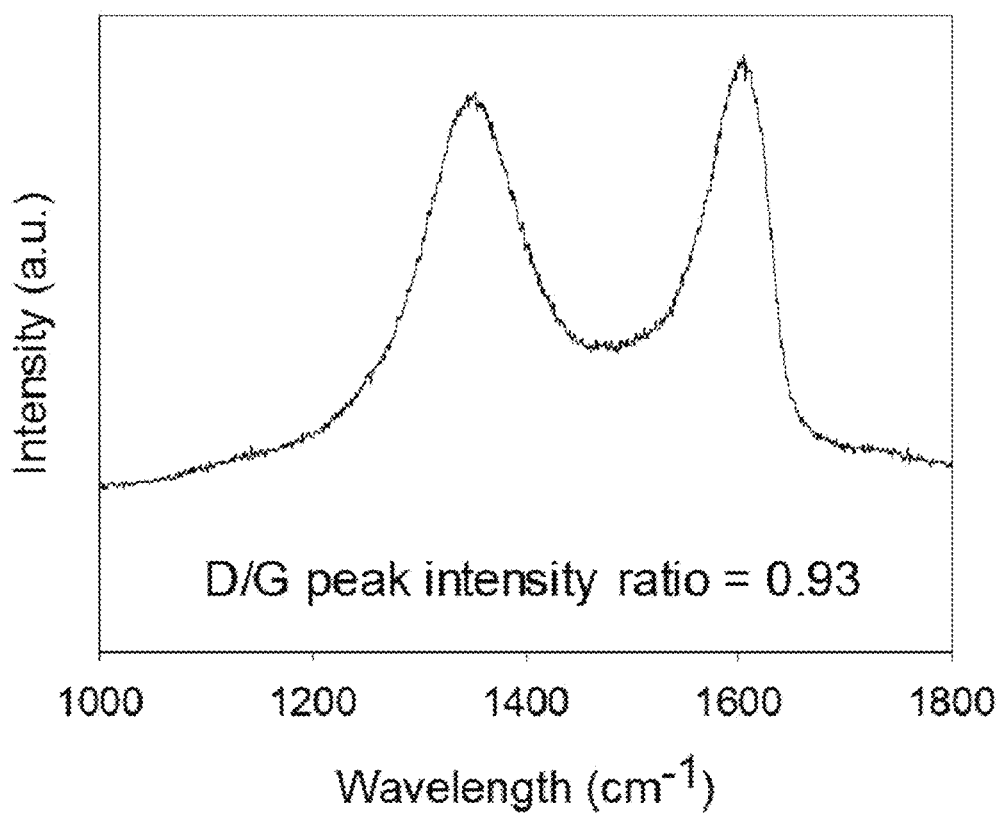
Figure 13C:
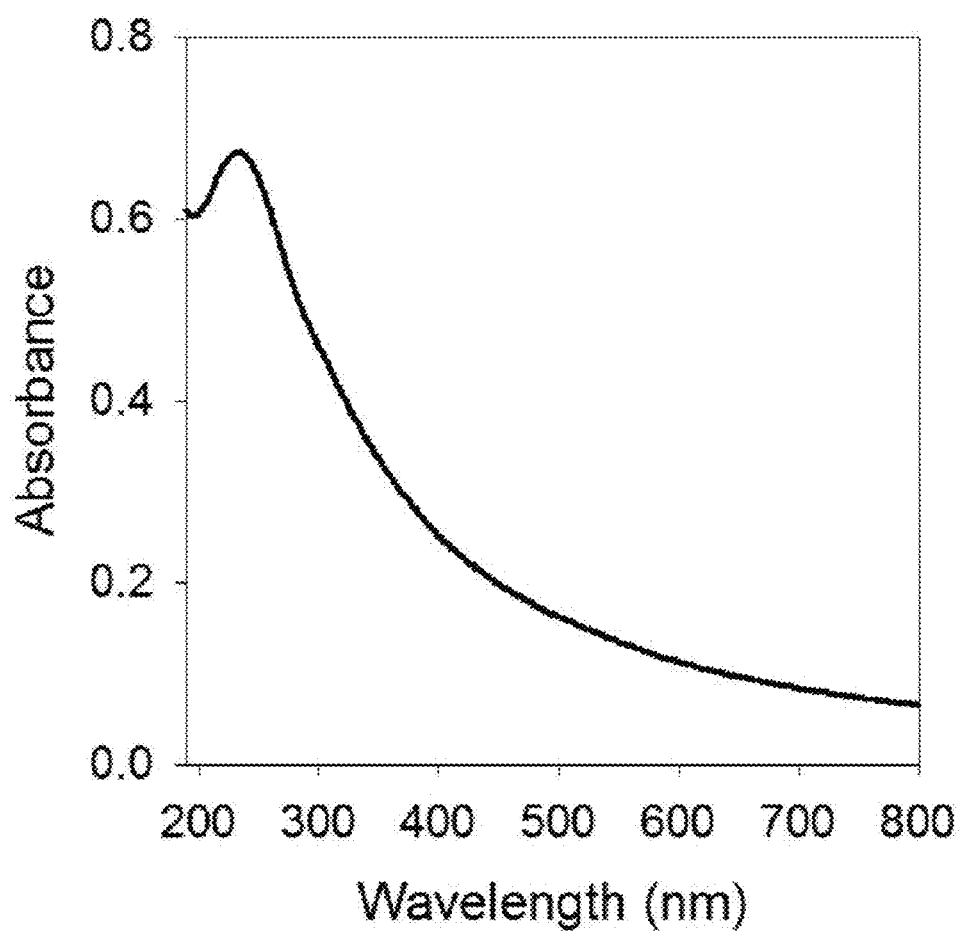
Figure 13D:
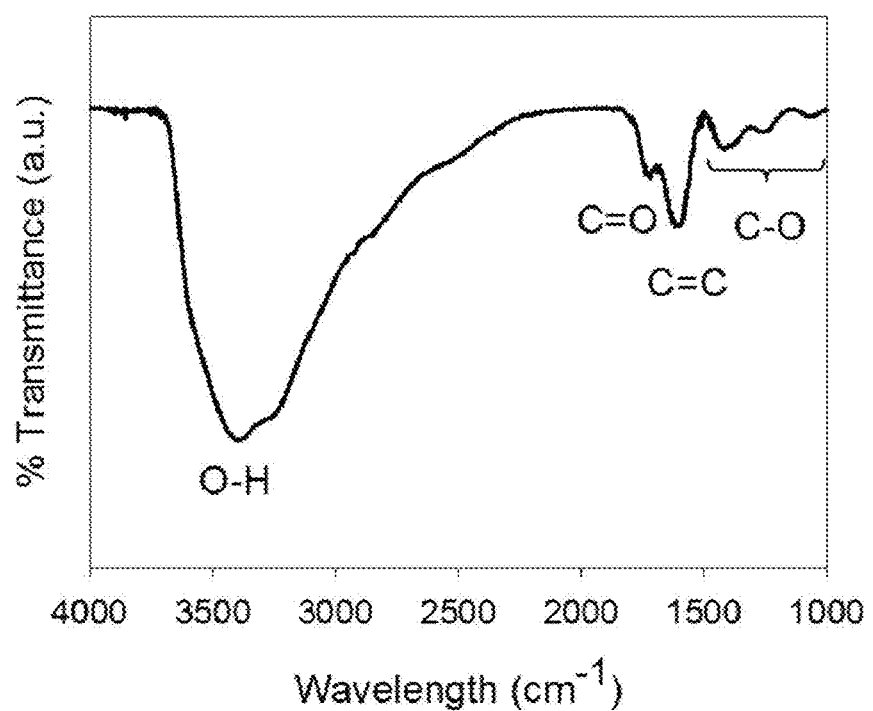

The monolayered graphene oxide was analyzed by atomic force microscopy (AFM) (FIG. 13A). Further, the graphene oxide was analyzed in more detail by Raman spectroscopy, UV-Vis absorption spectroscopy, and Fourier transform infrared (FT-IR) spectroscopy. According to the Raman spectrum, peaks were observed at 1352 $cm^{-1}$ and 1601 $cm^{-1}$ and corresponded to a D band associated with a structural disorder and a G band associated with an ordered sp2 carbon domain, respectively (FIG. 13B). According to the UV-Vis absorption spectrum, an absorption maximum value was observed at 234 nm associated with a π-π* transition of aromatic C=C bonds (FIG. 13C). Peaks in the FT-IR spectrum corresponded to various oxygen-containing functional groups of the graphene oxide (FIG. 13D). From the above experimental data, it can be seen that an aqueous suspension of the graphene oxide was successfully prepared.

Preparation Example 4

Preparation of Target DNA

In order to prepare a target DNA duplex, 2.5 μL of a 100 μM upper strand DNA was mixed with a lower strand DNA in an amount 1.1 times in excess of the upper strand DNA in a pH 8.0 buffer containing 50 mM Tris-HCl and 50 mM NaCl. Then, the mixture was heated and annealed at 90° C. for 5 minutes and then slowly cooled at room temperature for 1 hour.

Example 9

Displacement of a double-stranded DNA caused by a PNA was confirmed by degrading a PNA/DNA duplex and an intact double-stranded DNA by native polyacrylamide gel electrophoresis (Native-PAGE). A double-stranded target DNA was prepared by annealing an upper strand DNA (SEQ ID NO. 11: 5'-ATA AGC GTA ACT TCC CTC AAA-3') having a sequence complementary to a PNA probe (Panagene, Daejon, Korea) and a lower strand DNA (SEQ ID NO. 12: 5'-TTT GAG GGA AGT TAC GCT TAT-3') (Table 2).

The DNA strands were purchased from Genotech (Daejon, Korea), and the sequences thereof were as shown in the following Table 2:

TABLE 2

| | Upper strand | Lower strand |
|---|---|---|
| Perfectly matched dsDNA | SEQ ID NO. 1:<br>5' ATA AGC GTA ACT TCC CTC AAA 3' | SEQ ID NO. 2:<br>5' TTT GAG GGA AGT TAC GCT TAT 3' |
| Single bp mismatched | SEQ ID NO. 3:<br>5' ATA AGC GTA T̲CT TCC CTC AAA 3' | SEQ ID NO. 4:<br>5' TTT GAG GGA AG̲A TAC GCT TAT 3' |
| 3 bp mismatched | SEQ ID NO. 5:<br>5' ATA AGC GA̲A T̲CT A̲CC CTC AAA 3' | SEQ ID NO. 6:<br>5' TTT GAG GG̲T AGA T̲TC GCT TAT 3' |
| Scrambled dsDNA | SEQ ID NO. 7:<br>5' TAG CTT ATC AGA CTG ATG TTG A 3' | SEQ ID NO. 8:<br>5' TCA ACA TCA GTC TGA TAA GCT A 3' |

Figure 14:
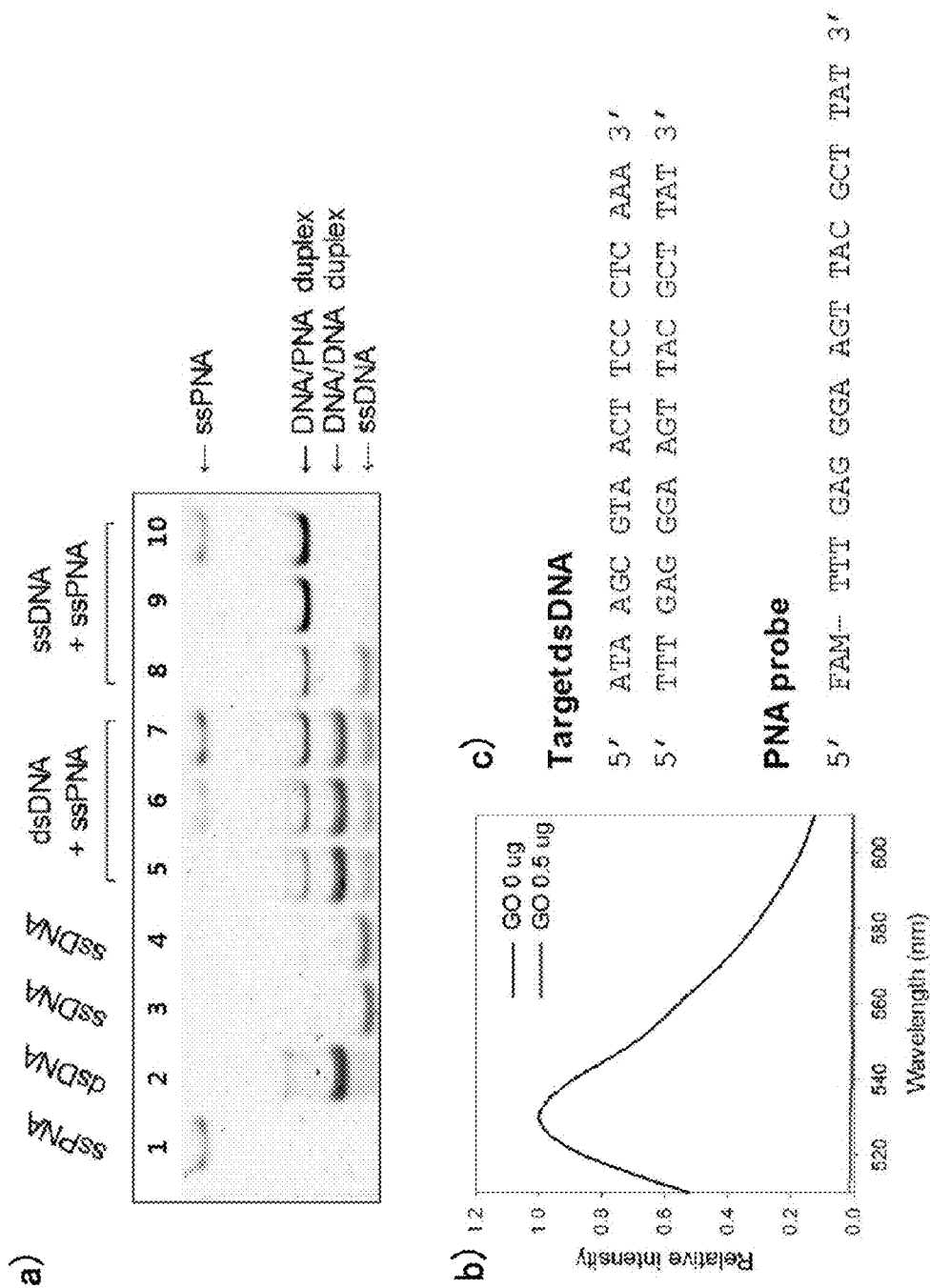
FIG. 14 shows a result of an experiment conducted to demonstrate hybridization of a PNA and a target nucleic acid in accordance with an example of the present disclosure: (a) gel electrophoresis was performed on a 15% native-PAGE; lines 1 to 4 show ssPNA, dsDNA, ssDNA (lower strand) and ssDNA (upper strand), respectively; lines 5 to 7 show 10 pmol double-stranded DNAs incubated with 5, 10 and 20 pmol PNAs, respectively; lines 8 to 10 show 10 pmol ssDNAs (upper strands) incubated with 5, 10 and 20 pmol PNAs, respectively; (b) fluorescence spectra of a FAM-labelled PNAs in the presence of (0 μg and 0.5 μg of) a graphene oxide, respectively; and (c) sequences of a double-stranded target DNA and a FAM-labelled PNA probe, respectively.

Due to less negative charge of the PNA/DNA duplex than a DNA/DNA duplex, a band of the hetero duplex was shown in an upper region because the hetero duplex moves more slowly than the DNA duplex in gel ((a) of FIG. 14). It is expected that this is because when the PNA probe was added to the double-stranded DNA, the PNA was first bonded to termini of the double-stranded DNA and then, when a lower strand DNA was separated, branch migration and perfect hybridization between the PNA and the DNA occurred. Then, an optimum concentration of the graphene oxide for quenching a fluorescent light of a fluorescein amidite (FAM)-labelled ssPNA probe (SEQ ID NO. 25: 5'-FAM-TTT GAG GGA AGT TAC GCT TAT-3') was determined. The present inventors found that in the presence of the graphene oxide (0.5 µg), a fluorescent light of the FAM-PNA probe was quenched to 98%, which was set as the maximum quenching efficiency under the experimental conditions ((b) of FIG. 14).

The DNA strand the PNA probe used for multiplexed double stranded DNA detection used in the present example and the subsequent examples were as shown in the following Table 3 and Table 4.

TABLE 3

| | Upper strand | Lower strand |
|---|---|---|
| HVA | SEQ ID NO. 9:<br>5' TTA GAG TTG CAT GGA 3' | SEQ ID NO. 10:<br>5' TCC ATG CAA CTC TAA 3' |
| HIV | SEQ ID NO. 11:<br>5' TAA CAT GAC CTG GAT3 | SEQ ID NO. 12:<br>5' ATC CAG GTC ATG TTA 3' |
| HVB | SEQ ID NO. 13:<br>5' ATG GAT GAT GTG GTA 3' | SEQ ID NO. 14:<br>5' TAC CAC ATC ATC CAT 3' |

TABLE 4

| PNA probe<br>(21 mer) | SEQ ID NO. 15:<br>5' FAM-TTT GAG GGA AGT TAC GCT TAT 3' |
|---|---|
| HVA probe<br>(15 mer) | SEQ ID NO. 16:<br>5' FAM-TCC ATG CAA CTC TAA 3' |
| HIV probe<br>(15 mer) | SEQ ID NO. 17:<br>5' ROX-ATC CAG GTC ATG TTA 3' |
| HVB probe<br>(15 mer) | SEQ ID NO. 18:<br>5' Cy5-TAC CAC ATC ATC CAT 3' |

Example 10

A reaction mixture was prepared by incubating 100 nM FAM-labelled PNA probe with an annealed double-stranded target DNA having various concentrations (0 nM to 500 nM) in 1×PBS (pH 7.2 buffer containing 137 mM NaCl and 2.7 mM KCl 2.7). Further, 400 nM scrambled double-stranded DNA were incubated with 100 nM FAM-labelled PAN probe. After the incubation at room temperature for 1 hour, 1 µL of 500 µg/mL graphene oxide stock was added to the mixtures. A fluorescence intensity was measured at 520 nm (Fluorometer: SynergyMx, Biotek, UK).

Figure 15:
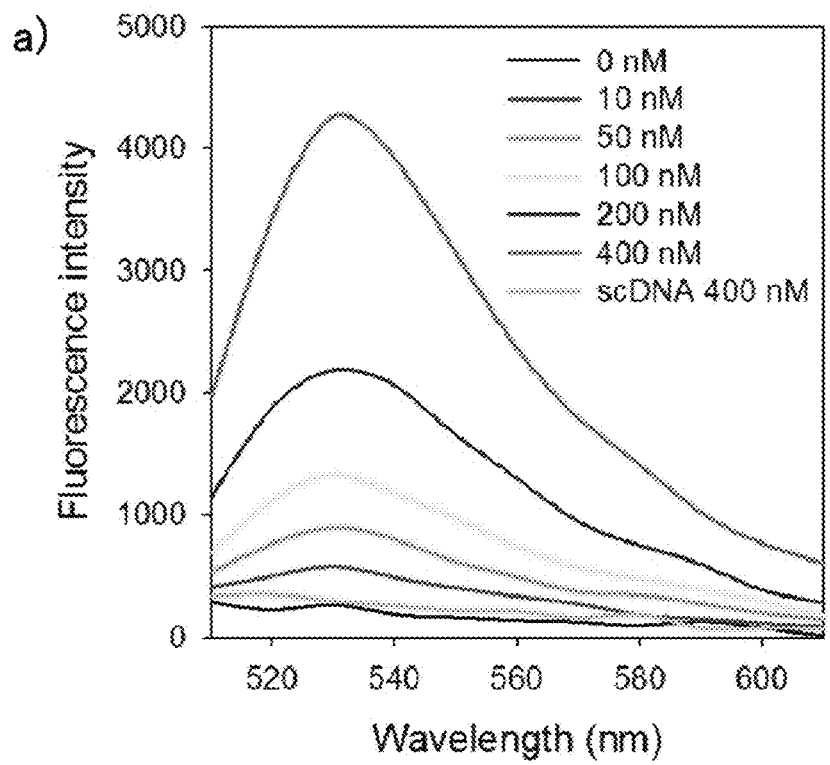
FIG. 15 shows a detection result of a target nucleic acid in accordance with an example of the present disclosure: (a) fluorescence spectra of a FAM-PNA probe in the presence of double-stranded target DNAs with various concentrations and a 400 nM scrambled dsDNA in a buffered solution added with a graphene oxide, respectively; and (b) an increase (F/F0) in fluorescence intensity associated with a target dsDNA in a wide concentration range of 0 nM to 100 nM (F: a fluorescence intensity of the PNA probe hybridized with the target, F0: the fluorescence intensity of the PNA probe without the target).
Figure 15:
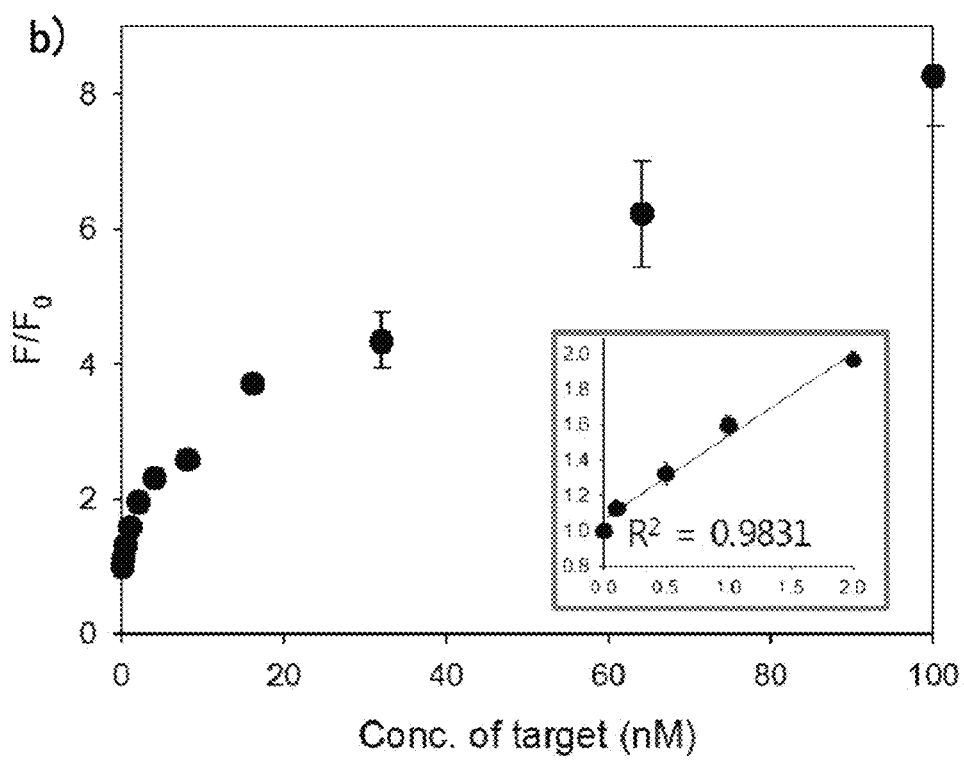
Figure 16A:
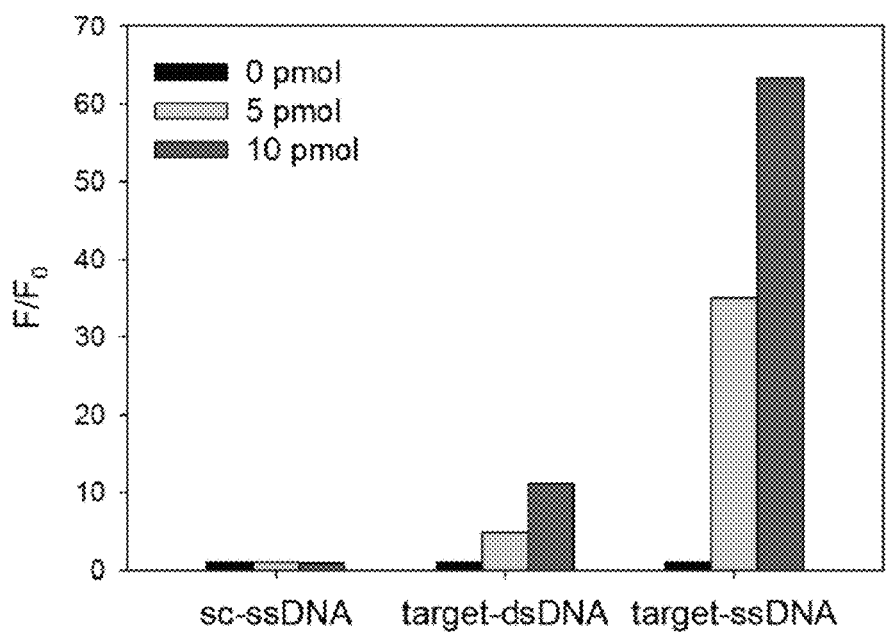
FIG. 16A to FIG. 16B show detection results of a target nucleic acid in accordance with an example of the present disclosure: an increase (F/F0) in fluorescence intensity of (A) a PNA probe and (B) a DNA probe in the presence of a scrambled ssDNA, a target dsDNA, a target ssDNA (each having a concentration of 0, 5, and 10 pmol).
Figure 16B:
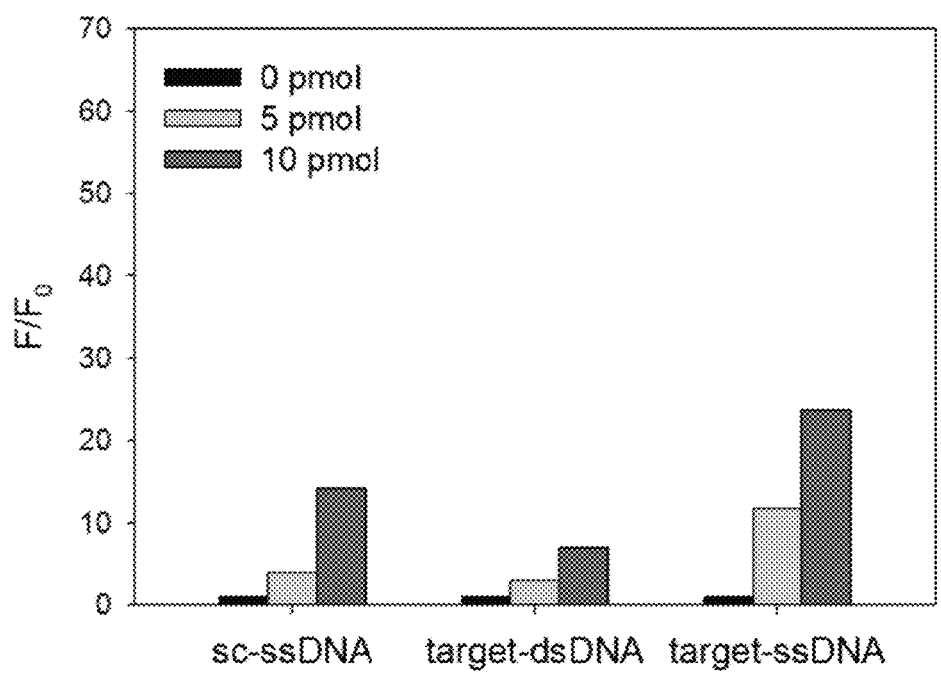

According to the fluorescence emission spectra of the mixed solutions of the double-stranded DNA, the FAM-PNA, and the graphene oxide showed the double-stranded DNA concentration dependent fluorescence enhancement with high sequence specificity showing no notable fluorescence intensity from a mixture containing scrambled double-stranded DNA in place of target double-stranded DNA ((a) of FIG. 15). This sensor showed a linear fluorescence increase between 0 pM to 2000 pM with a detection limit of 260 pM according to the equation [LOD=3.3 (SD/S) (LOD: Detection limit, SD: Standard Deviation, S: Slope of calibration curve] ((b) of FIG. 15). A double-stranded DNA (to 500 nM) having a higher concentration also showed a concentration-dependent fluorescence increase was (FIG. 16A and FIG. 16B).

Example 11

Figure 17A:
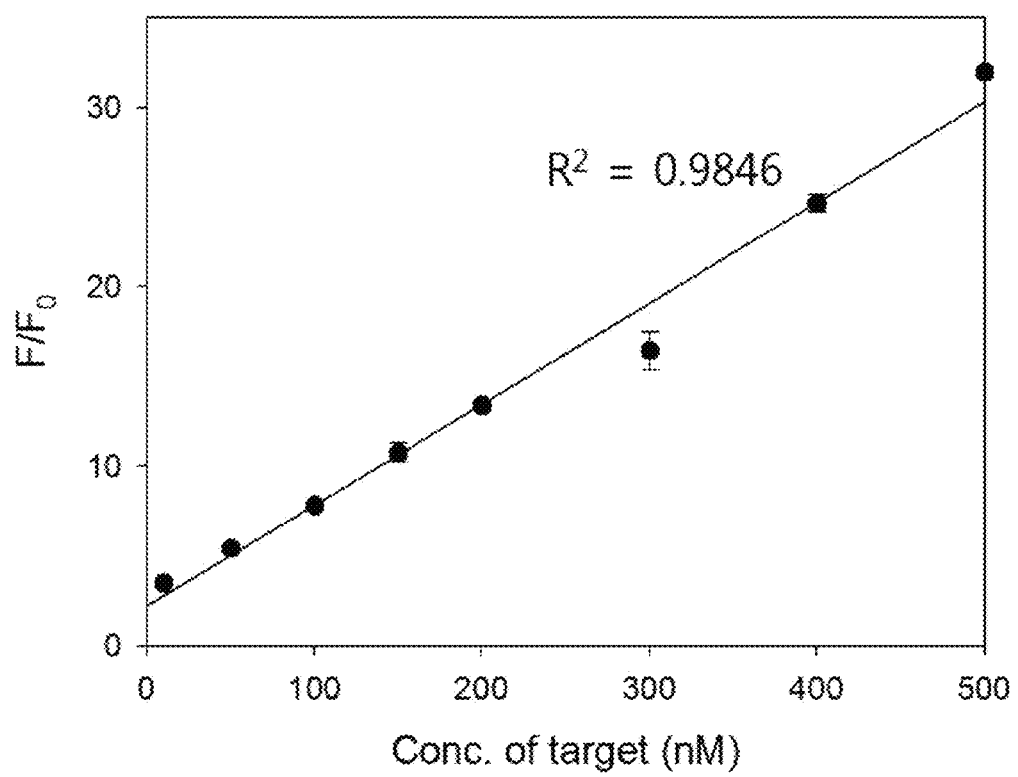
FIG. 17A to FIG. 17B show detection results of a target nucleic acid in accordance with an example of the present disclosure: (A) an increase (F/F0) in fluorescence associated with a target in a wide concentration range (~500 nM) in a 1×PBS solution; and (B) an increase (F/F0) in fluorescence intensity associated with a high-concentration target and a scrambled sequence dsDNA (F: the fluorescence intensity of a PNA probe including the target, F0: the fluorescence intensity of the PNA probe without the target).
Figure 17B:
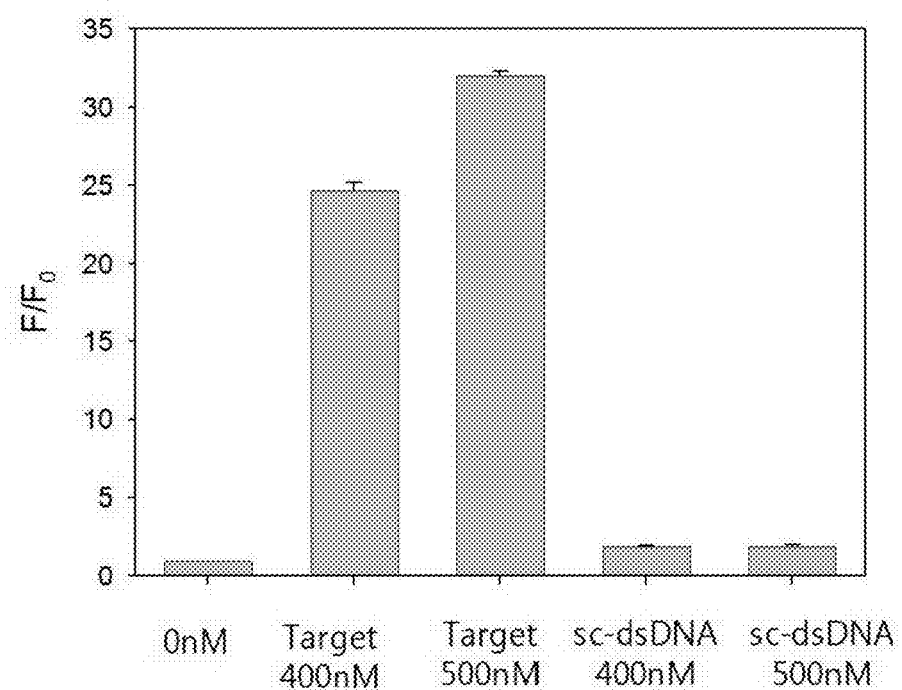

As a control, an experiment using a FAM-DNA probe instead of a FAM-PNA probe was conducted. The FAM-DNA probe showed a significant signal increase upon addition of scrambled DNA followed by addition of a graphene oxide. This signal was evaluated as about 50% of the fluorescence intensity measured from a mixture of the FAM-DNA probe which was perfectly matched with the target DNA and the graphene oxide. That is, from the data about the control using the FAM-DNA probe instead the FAM-PNA probe, it could be seen that the DNA probe had much lower suitability for direct sequence-specific quantitative detection of a double-stranded DNA than the PNA probe (FIG. 17A and FIG. 17B).

Example 12

Figure 18:
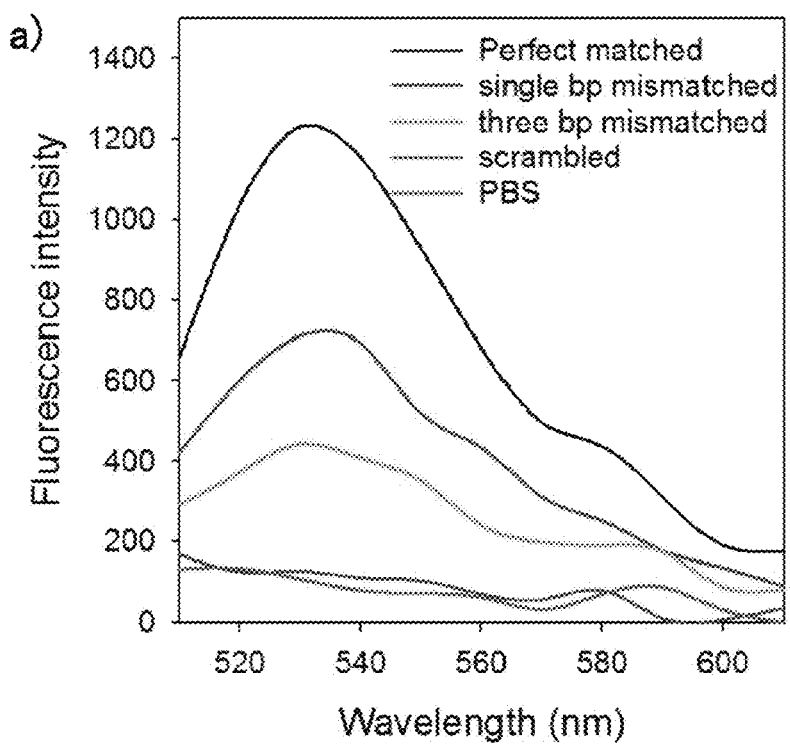
FIG. 18 shows a detection result of a target nucleic acid in accordance with an example of the present disclosure: (a) fluorescence spectra of a PNA probe in the presence of a target dsDNA, a single base-pair mismatched dsDNA, a three base-pair mismatched dsDNA, and a scrambled sequence dsDNA, added with a graphene oxide; and (b) a bar graph showing an increase (F/F0) in fluorescence intensity of matched and mismatched target dsDNA (at 0, 50 and 100 nM, respectively).
Figure 18:
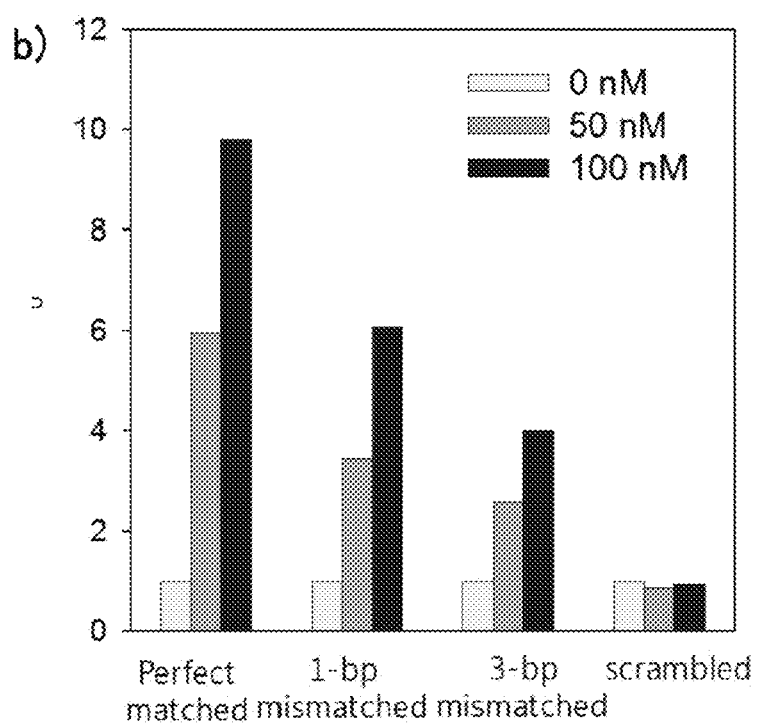

A test for discrimination between the perfectly matched target sequence and the mismatched target sequence described in the above Table 2 was conducted. Recognition of a mismatched sequence in a human gene is important in that it can provide clues to genetic mutation, DNA damage, and single nucleotide polymorphisms (SNP). One and three base-pair mismatched target DNAs were designed by using transversion mismatch in internal bases (A in a sequence was displaced with T, A↔T). As can be expected, a mismatched target showed a much lower fluorescence intensity than a perfectly matched target upon addition of FAM-PNA and graphene oxide ((a) of FIG. 18). A single mismatch in the middle of an upper target strand had F/F0 value decreased to 57%, as compared with a perfectly matched target DNA. Further, in a sequence in which three bases are mismatched, the F/F0 value was decreased to about 35%. In a scrambled double-stranded DNA, it was decreased to about 1% (measured from samples of each 100 nM target incubated with a 100 nM PNA probe) ((b) of FIG. 18).

Example 13

Figure 19:
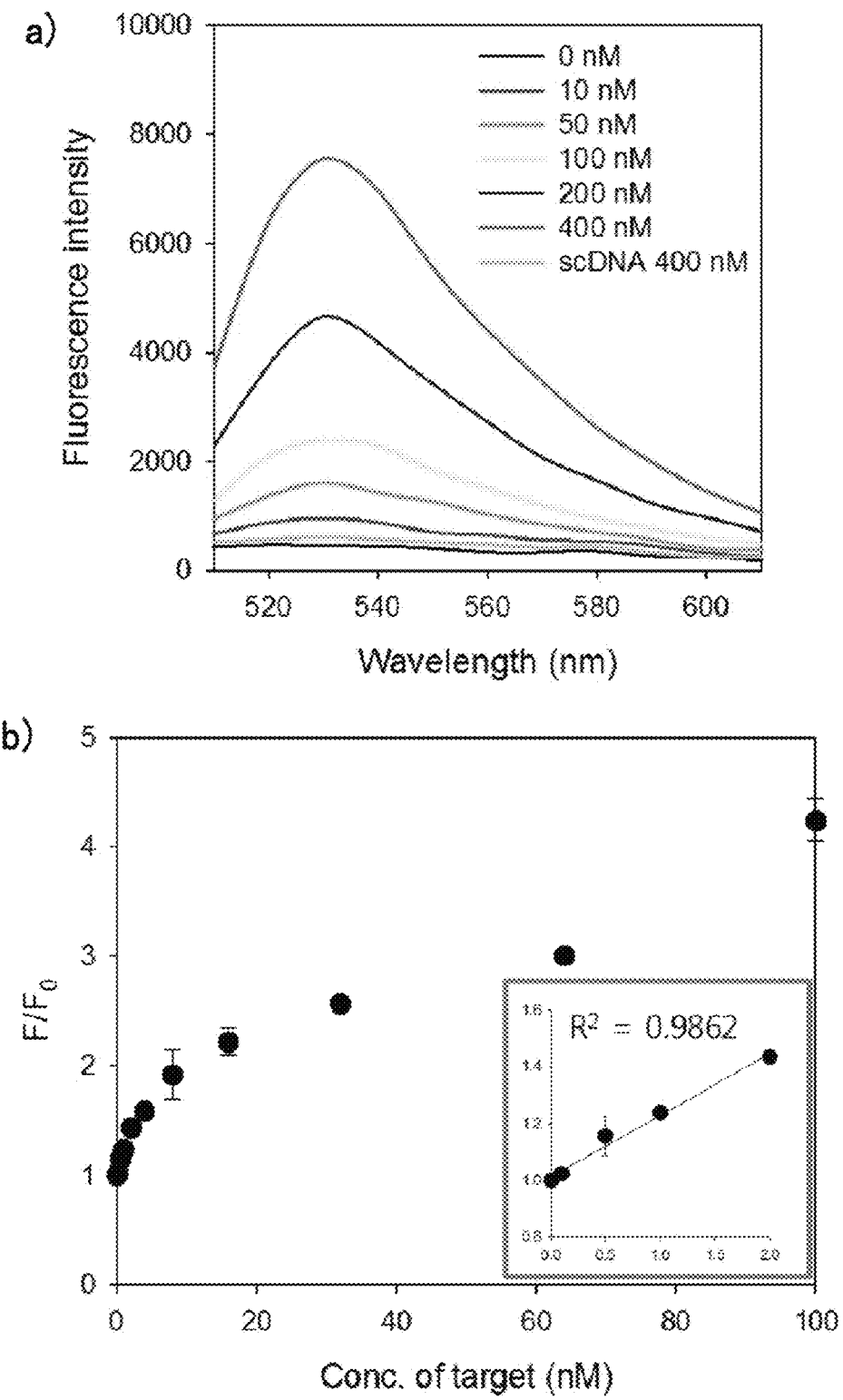
FIG. 19 shows a detection result of a target nucleic acid in accordance with an example of the present disclosure: (a) fluorescence spectra of a PNA probe in the presence of target dsDNAs with various concentrations and a scrambled dsDNA in 10% FBS-containing buffered solution added with a graphene oxide, respectively; and (b) an increase (F/F0) in fluorescence intensity of a target in a wide concentration range of 0 nM to 100 nM in 10% FBS-containing buffered solution.

In order to check whether the method of the present disclosure can be applied to directly detect a double-stranded DNA from bio-samples containing serum, an experiment for detecting a double-stranded DNA from buffered solutions each containing 10% fetal bovine serum (FBS) (Welgene, Daegu, Korea) was conducted. According to the fluorescence spectra, a fluorescence intensity was slightly higher than that from the solutions prepared in 1×PBS ((a) of FIG. 19). Various proteins in the FBS with a non-specific affinity with a surface of a graphene oxide could suppress weak absorption of a PNA/DNA duplex to the graphene oxide, whereas ssPNA still showed a stronger affinity with the graphene oxide than the serum protein and the PNA/DNA duplex. Under the above-described conditions, a sensor showed a slightly higher detection limit of 400 pM according to the equation [LOD=3.3(SD/S)], which shows a linear fluorescence increase in the same concentration range as the target DNA (0 pM to 2000 pM) ((b) of FIG. 19). As shown in (b) of FIG. 19, under the above-described conditions, the sensor showed a linear fluorescence increase in the same concentration range as the target DNA (0 pM to 2000 pM) and also showed a slightly higher detection limit of 400 pM according to the equation LOD=3.3 (SD/S). Therefore, even in the environment including a high-concentration protein, it is possible to detect a target without a great change in detection limit. Thus, it is possible to simply detect dsDNA from various actual bio-samples in a short time without a purification process.

Figure 20A:
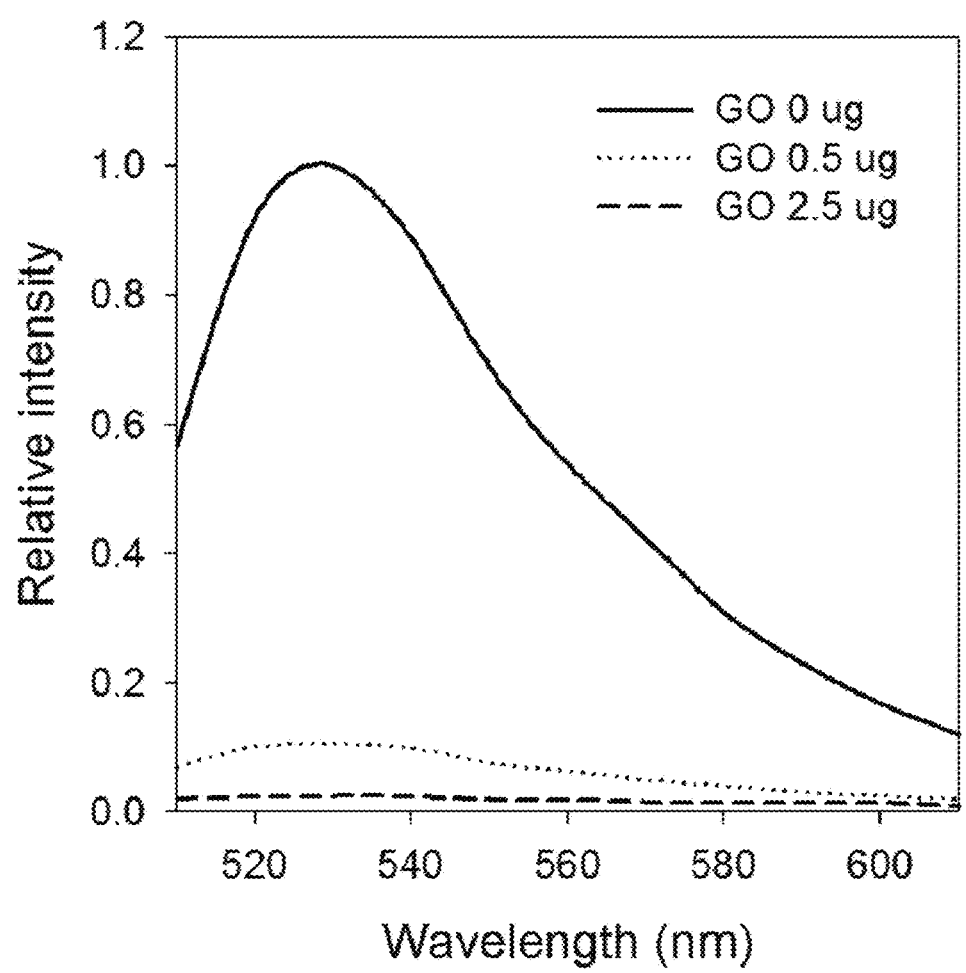
FIG. 20A to FIG. 20B show detection results of a target nucleic acid in accordance with an example of the present disclosure: (A) fluorescence spectra of a FAM conjugated to a PNA incubated with (0 μg, 0.5 μg and 2.5 μg of) a graphene oxide in 10% FBS-containing buffered solution; and (b) an increase (F/F0) in fluorescence intensity associated with a target in a wide concentration range (~500 nM) in 10% FBS-containing buffered solution (F: a fluorescence intensity of the PNA probe including the target, F0: the fluorescence intensity of the PNA probe without the target).
Figure 20B:
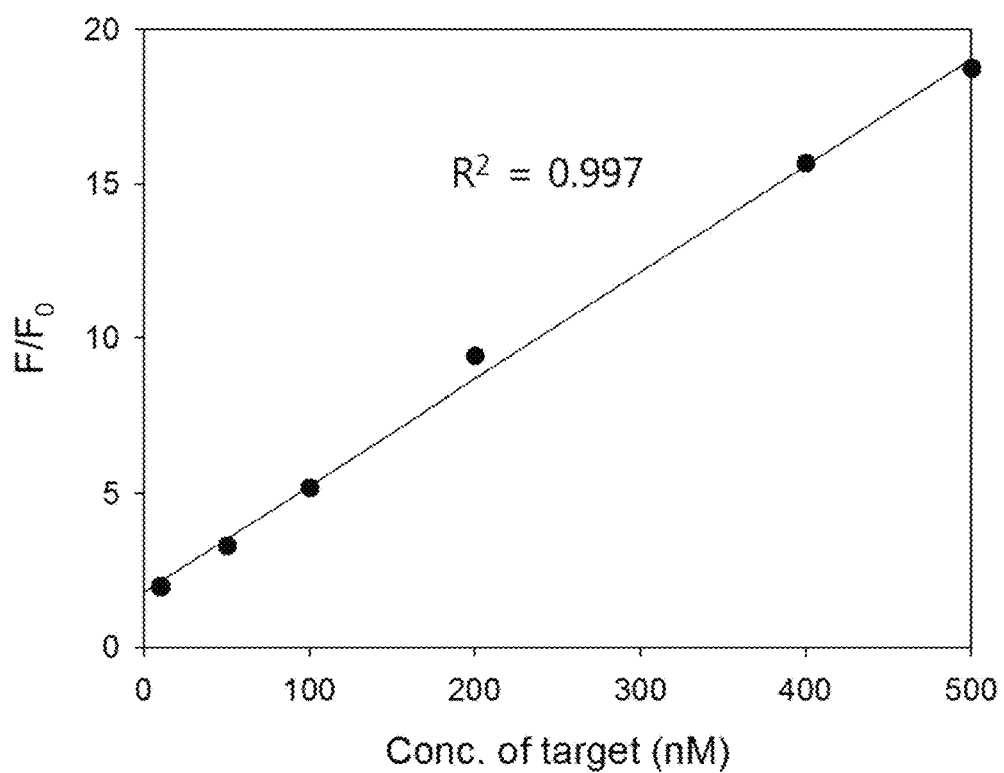

Further, detection of a target nucleic acid according to various concentrations (0 μg, 0.5 μg and 2.5 μg) of a graphene oxide and various concentrations (~500 nM) of a target nucleic acid was measured, and the results thereof were as shown in FIG. 20A and FIG. 20B. FIG. 20A shows fluorescence spectra of a FAM conjugated to a PNA incubated with various concentrations (0 μg, 0.5 μg and 2.5 μg) of a graphene oxide in a 10% FBS-containing buffered solution, and FIG. 20B shows an increase (F/F0) in fluorescence intensity associated with a target in a wide concentration range (~500 nM) in a 10% FBS-containing buffered solution (F: a fluorescence intensity of a PNA probe including a target, F0: a fluorescence intensity of a PNA probe without a target).

Example 14

Figure 21:
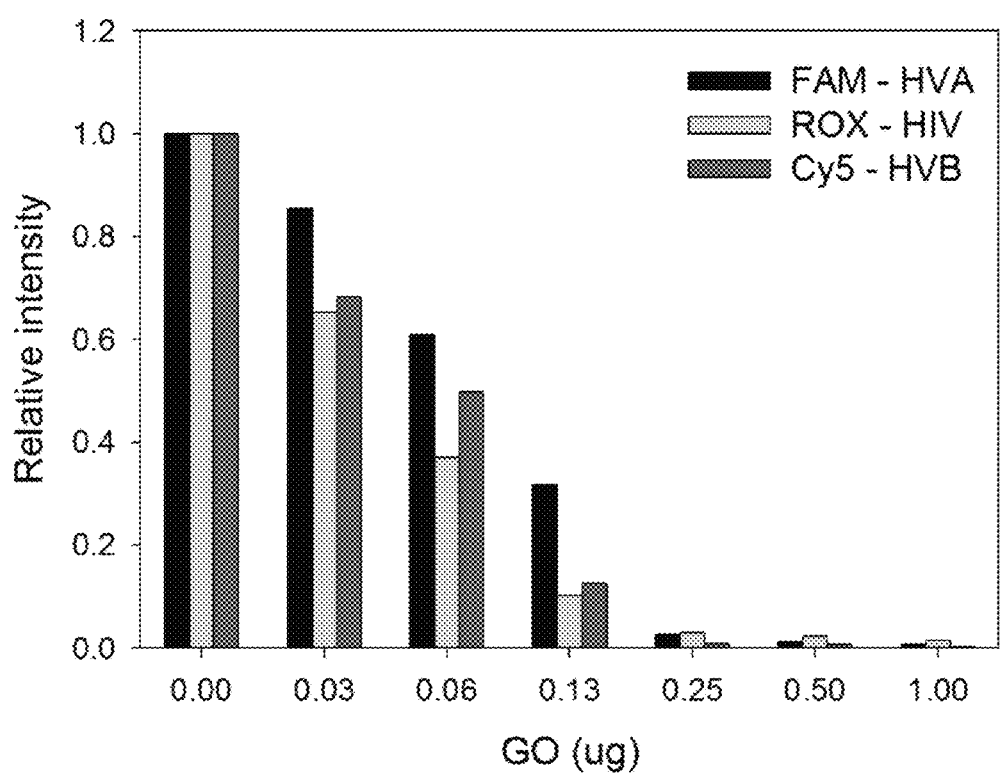
FIG. 21 shows a detection result of a target nucleic acid in accordance with an example of the present disclosure: relative fluorescence intensities of PNAs each labelled with three dyes in the presence of a graphene oxide; FAM, ROX, and Cy5 were conjugated to PNA probes for HVA, HIV, and HVB, respectively.

For multiplexed-target detection, a hepatitis A virus Val17 polyprotein gene (HVA), a human immunodeficiency virus (HIV), and a hepatitis B surface antigen (HVB) were used as double-stranded target DNAs. A double-stranded DNAs having 15 pb with a unique sequence derived from the three fatal viruses described in the above Table 3 were prepared, and conjugated with each of three different fluorescent dyes FAM, ROX (6-carboxyl-X-rhodamine) and Cy5 (cyanine 5) which showed emission maxima of 518 nm (green), 608 nm (orange), and 670 nm (red) excited at 492 nm, 587 nm, and 650 nm, respectively. Each of the double-stranded target DNA or different combinations of the three double-stranded DNA (200 nM) were incubated with the PNA probe mixtures (each concentration=100 nM) containing 10 pmol of FAM-HVA probe, ROX-HIV probe and Cy5-HVB probe (the sequences of the probes were as shown in Table 4), respectively, in 1×PBS. After the incubation at room temperature for 1 hour, 1.25 μL of 500 μg/mL graphene oxide stock was added to the mixtures (FIG. 21).

Figure 22:
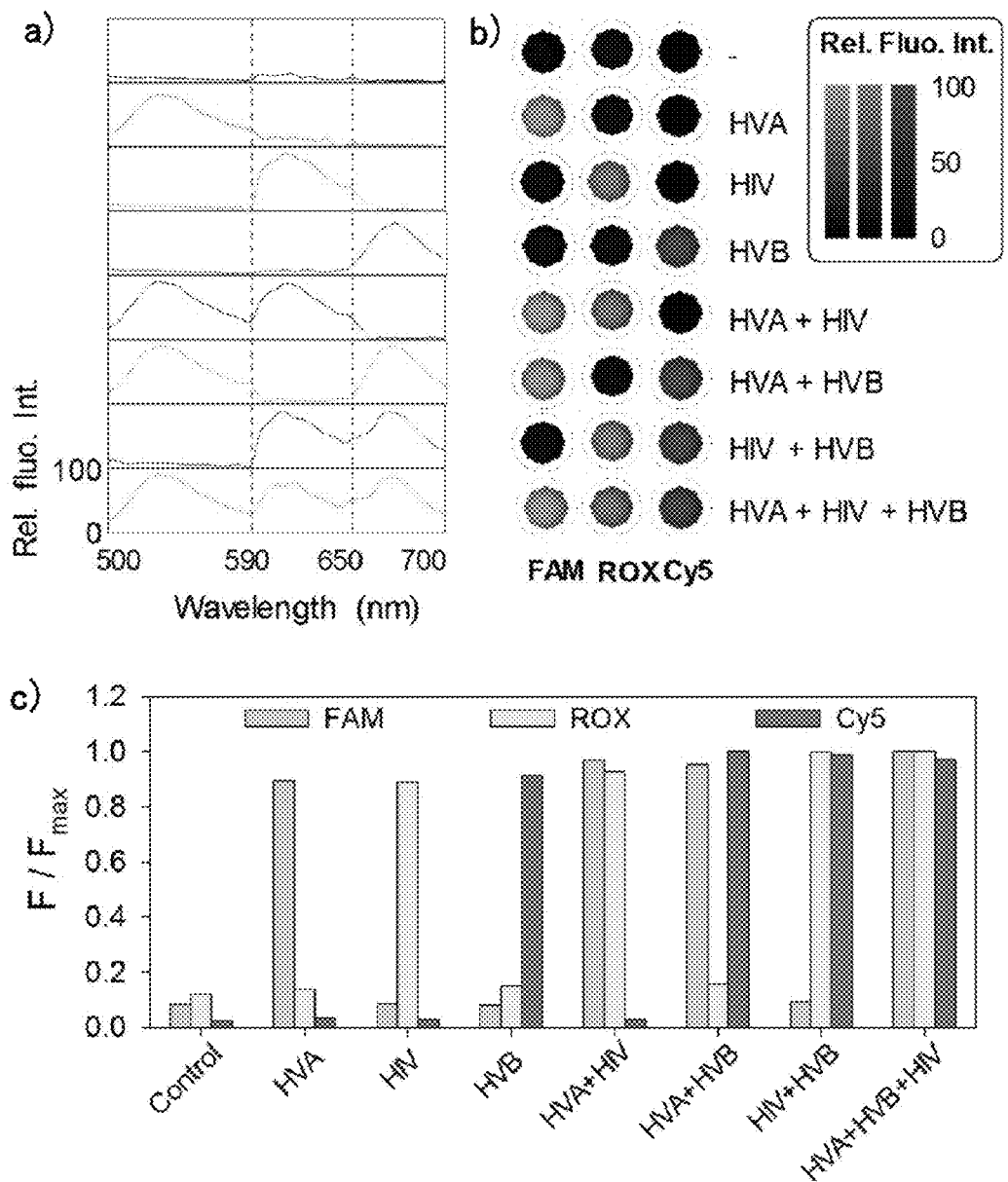
FIG. 22 shows a detection result of a target nucleic acid in accordance with an example of the present disclosure: multi-target detection of three virus genes within a single solution; (a) fluorescence spectra of a PNA labelled with three dyes in the presence of 200 nM target dsDNA in buffered solution; (b) fluorescence images of reaction mixtures for multiplexed-detection; Column 1: a fluorescence signal of FAM-HVA; Column 2: a fluorescence signal of FAM-HVB; Column 3: a fluorescence signal of FAM-HIV in the presence of each 200 nM target; and (c) a bar graph showing relative fluorescence intensities of PNAs each labelled with three dyes in the presence of each target dsDNA (200 nM) (F: the fluorescence intensity of the PNA having the target, Fmax: the fluorescence intensity of each of the PNAs probe observed when a perfectly matched duplex target is present).

The FAM-PNA, ROX-PNA, and Cy5-PNA were excited at 492 nm, 587 nm, and 650 nm, respectively, in a homogeneous solution. The fluorescence intensities of the probes were measured at 518 nm, 608 nm, and 670 nm, respectively (Fluorometer: SynergyMx, Biotek, UK)). Green, orange, and red fluorescence emission spectra and images were obtained only from the samples containing each corresponding HVA, HIV, and HVB double-stranded target DNA ((a) and (b) of FIG. 22). Further, a sequence-specific fluorescence response could be confirmed from a bar graph showing fluorescence intensities respectively obtained from different combinations of analyte double-stranded DNAs ((c) of FIG. 22).

As a result, according to the present disclosure, it is possible to prepare a novel GO-based platform for detecting a double-stranded DNA using a PNA probe. This demonstrates its usefulness by attempting to sequence-specifically and quantitatively detecting the double-stranded DNA on the basis of the graphene oxide for the first time. A double-stranded DNA sensor of the present example uses unique properties of a PNA and a graphene oxide. Firstly, the PNA invades at termini of a complementary strand of a double-stranded target DNA without limitation in sequence and then induces strand displacement using high binding affinity of the PNA with respect to its complementary DNA. Secondly, the graphene oxide has a high adsorption capability for to an uncharged ssPNA as compared with other biomolecules such as proteins and naturally occurring nucleic acids. Further, the graphene oxide effectively quenches a fluorescent light of a dye attached to the PNA probe. By combining the PNA probe with the graphene oxide according to the present disclosure, a quantitative fluorometric double-stranded DNA sensing is enable even in the serum-containing sample without a wide variation in LOD, which cannot be achieved in the case of using a DNA probe. Thus, it is a unique effect of the present disclosure. If a combination of the PNA and the graphene oxide is used for detecting the nucleic acid according to the present disclosure, it is possible to solve the problems of a conventional DNA or RNA probe. Therefore, a graphene oxide-based sensor can be applied to more fields. The double-stranded DNA sensor also has the advantage of being technically simple and compatible with multiplexed detection formats. In the method for detecting the nucleic acid of the present disclosure, various samples may be used and the quantitative multiplex detection of the target nucleic acid can be performed by obtaining a fluorescent image of the samples after mixing and incubation without performing cumbersome multiple steps. A double-stranded DNA detection platform according to the present disclosure can be set by changing the sequence of a PNA probe according to the sequence of a target DNA. Therefore, it has the advantage of being applicable to detection of various nucleic acids without any limitation in sequence. This novel method for detecting a nucleic acid directly based on a graphene oxide using the PNA probe of the present disclosure can be usefully applied to diagnosis of viral disease and genetic disorders and the personalized medicine field.

Example 15

In order to check detection efficiency depending on a temperature, a fluorescence intensity was measured at various temperatures of from about 25° C. to about 75° C.

let-7a miRNA (SEQ ID NO. 29) was used as a target, and let-7c miRNA (SEQ ID NO. 20) and let-7f miRNA (SEQ ID NO. 31) each having a single nucleotide polymorphism at various positions with respect to a base sequence of the let-7a miRNA were selected as control groups (Table 5). Firstly, a FAM fluorescent dye was attached to a PNA (SEQ ID NO. 34) (Table 4) having a base sequence complementary to the target let-7a miRNA. A resultant product was put into a 1×PBS solution together with the let-7 miRNAs selected as the target and the control groups and left at room temperature to induce formation of double strands. Herein, a graphene oxide was added to a non-selectively occurring double strand, and the mixture was incubated at room temperature (about 25° C.) or at various temperatures (from about 55° C. to about 75° C.) for 5 minutes. Finally, fluorescence signals of the mixtures decreased in temperature by being left at room temperature for about 2 minutes to about 3 minutes were measured to check a difference between the target miRNA and the miRNAs as the control groups.

TABLE 5

| Perfectly matched miRNA (let-7a) | SEQ ID NO. 19:<br>5' UGA GGU AGU AGG UUG UAU AGU U 3' |
|---|---|
| Single bp mismatched miRNA (let-7c) | SEQ ID NO. 20:<br>5' UGA GGU AGU AGG UUG UAU GGU U 3' |
| Single bp mismatched miRNA (let-7f) | SEQ ID NO. 21:<br>5' UGA GGU AGU AGA UUG UAU AGU U 3' |
| let-7a PNA probe | SEQ ID NO. 22:<br>5' FAM-OO-AAC TAT ACA ACC TAC TAC CTC A 3' |

Figure 23:
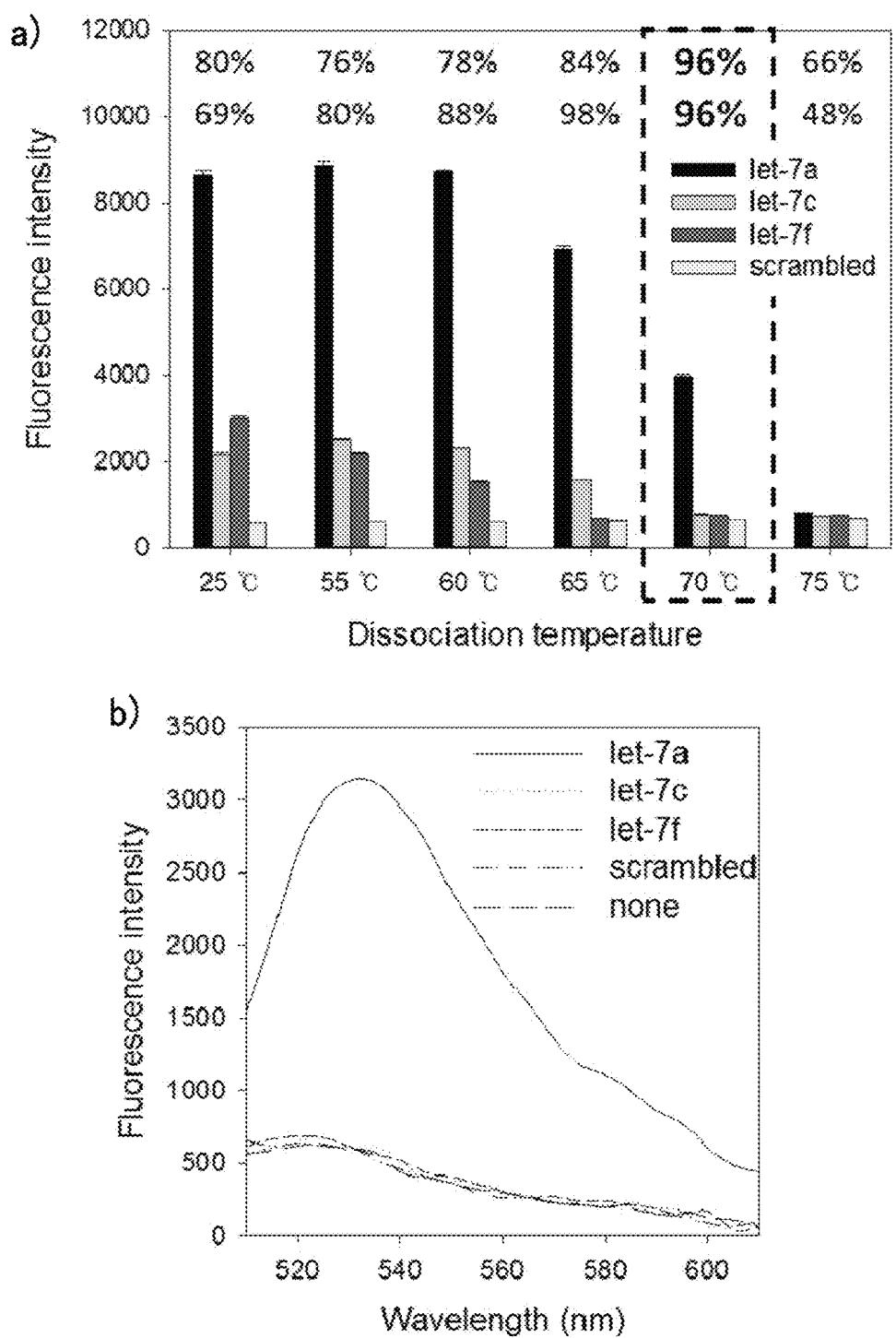
FIG. 23 provides a graph showing detection efficiency of a method of detecting a target nucleic acid depending on a temperature in accordance with an example of the present disclosure.

As can be seen from (a) of FIG. 23, at room temperature 25° C., a signal of 20% or more was detected from the target which was not perfectly matched. This signal could not be distinguished from a signal occurring when a small amount of the target is present. Meanwhile, when a temperature was adjusted to a high temperature, only a double strand having a mismatch was selectively separated and induced to be adsorbed on the graphene oxide, so that only a signal of 5% or less was detected ((b) of FIG. 23). This can be confirmed from the fact that only a perfectly matched target shows a strong fluorescence signal according to fluorescence spectrum analysis ((b) of FIG. 13). (Identification efficiency (%)=100*(F−Fscrambled/Fperfect matched−Fscrambled))

Figure 24:
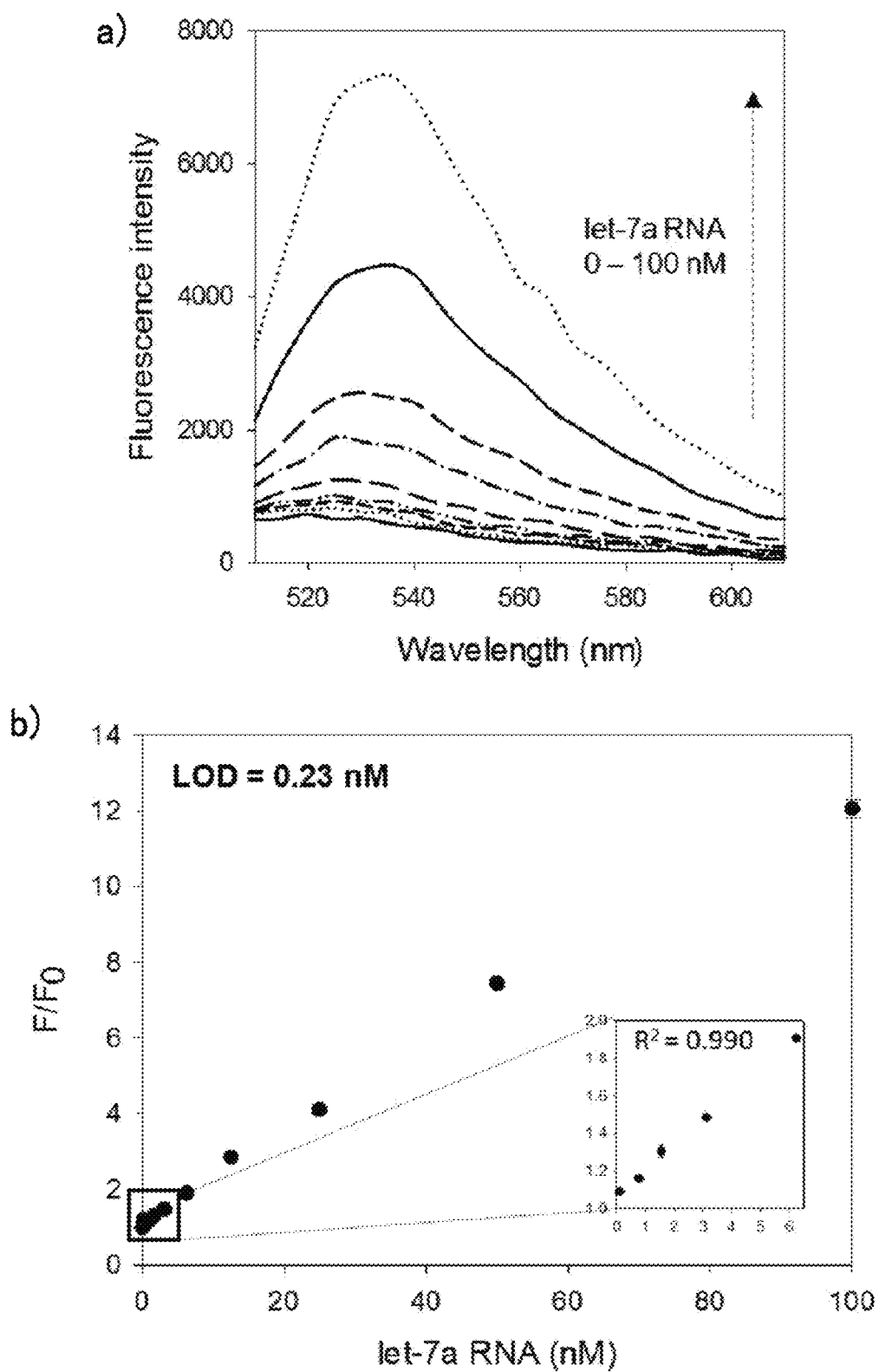
FIG. 24 provides a graph showing a detection result of a target nucleic acid in accordance with an example of the present disclosure.

As can be seen from FIG. 24, when a target was detected while adjusting a temperature, a fluorescence signal in proportion to a concentration of the target was shown ((a) of FIG. 24). When a detection limit was measured in the conditions (70° C., 5 minutes) for identifying a single mismatch, a concentration of about 0.23 nM (LOD=3.3 (SD/S)) was measured ((b) of FIG. 24). It was confirmed that when there is an attempt to detect a nucleic acid using a new system including a temperature adjusting step, it is possible to perfectly distinguish a single nucleotide polymorphism and also possible to quantitatively detect a target to a concentration of 0.23 nM.

Example 16

Figure 25:
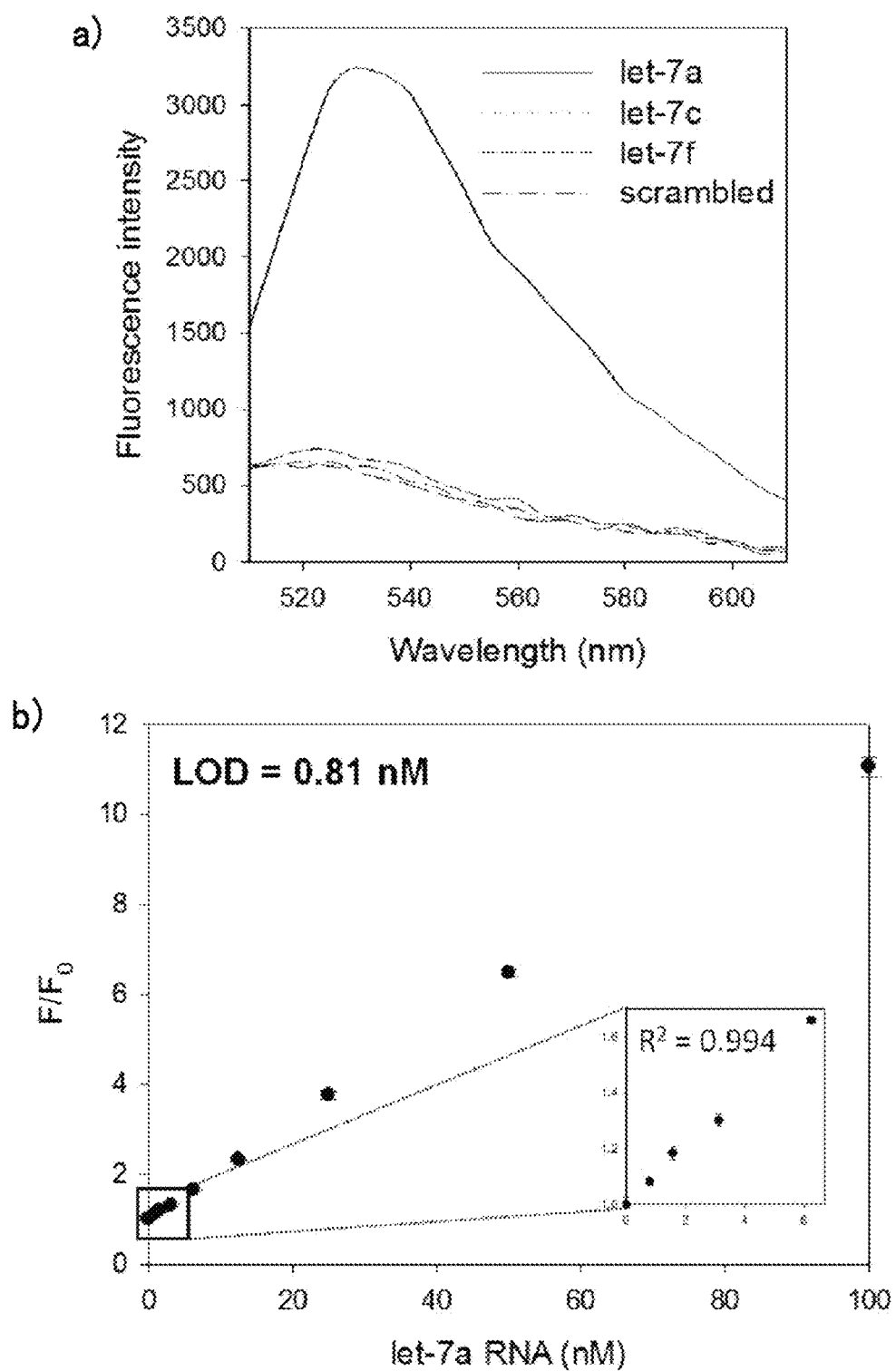
FIG. 25 provides a graph showing a detection result of a target nucleic acid in accordance with an example of the present disclosure.

The miRNAs as shown in Table 4 was put into a 1×PBS solution containing a lysate of Hela as a cervical cancer cell line to reproduce the environment for detecting a target in a body fluid containing proteins or the like in an actual diagnosis. Herein, each sample for detection contained a lysate of 10000 Hela cells and also contained various kinds of proteins, lipids, nucleic acids, etc. together with a target nucleic acid, and, thus, is similar to the environment of actual blood or tissue fluid. In the present step, an amount of a graphene oxide was adjusted again considering a change in intensity of an interaction between a PNA and the graphene oxide caused by various biomolecules to modify the detection conditions. By the same manner as Example 15, a PNA to which a fluorescent dye was attached was put into the aqueous solution containing the lysate and the target RNA to form a double strand. Then, a graphene oxide optimized for this condition was added thereto and a high-temperature treatment was performed for 5 minutes. Thus, only a perfectly matched target of a base sequence could be specifically detected ((a) of FIG. 25). In this environment, a detection limit was 0.81 nM, which was not greatly different from that in the environment in the PBS buffer ((b) of FIG. 25).

Example 17

Figure 26:
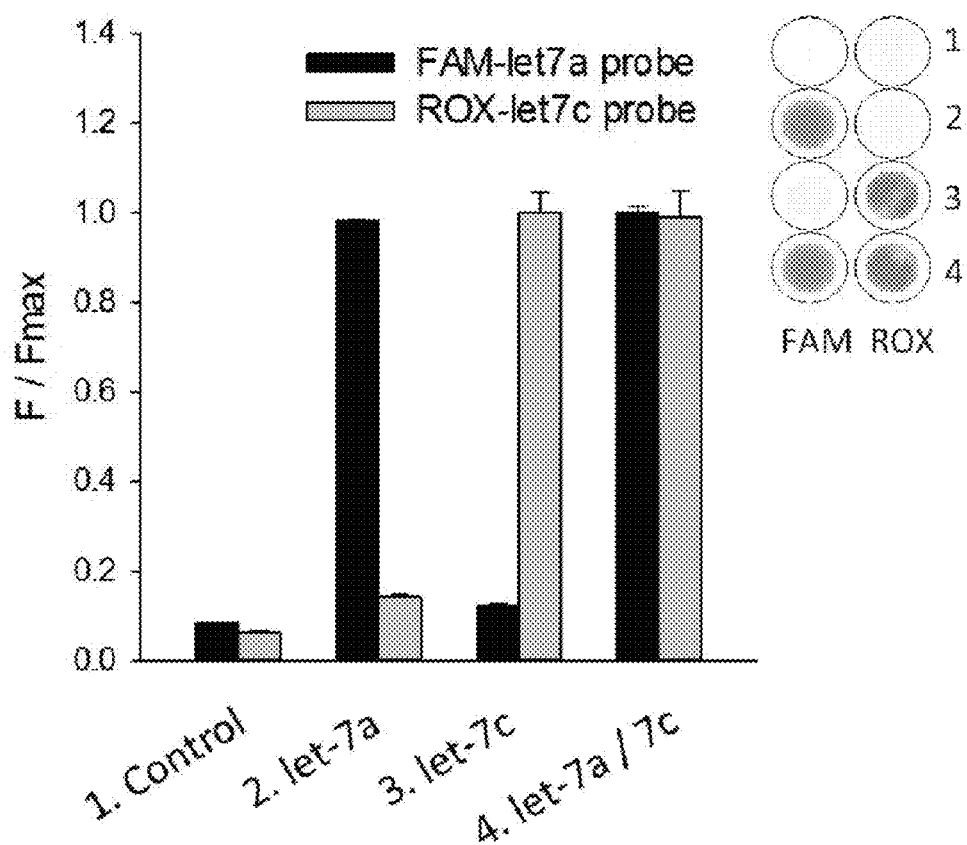
FIG. 26 shows a detection result of a multi-target nucleic acid in accordance with an example of the present disclosure.

In order to confirm that a multiplexed-detection capable of accurately detecting two targets different in a single base in an aqueous solution is enabled, the let-7a and the let-7c as used in Example 15 were used and signals of various combinations of the targets in the single aqueous solution were observed. PNAs (SEQ ID NO. 22: 5' FAM-OO-AAC TAT ACA ACC TAC TAC CTC A 3'; and SEQ ID NO. 23: 5' FAM-OO-AAC CAT ACA ACC TAC TAC CTC A 3') respectively having base sequences complementary to the two target RNAs were prepared and conjugated with fluorescent dyes FAM and ROX which showed emission maxima of 518 nm (green) and 608 nm (orange) excited at 492 nm and 587 nm, respectively. The two PNAs were added in the same amount to the aqueous buffered solution containing various combinations of the let-7a and let-7c miRNAs and then incubated to form a non-selective double strand. Thereafter, a graphene oxide was added thereto and a high-temperature treatment was performed for 5 minutes and then, left at room temperature. Consequently, as can be seen from FIG. 26, it was confirmed that a signal was shown only in the case where the target was included.

The scope of the inventive concept is defined by the following claims and their equivalents rather than by the detailed description of the example embodiments. It shall be understood that all modifications and embodiments conceived from the meaning and scope of the claims and their equivalents are included in the scope of the inventive concept.

We claim:

1. A method of detecting a nucleic acid, comprising:
a step of mixing at least one single stranded PNA probe with a sample including a target nucleic acid, wherein the at least one single stranded PNA probe is adsorbed on a graphene oxide and includes a fluorescent material; and
a step of detecting a fluorescent light emitted from the fluorescent material, wherein the target nucleic acid is combined with the at least one single stranded PNA probe upon the mixing step so that the at least one single stranded PNA probe is separated from the graphene oxide and the fluorescent light is emitted from the fluorescent material.

2. The method of claim 1, wherein the target nucleic acid includes an DNA or a RNA.

3. The method of claim 1, wherein the graphene oxide is in the form of a monolayer sheet.

4. The method of claim 1, wherein the at least one single stranded PNA probe includes one or more types of PNA probes containing different fluorescent materials respectively and the target nucleic acid includes one or more types of nucleic acids to be combined with the one or more types of PNA probes respectively so that multiplexed-detection of different nucleic acids is enabled.

5. The method of claim 1, wherein the emitting or quenching of the fluorescent light from the fluorescent material is detected in real time so that the target nucleic acid is detected in real time.

6. The method of claim 1, further comprising:
a step of heat-treating the mixture after the step of mixing the at least one single stranded PNA probe adsorbed on the graphene oxide with the sample including the target nucleic acid.

* * * * *

SEQUENCE LISTING

<160> NUMBER OF SEQ ID NOS: 33

<210> SEQ ID NO 1
<211> LENGTH: 21
<212> TYPE: DNA
<213> ORGANISM: Artificial Sequence
<220> FEATURE:
<223> OTHER INFORMATION: DNA strand

<400> SEQUENCE: 1
ataagcgtaa cttccctcaa a                    21

<210> SEQ ID NO 2
<211> LENGTH: 21

```
<212> TYPE: DNA
<213> ORGANISM: Artificial Sequence
<220> FEATURE:
<223> OTHER INFORMATION: DNA strand

<400> SEQUENCE: 2
tttgagggaa gttacgctta t                                               21

<210> SEQ ID NO 3
<211> LENGTH: 21
<212> TYPE: DNA
<213> ORGANISM: Artificial Sequence
<220> FEATURE:
<223> OTHER INFORMATION: DNA strand

<400> SEQUENCE: 3
ataagcgtaa cttccctcaa a                                               21

<210> SEQ ID NO 4
<211> LENGTH: 21
<212> TYPE: DNA
<213> ORGANISM: Artificial Sequence
<220> FEATURE:
<223> OTHER INFORMATION: DNA strand

<400> SEQUENCE: 4
tttgagggaa gatacgctta t                                               21

<210> SEQ ID NO 5
<211> LENGTH: 21
<212> TYPE: DNA
<213> ORGANISM: Artificial Sequence
<220> FEATURE:
<223> OTHER INFORMATION: DNA strand

<400> SEQUENCE: 5
ataagcgaat ctaccctcaa a                                               21

<210> SEQ ID NO 6
<211> LENGTH: 21
<212> TYPE: DNA
<213> ORGANISM: Artificial Sequence
<220> FEATURE:
<223> OTHER INFORMATION: DNA strand

<400> SEQUENCE: 6
tttgagggta gattcgctta t                                               21

<210> SEQ ID NO 7
<211> LENGTH: 22
<212> TYPE: DNA
<213> ORGANISM: Artificial Sequence
<220> FEATURE:
<223> OTHER INFORMATION: DNA strand

<400> SEQUENCE: 7
tagcttatca gactgatgtt ga                                              22

<210> SEQ ID NO 8
<211> LENGTH: 22
<212> TYPE: DNA
<213> ORGANISM: Artificial Sequence
<220> FEATURE:
<223> OTHER INFORMATION: DNA strand

<400> SEQUENCE: 8
```

```
tcaacatcag tctgataagc ta                                         22

<210> SEQ ID NO 9
<211> LENGTH: 15
<212> TYPE: DNA
<213> ORGANISM: HVA

<400> SEQUENCE: 9
ttagagttgc atgga                                                 15

<210> SEQ ID NO 10
<211> LENGTH: 15
<212> TYPE: DNA
<213> ORGANISM: HVA

<400> SEQUENCE: 10
tccatgcaac tctaa                                                 15

<210> SEQ ID NO 11
<211> LENGTH: 15
<212> TYPE: DNA
<213> ORGANISM: HIV

<400> SEQUENCE: 11
taacatgacc tggat                                                 15

<210> SEQ ID NO 12
<211> LENGTH: 15
<212> TYPE: DNA
<213> ORGANISM: HIV

<400> SEQUENCE: 12
atccaggtca tgtta                                                 15

<210> SEQ ID NO 13
<211> LENGTH: 15
<212> TYPE: DNA
<213> ORGANISM: HVB

<400> SEQUENCE: 13
atggatgatg tggta                                                 15

<210> SEQ ID NO 14
<211> LENGTH: 15
<212> TYPE: DNA
<213> ORGANISM: HVB

<400> SEQUENCE: 14
taccacatca tccat                                                 15

<210> SEQ ID NO 15
<211> LENGTH: 21
<212> TYPE: DNA
<213> ORGANISM: Artificial Sequence
<220> FEATURE:
<223> OTHER INFORMATION: PNA

<400> SEQUENCE: 15
tttgagggaa gttacgctta t                                          21

<210> SEQ ID NO 16
<211> LENGTH: 15
<212> TYPE: DNA
<213> ORGANISM: Artificial Sequence
```

<220> FEATURE:
<223> OTHER INFORMATION: PNA

<400> SEQUENCE: 16
tccatgcaac tctaa                                                     15

<210> SEQ ID NO 17
<211> LENGTH: 15
<212> TYPE: DNA
<213> ORGANISM: Artificial Sequence
<220> FEATURE:
<223> OTHER INFORMATION: PNA

<400> SEQUENCE: 17
atccaggtca tgtta                                                     15

<210> SEQ ID NO 18
<211> LENGTH: 15
<212> TYPE: DNA
<213> ORGANISM: Artificial Sequence
<220> FEATURE:
<223> OTHER INFORMATION: PNA

<400> SEQUENCE: 18
taccacatca tccat                                                     15

<210> SEQ ID NO 19
<211> LENGTH: 22
<212> TYPE: RNA
<213> ORGANISM: Artificial Sequence
<220> FEATURE:
<223> OTHER INFORMATION: miRNA

<400> SEQUENCE: 19
ugagguagua gguuguauag uu                                             22

<210> SEQ ID NO 20
<211> LENGTH: 22
<212> TYPE: RNA
<213> ORGANISM: Artificial Sequence
<220> FEATURE:
<223> OTHER INFORMATION: let-7 miRNA

<400> SEQUENCE: 20
ugagguagua gguuguaugg uu                                             22

<210> SEQ ID NO 21
<211> LENGTH: 22
<212> TYPE: RNA
<213> ORGANISM: Artificial Sequence
<220> FEATURE:
<223> OTHER INFORMATION: let-7 miRNA

<400> SEQUENCE: 21
ugagguagua gauuguauag uu                                             22

<210> SEQ ID NO 22
<211> LENGTH: 22
<212> TYPE: DNA
<213> ORGANISM: Artificial Sequence
<220> FEATURE:
<223> OTHER INFORMATION: PNA

<400> SEQUENCE: 22
aactatacaa cctactacct ca                                             22

```
<210> SEQ ID NO 23
<211> LENGTH: 22
<212> TYPE: DNA
<213> ORGANISM: Artificial Sequence
<220> FEATURE:
<223> OTHER INFORMATION: PNA

<400> SEQUENCE: 23
aaccatacaa cctactacct ca                                               22

<210> SEQ ID NO 24
<211> LENGTH: 22
<212> TYPE: RNA
<213> ORGANISM: Artificial Sequence
<220> FEATURE:
<223> OTHER INFORMATION: miRNA

<400> SEQUENCE: 24
uagcuuauca gacugauguu ga                                               22

<210> SEQ ID NO 25
<211> LENGTH: 22
<212> TYPE: DNA
<213> ORGANISM: Artificial Sequence
<220> FEATURE:
<223> OTHER INFORMATION: PNA

<400> SEQUENCE: 25
tcaacatcag tctgataagc ta                                               22

<210> SEQ ID NO 26
<211> LENGTH: 22
<212> TYPE: RNA
<213> ORGANISM: Artificial Sequence
<220> FEATURE:
<223> OTHER INFORMATION: miRNA

<400> SEQUENCE: 26
ucccugagac ccuaacuugu ga                                               22

<210> SEQ ID NO 27
<211> LENGTH: 22
<212> TYPE: DNA
<213> ORGANISM: Artificial Sequence
<220> FEATURE:
<223> OTHER INFORMATION: PNA

<400> SEQUENCE: 27
tcacaagtta gggtctcagg ga                                               22

<210> SEQ ID NO 28
<211> LENGTH: 23
<212> TYPE: RNA
<213> ORGANISM: Artificial Sequence
<220> FEATURE:
<223> OTHER INFORMATION: miRNA

<400> SEQUENCE: 28
uuaaugcuaa ucgugauagg ggu                                              23

<210> SEQ ID NO 29
<211> LENGTH: 18
<212> TYPE: DNA
<213> ORGANISM: Artificial Sequence
<220> FEATURE:
<223> OTHER INFORMATION: PNA
```

```
<400> SEQUENCE: 29
ctatcacgat tagcatta                                            18

<210> SEQ ID NO 30
<211> LENGTH: 21
<212> TYPE: RNA
<213> ORGANISM: Artificial Sequence
<220> FEATURE:
<223> OTHER INFORMATION: miRNA

<400> SEQUENCE: 30
uuuggauuga agggagcucu a                                        21

<210> SEQ ID NO 31
<211> LENGTH: 21
<212> TYPE: DNA
<213> ORGANISM: Artificial Sequence
<220> FEATURE:
<223> OTHER INFORMATION: PNA

<400> SEQUENCE: 31
tagagctccc ttcaatccaa a                                        21

<210> SEQ ID NO 32
<211> LENGTH: 22
<212> TYPE: RNA
<213> ORGANISM: Artificial Sequence
<220> FEATURE:
<223> OTHER INFORMATION: miRNA

<400> SEQUENCE: 32
uagcaccauc ugaaaucggu ua                                       22

<210> SEQ ID NO 33
<211> LENGTH: 22
<212> TYPE: DNA
<213> ORGANISM: Artificial Sequence
<220> FEATURE:
<223> OTHER INFORMATION: PNA

<400> SEQUENCE: 33
taaccgattt cagatggtgc ta                                       22
```